[12] United States Patent
Noireaux et al.

(10) Patent No.: US 7,063,829 B2
(45) Date of Patent: Jun. 20, 2006

(54) WASP FAMILY PROTEIN FRAGMENTS, AND USE THEREOF

(75) Inventors: Vincent Noireaux, Cormeray (FR); Jacques Prost, Paris (FR); Cecile Sykes, Paris (FR); Evelyne Friederich, Eschiallette (LU); Roy M. Golsteyn, Paris (FR); Daniel Louvard, Sceaux (FR)

(73) Assignees: Centre National de la Recherche Scientifique, Paris (FR); Institu Curie, Paris Cedex (FR)

( * ) Notice: Subject to any disclaimer, the term of this patent is extended or adjusted under 35 U.S.C. 154(b) by 0 days.

(21) Appl. No.: 10/168,097

(22) PCT Filed: Dec. 15, 2000

(86) PCT No.: PCT/FR00/03569

§ 371 (c)(1),
(2), (4) Date: Nov. 6, 2002

(87) PCT Pub. No.: WO01/44292

PCT Pub. Date: Jun. 21, 2001

(65) Prior Publication Data

US 2003/0166245 A1 Sep. 4, 2003

(30) Foreign Application Priority Data

Dec. 16, 1999 (FR) .................................. 99 15900

(51) Int. Cl.
*A61K 38/00* (2006.01)
*C12N 11/00* (2006.01)

(52) U.S. Cl. .......................... 424/9.1; 514/12; 530/300; 435/402

(58) Field of Classification Search .................. 514/12; 435/226, 254.2, 320.1, 34, 348; 530/300, 530/350; 424/9.1
See application file for complete search history.

(56) References Cited

OTHER PUBLICATIONS

Higgs, H. et al. "Influence of the C Terminus of Wiskott-Aldrich Syndrome Protein (WASP) and the Arp2/3 Complex on Actin Polymerization." Biochemistry 38: 15212-15222 1999.*
Symons et al. Cell 84: 723-734 (1996).*
Kato et al. Journal of Biological Chemistry 274(38): 27225-27230 (1999).*
Miki, H. and Takenawa, T. J. Biochem 134: 309-313 (2003).*
Higgs et al. "Influence of the C Terminus of Wiskott-Aldrich Syndrome Protein (WASp) and the Arp2/3 Complex on Actin Polymerization", BIOCHEMISTRY, vol. 38, No. 46, Nov. 16, 1999, pp. 15212-15222.
Linder et al. "Wiskott-Aldrich syndrome protein regulates podosomes in primary human macrophages", Proceedings of the National Acadamey of Sciences of USA, vol. 96, No. 17, Aug. 17, 1999, pp. 9648-9653.
Linder et al. "The Polarization Defect of Wiskott-Aldrich Syndrome Macrophages Is Linked to Dislocalization of the Arp2/3 Complex", Journal of Immunology, vol. 165, No. 1, Jul. 1, 2000, pp. 221-225.
Yarar et al. The Wiskott-Aldrich syndrome protein directs actin-based motility by stimulating actin nucleation with the Arp2/3 complex, Current Biology, vol. 9, No. 10, May 20, 1999, pp. 555-558.

* cited by examiner

Primary Examiner—Jon Weber
Assistant Examiner—Anand U. Desai
(74) Attorney, Agent, or Firm—Young & Thompson

(57) ABSTRACT

The invention concerns peptide fragments of the WASP family proteins, or peptides derived from said fragments, and their uses in particular for preparing reagents for use in implementing a method for detecting or screening molecules with inhibiting or stimulating effect on the formation of the actin cytoskeleton, hence an inhibiting or stimulating effect on cellular motility.

8 Claims, 26 Drawing Sheets

FIGURE 1

```
agcctcgcca gagaagacaa gggcagaaag cacc atg agt ggg ggc cca atg gga  55
                                     Met Ser Gly Gly Pro Met Gly
                                      1               5 gga agg ccc ggg ggc cga gga gca cca gcg gtt cag cag aac ata ccc  103
Gly Arg Pro Gly Gly Arg Gly Ala Pro Ala Val Gln Gln Asn Ile Pro
         10              15                  20 tcc acc ctc ctc cag gac cac gag aac cag cga ctc ttt gag atg ctt  151
Ser Thr Leu Leu Gln Asp His Glu Asn Gln Arg Leu Phe Glu Met Leu
     25                  30                  35 gga cga aaa tgc ttg acg ctg gcc act gca gtt gtt cag ctg tac ctg  199
Gly Arg Lys Cys Leu Thr Leu Ala Thr Ala Val Val Gln Leu Tyr Leu
 40              45                  50                  55 gcg ctg ccc cct gga gct gag cac tgg acc aag gag cat tgt ggg gct  247
Ala Leu Pro Pro Gly Ala Glu His Trp Thr Lys Glu His Cys Gly Ala
                 60                  65                  70 gtg tgc ttc gtg aag gat aac ccc cag aag tcc tac ttc atc cgc ctt  295
Val Cys Phe Val Lys Asp Asn Pro Gln Lys Ser Tyr Phe Ile Arg Leu
             75                  80                  85 tac ggc ctt cag gct ggt cgg ctg ctc tgg gaa cag gag ctg tac tca  343
Tyr Gly Leu Gln Ala Gly Arg Leu Leu Trp Glu Gln Glu Leu Tyr Ser
         90                  95                 100 cag ctt gtc tac tcc acc ccc acc ccc ttc ttc cac acc ttc gct gga  391
Gln Leu Val Tyr Ser Thr Pro Thr Pro Phe Phe His Thr Phe Ala Gly
    105                 110                 115 gat gac tgc caa gcg ggg ctg aac ttt gca gac gag gac gag gcc cag  439
Asp Asp Cys Gln Ala Gly Leu Asn Phe Ala Asp Glu Asp Glu Ala Gln
120                 125                 130                 135 gcc ttc cgg gcc ctc gtg cag gag aag ata caa aaa agg aat cag agg  487
Ala Phe Arg Ala Leu Val Gln Glu Lys Ile Gln Lys Arg Asn Gln Arg
                140                 145                 150 caa agt gga gac aga cgc cag cta ccc cca cca aca cca gcc aat  535
Gln Ser Gly Asp Arg Arg Gln Leu Pro Pro Pro Thr Pro Ala Asn
        155                 160                 165 gaa gag aga aga gga ggg ctc cca ccc ctg ccc ctg cat cca ggt gga  583
Glu Glu Arg Arg Gly Gly Leu Pro Pro Leu Pro Leu His Pro Gly Gly
        170                 175                 180 gac caa gga ggc cct cca gtg ggt ccg ctc tcc ctg ggg ctg gcg aca  631
Asp Gln Gly Gly Pro Pro Val Gly Pro Leu Ser Leu Gly Leu Ala Thr
185                 190                 195 gtg gac atc cag aac cct gac atc acg agt tca cga tac cgt ggg ctc  679
Val Asp Ile Gln Asn Pro Asp Ile Thr Ser Ser Arg Tyr Arg Gly Leu
200                 205                 210                 215
```

FIGURE 1 (suite 1)

```
cca gca cct gga cct agc cca gct gat aag aaa cgc tca ggg aag aag    727
Pro Ala Pro Gly Pro Ser Pro Ala Asp Lys Lys Arg Ser Gly Lys Lys
            220             225             230 aag atc agc aaa gct gat att ggt gca ccc agt gga ttc aag cat gtc    775
Lys Ile Ser Lys Ala Asp Ile Gly Ala Pro Ser Gly Phe Lys His Val
            235             240             245 agc cac gtg ggg tgg gac ccc cag aat gga ttt gac gtg aac aac ctc    823
Ser His Val Gly Trp Asp Pro Gln Asn Gly Phe Asp Val Asn Asn Leu
            250             255             260 gac cca gat ctg cgg agt ctg ttc tcc agg gca gga atc agc gag gcc    871
Asp Pro Asp Leu Arg Ser Leu Phe Ser Arg Ala Gly Ile Ser Glu Ala
            265             270             275 cag ctc acc gac gcc gag acc tct aaa ctt atc tac gac ttc att gag    919
Gln Leu Thr Asp Ala Glu Thr Ser Lys Leu Ile Tyr Asp Phe Ile Glu
280             285             290             295 gac cag ggt ggg ctg gag gct gtg cgg cag gag atg agg cgc cag gag    967
Asp Gln Gly Gly Leu Glu Ala Val Arg Gln Glu Met Arg Arg Gln Glu
            300             305             310 cca ctt ccg ccg ccc cca ccg cca tct cga gga ggg aac cag ctc ccc    1015
Pro Leu Pro Pro Pro Pro Pro Pro Ser Arg Gly Gly Asn Gln Leu Pro
            315             320             325 cgg ccc cct att gtg ggg ggt aac aag ggt cgt tct ggt cca ctg ccc    1063
Arg Pro Pro Ile Val Gly Gly Asn Lys Gly Arg Ser Gly Pro Leu Pro
            330             335             340 cct gta cct ttg ggg att gcc cca ccc cca aca ccc cgg gga ccc        1111
Pro Val Pro Leu Gly Ile Ala Pro Pro Pro Thr Pro Arg Gly Pro
            345             350             355 cca ccc cca ggc cga ggg ggc cct cca cca cca ccc cct cca gct act    1159
Pro Pro Pro Gly Arg Gly Gly Pro Pro Pro Pro Pro Pro Ala Thr
360             365             370             375 gga cgt tct gga cca ctg ccc cct cca ccc cct gga gct ggt ggg cca    1207
Gly Arg Ser Gly Pro Leu Pro Pro Pro Pro Gly Ala Gly Gly Pro
            380             385             390 ccc atg cca cca cca ccg cca cca ccg cca ccg ccc agc tcc ggg        1255
Pro Met Pro Pro Pro Pro Pro Pro Pro Pro Pro Pro Ser Ser Gly
            395             400             405 aat gga cca gcc cct ccc cca ctc cct cct gct ctg gtg cct gcc ggg    1303
Asn Gly Pro Ala Pro Pro Pro Leu Pro Pro Ala Leu Val Pro Ala Gly
            410             415             420 ggc ctg gcc cct ggt ggg ggt cgg gga gcg ctt ttg gat caa atc cgg    1351
Gly Leu Ala Pro Gly Gly Gly Arg Gly Ala Leu Leu Asp Gln Ile Arg
            425             430             435
```

FIGURE 1 (suite 2)

```
cag gga att cag ctg aac aag acc cct ggg gcc cca gag agc tca gcg   1399
Gln Gly Ile Gln Leu Asn Lys Thr Pro Gly Ala Pro Glu Ser Ser Ala
440             445             450             455 ctg cag cca cca cct cag agc tca gag gga ctg gtg ggg gcc ctg atg   1447
Leu Gln Pro Pro Pro Gln Ser Ser Glu Gly Leu Val Gly Ala Leu Met
            460             465             470 cac gtg atg cag aag aga agc aga gcc atc cac tcc tcc gac gaa ggg   1495
His Val Met Gln Lys Arg Ser Arg Ala Ile His Ser Ser Asp Glu Gly
        475             480             485 gag gac cag gct ggc gat gaa gat gaa gat gat gaa tgg gat gac       1540
Glu Asp Gln Ala Gly Asp Glu Asp Glu Asp Asp Glu Trp Asp Asp
        490             495             500 tgagtggctg agttacttgc tgccctgtgc tcctcccgc aggacatggc tccccctcca 1600
cctgctctgt gcccaccctc cactctcctc ttccagggcc cccaaccccc catttcttcc 1660
ccaccaaccc ctccaatgct gttatccctg cctggtcctc acactcaccc aacaatccca 1720 aggcccttt tatacaaaaa ttctcagttc tcttcactca aggatttta aagaaaaata 1780 aaagaattgt ctttctgtct ctctat                                     1806
```

FIGURE 2

```
atg agc tcc gtc cag cag cag ccg ccg ccg ccg cgg agg gtc acc aac    48
Met Ser Ser Val Gln Gln Gln Pro Pro Pro Pro Arg Arg Val Thr Asn
 1               5                  10                  15 gtg ggg tcc ctg ttg ctc acc ccg cag gag aac gag tcc ctc ttc act    96
Val Gly Ser Leu Leu Leu Thr Pro Gln Glu Asn Glu Ser Leu Phe Thr
                20                  25                  30 ttc ctc ggc aag aaa tgt gtg act atg tct tca gca gtg gtg cag tta   144
Phe Leu Gly Lys Lys Cys Val Thr Met Ser Ser Ala Val Val Gln Leu
            35                  40                  45 tat gca gca gat cgg aac tgt atg tgg tca aag aag tgc agt ggt gtt   192
Tyr Ala Ala Asp Arg Asn Cys Met Trp Ser Lys Lys Cys Ser Gly Val
        50                  55                  60 gct tgt ctt gtt aag gac aat cca cag aga tct cat ttt tta aga ata   240
Ala Cys Leu Val Lys Asp Asn Pro Gln Arg Ser His Phe Leu Arg Ile
65                  70                  75                  80 ttt gac att aag gat ggg aaa cta ttg tgg gaa caa gag cta tac aat   288
Phe Asp Ile Lys Asp Gly Lys Leu Leu Trp Glu Gln Glu Leu Tyr Asn
                85                  90                  95 aac ttt gta tat aat agt cct aga gga tat ttt cat acc ttt gct gga   336
Asn Phe Val Tyr Asn Ser Pro Arg Gly Tyr Phe His Thr Phe Ala Gly
               100                 105                 110 gat act tgt caa gtt gct ctt aat ttt gcc aat gaa gaa gaa gca aaa   384
Asp Thr Cys Gln Val Ala Leu Asn Phe Ala Asn Glu Glu Glu Ala Lys
           115                 120                 125 aaa ttt cga aaa gca gtt aca gac ctt ttg ggc cgt cga caa agg aaa   432
Lys Phe Arg Lys Ala Val Thr Asp Leu Leu Gly Arg Arg Gln Arg Lys
130                 135                 140 tct gag aaa aga cga gat ccc cca aat ggt cct aat cta ccc atg gct   480
Ser Glu Lys Arg Arg Asp Pro Pro Asn Gly Pro Asn Leu Pro Met Ala
145                 150                 155                 160 aca gtt gat ata aaa aat cca gaa atc aca aca aat aga ttt tat ggt   528
Thr Val Asp Ile Lys Asn Pro Glu Ile Thr Thr Asn Arg Phe Tyr Gly
               165                 170                 175 cca caa gtc aac aac atc tcc cat acc aaa gaa aag aag aag gga aaa   576
Pro Gln Val Asn Asn Ile Ser His Thr Lys Glu Lys Lys Lys Gly Lys
           180                 185                 190 gct aaa aag aag aga tta acc aag gga gat ata gga aca cca agc aat   624
Ala Lys Lys Lys Arg Leu Thr Lys Gly Asp Ile Gly Thr Pro Ser Asn
               195                 200                 205 ttc cag cac att gga cat gtt ggt tgg gat cca aat aca ggc tct gat   672
Phe Gln His Ile Gly His Val Gly Trp Asp Pro Asn Thr Gly Ser Asp
           210                 215                 220
```

FIGURE 2 (suite 1)

```
ctg aat aat ttg gat cca gaa ttg aag aat ctt ttt gat atg tgt gga    720
Leu Asn Asn Leu Asp Pro Glu Leu Lys Asn Leu Phe Asp Met Cys Gly
225             230                 235                 240 atc tta gag gca caa ctt aaa gaa aga gaa aca tta aaa gtt ata tat    768
Ile Leu Glu Ala Gln Leu Lys Glu Arg Glu Thr Leu Lys Val Ile Tyr
                245                 250                 255 gac ttt att gaa aaa aca gga ggt gtt gaa gct gtt aaa aat gaa ctg    816
Asp Phe Ile Glu Lys Thr Gly Gly Val Glu Ala Val Lys Asn Glu Leu
            260                 265                 270 cgg agg caa gca cca cca cct cca cca cca tca agg gga ggg cca cct    864
Arg Arg Gln Ala Pro Pro Pro Pro Pro Pro Ser Arg Gly Gly Pro Pro
        275                 280                 285 cct cct cct ccc cct cca cat agc tcg ggt cct cct cct cct cct gct    912
Pro Pro Pro Pro Pro Pro His Ser Ser Gly Pro Pro Pro Pro Pro Ala
    290                 295                 300 agg gga aga ggc gct cct ccc cca cca cct tca aga gct ccc aca gct    960
Arg Gly Arg Gly Ala Pro Pro Pro Pro Pro Ser Arg Ala Pro Thr Ala
305                 310                 315                 320 gca cct cca cca ccg cct cct tcc agg cca agt gta gaa gtc cct cca    1008
Ala Pro Pro Pro Pro Pro Pro Ser Arg Pro Ser Val Glu Val Pro Pro
                325                 330                 335 cca ccg cca aat agg atg tac cct cct cca cct cca gcc ctt ccc tcc    1056
Pro Pro Pro Asn Arg Met Tyr Pro Pro Pro Pro Ala Leu Pro Ser
            340                 345                 350 tca gca cct tca ggg cct cca cca cca cct tct gtg ttg ggg gta        1104
Ser Ala Pro Ser Gly Pro Pro Pro Pro Pro Ser Val Leu Gly Val
        355                 360                 365 ggg cca gtg gca cca ccc cca ccg cct cca cct cct cct ggg            1152
Gly Pro Val Ala Pro Pro Pro Pro Pro Pro Pro Pro Pro Gly
    370                 375                 380 cca ccg ccc ccg cct ggc ctg cct tct gat ggg gac cat cag gtt cca    1200
Pro Pro Pro Pro Pro Gly Leu Pro Ser Asp Gly Asp His Gln Val Pro
385                 390                 395                 400 act act gca gga aac aaa gca gct ctt tta gat caa att aga gag ggt    1248
Thr Thr Ala Gly Asn Lys Ala Ala Leu Leu Asp Gln Ile Arg Glu Gly
                405                 410                 415 gct cag cta aaa aaa gtg gag cag aac agt cgg cca gtg tcc tgc tct    1296
Ala Gln Leu Lys Lys Val Glu Gln Asn Ser Arg Pro Val Ser Cys Ser
            420                 425                 430
```

FIGURE 2 (suite 2)

```
gga cga gat gca ctg tta gac cag ata cga cag ggt atc caa cta aaa   1344
Gly Arg Asp Ala Leu Leu Asp Gln Ile Arg Gln Gly Ile Gln Leu Lys
        435                 440                 445 tct gtg gct gat ggc caa gag tct aca cca cca aca cct gca ccc act   1392
Ser Val Ala Asp Gly Gln Glu Ser Thr Pro Pro Thr Pro Ala Pro Thr
        450                 455                 460 tca gga att gtg ggt gca tta atg gaa gtg atg cag aaa agg agc aaa   1440
Ser Gly Ile Val Gly Ala Leu Met Glu Val Met Gln Lys Arg Ser Lys
465                 470                 475                 480 gcc att cat tct tca gat gaa gat gaa gat gaa gat gat gaa gaa gat   1488
Ala Ile His Ser Ser Asp Glu Asp Glu Asp Glu Asp Asp Glu Glu Asp
                485                 490                 495 ttt gag gat gat gat gag tgg gaa gac tga                           1518
Phe Glu Asp Asp Asp Glu Trp Glu Asp
        500                 505
```

FIGURE 3

| | |
|---|---|
| atg ccg cta gtg aaa aga aac atc gat cct agg cac ttg tgc cac aca<br>Met Pro Leu Val Lys Arg Asn Ile Asp Pro Arg His Leu Cys His Thr<br>1                         5                        10                      15 | 48 |
| gca ctg cct aga ggc att aag aat gaa ctg gaa tgt gta acc aat att<br>Ala Leu Pro Arg Gly Ile Lys Asn Glu Leu Glu Cys Val Thr Asn Ile<br>              20                        25                        30 | 96 |
| tcc ttg gca aat ata att aga caa cta agt agc cta agt aaa tat gct<br>Ser Leu Ala Asn Ile Ile Arg Gln Leu Ser Ser Leu Ser Lys Tyr Ala<br>            35                        40                        45 | 144 |
| gaa gat ata ttt gga gaa tta ttc aat gaa gca cat agt ttt tcc ttc<br>Glu Asp Ile Phe Gly Glu Leu Phe Asn Glu Ala His Ser Phe Ser Phe<br>            50                        55                        60 | 192 |
| aga gtc aac tca ttg caa gaa cgt gtg gac cgt tta tct gtt agt gtt<br>Arg Val Asn Ser Leu Gln Glu Arg Val Asp Arg Leu Ser Val Ser Val<br>65                        70                        75                      80 | 240 |
| aca cag ctt gat cca aag gaa gaa gaa ttg tct ttg caa gat ata aca<br>Thr Gln Leu Asp Pro Lys Glu Glu Glu Leu Ser Leu Gln Asp Ile Thr<br>                      85                        90                        95 | 288 |
| atg agg aaa gct ttc cga agt tct aca att caa gac cag cag ctt ttc<br>Met Arg Lys Ala Phe Arg Ser Ser Thr Ile Gln Asp Gln Gln Leu Phe<br>                    100                      105                      110 | 336 |
| gat cgc aag act ttg cct att cca tta cag gag acg tac gat gtt tgt<br>Asp Arg Lys Thr Leu Pro Ile Pro Leu Gln Glu Thr Tyr Asp Val Cys<br>                  115                      120                      125 | 384 |
| gaa cag cct cca cct ctc aat ata ctc act cct tat aga gat gat ggt<br>Glu Gln Pro Pro Pro Leu Asn Ile Leu Thr Pro Tyr Arg Asp Asp Gly<br>            130                      135                      140 | 432 |
| aaa gaa ggt ctg aag ttt tat acc aat cct tcg tat ttc ttt gat cta<br>Lys Glu Gly Leu Lys Phe Tyr Thr Asn Pro Ser Tyr Phe Phe Asp Leu<br>145                        150                        155                      160 | 480 |
| tgg aaa gaa aaa atg ttg caa gat aca gag gat aag agg aag gaa aag<br>Trp Lys Glu Lys Met Leu Gln Asp Thr Glu Asp Lys Arg Lys Glu Lys<br>                    165                      170                      175 | 528 |
| agg aag cag aag cag aaa aat cta gat cgt cct cat gaa cca gaa aaa<br>Arg Lys Gln Lys Gln Lys Asn Leu Asp Arg Pro His Glu Pro Glu Lys<br>                  180                      185                      190 | 576 |
| gtg cca aga gca cct cat gac agg cgg cga gaa tgg cag aag ctg gcc<br>Val Pro Arg Ala Pro His Asp Arg Arg Arg Glu Trp Gln Lys Leu Ala<br>            195                      200                      205 | 624 |

FIGURE 3 (suite 1)

```
caa ggt cca gag ctg gct gaa gat gat gct aat ctc tta cat aag cat    672
Gln Gly Pro Glu Leu Ala Glu Asp Asp Ala Asn Leu Leu His Lys His
        210                 215                 220 att gaa gtt gct aat ggc cca gcc tct cat ttt gaa aca aga cct cag    720
Ile Glu Val Ala Asn Gly Pro Ala Ser His Phe Glu Thr Arg Pro Gln
225                 230                 235                 240 aca tac gtg gat cat atg gat gga tct tac tca ctt tct gcc ttg cca    768
Thr Tyr Val Asp His Met Asp Gly Ser Tyr Ser Leu Ser Ala Leu Pro
                245                 250                 255 ttt agt cag atg agt gag ctt ctg act aga gct gag gaa agg gta tta    816
Phe Ser Gln Met Ser Glu Leu Leu Thr Arg Ala Glu Glu Arg Val Leu
        260                 265                 270 gtc aga cca cat gaa cca cct cca cct cca atg cat gga gca gga        864
Val Arg Pro His Glu Pro Pro Pro Pro Pro Met His Gly Ala Gly
            275                 280                 285 gat gca aaa ccg ata ccc acc tgt atc agt tct gct aca ggt ttg ata    912
Asp Ala Lys Pro Ile Pro Thr Cys Ile Ser Ser Ala Thr Gly Leu Ile
        290                 295                 300 gaa aat cgc cct cag tca cca gct aca ggc aga aca cct gtg ttt gtg    960
Glu Asn Arg Pro Gln Ser Pro Ala Thr Gly Arg Thr Pro Val Phe Val
305                 310                 315                 320 agc ccc act ccc cca cct cct cca cca cct ctt cca tct gcc ttg tca   1008
Ser Pro Thr Pro Pro Pro Pro Pro Pro Leu Pro Ser Ala Leu Ser
                325                 330                 335 act tcc tca tta aga gct tca atg act tca act cct ccc cct cca gta   1056
Thr Ser Ser Leu Arg Ala Ser Met Thr Ser Thr Pro Pro Pro Pro Val
        340                 345                 350 cct ccc cca cct cca cct cca gcc act gct ttg caa gct cca gca gta   1104
Pro Pro Pro Pro Pro Pro Pro Ala Thr Ala Leu Gln Ala Pro Ala Val
            355                 360                 365 cca cca cct cca gct cct ctt cag att gcc cct gga gtt ctt cac cca   1152
Pro Pro Pro Pro Ala Pro Leu Gln Ile Ala Pro Gly Val Leu His Pro
        370                 375                 380 gct cct cct cca att gca cct cct cta gta cag ccc tct cca cca gta   1200
Ala Pro Pro Pro Ile Ala Pro Pro Leu Val Gln Pro Ser Pro Pro Val
385                 390                 395                 400 gct aga gct gcc cca gta tgt gag act gta cca gtt cat cca ctc cca   1248
Ala Arg Ala Ala Pro Val Cys Glu Thr Val Pro Val His Pro Leu Pro
                405                 410                 415
```

FIGURE 3 (suite 2)

```
caa ggt gaa gtt cag ggg ctg cct cca ccc cca cca ccg cct cct ctg    1296
Gln Gly Glu Val Gln Gly Leu Pro Pro Pro Pro Pro Pro Pro Pro Leu
            420                 425                 430 cct cca cct ggc att cga cca tca tca cct gtc aca gtt aca gct ctt    1344
Pro Pro Pro Gly Ile Arg Pro Ser Ser Pro Val Thr Val Thr Ala Leu
            435                 440                 445 gct cat cct ccc tct ggg cta cat cca act cca tct act gcc cca ggt    1392
Ala His Pro Pro Ser Gly Leu His Pro Thr Pro Ser Thr Ala Pro Gly
            450                 455                 460 ccc cat gtt cca tta atg cct cca tct cct cca tca caa gtt ata cct    1440
Pro His Val Pro Leu Met Pro Pro Ser Pro Pro Ser Gln Val Ile Pro
465                 470                 475                 480 gct tct gag cca aag cgc cat cca tca acc cta cct gta atc agt gat    1488
Ala Ser Glu Pro Lys Arg His Pro Ser Thr Leu Pro Val Ile Ser Asp
                485                 490                 495 gcc agg agt gtg cta ctg gaa gca ata cga aaa ggt att cag cta cgc    1536
Ala Arg Ser Val Leu Leu Glu Ala Ile Arg Lys Gly Ile Gln Leu Arg
            500                 505                 510 aaa gta gaa gag cag cgt gaa cag gaa gct aag cat gaa cgc att gaa    1584
Lys Val Glu Glu Gln Arg Glu Gln Glu Ala Lys His Glu Arg Ile Glu
            515                 520                 525 aac gat gtt gcc acc atc ctg tct cgc cgt att gct gtt gaa tat agt    1632
Asn Asp Val Ala Thr Ile Leu Ser Arg Arg Ile Ala Val Glu Tyr Ser
            530                 535                 540 gat tcg gaa gat gat tca gaa ttt gat gaa gta gat tgg ttg gag taa    1680
Asp Ser Glu Asp Asp Ser Glu Phe Asp Glu Val Asp Trp Leu Glu
545                 550                 555                 560 gaa aaa tgc att gat aaa tat tac aaa act gaa tgc aaa tgt cct ttg    1728 tgg tgc ttg ttc ctt gaa aat gtt tgg tca                            1758
```

FIGURE 4

```
agcaggacta aggcagaacg cagc atg aat agt ggc cct ggc cct gta gga                    51
                          Met Asn Ser Gly Pro Gly Pro Val Gly
                           1               5 ggc agg cct ggg gga cga ggg gga cca gcc gtt cag cag aac att cct                   99
Gly Arg Pro Gly Gly Arg Gly Gly Pro Ala Val Gln Gln Asn Ile Pro
 10              15                  20                  25 tcc aac ctc ctc cag gac cat gaa aac cag aga ctc ttt gag ctt ctt                  147
Ser Asn Leu Leu Gln Asp His Glu Asn Gln Arg Leu Phe Glu Leu Leu
             30                  35                  40 ggc cga aaa tgc tgg aca ctg gct acc aca gtt gtt cag ctc tac ctg                  195
Gly Arg Lys Cys Trp Thr Leu Ala Thr Thr Val Val Gln Leu Tyr Leu
             45                  50                  55 gca ctg ccc cct gga gct gag cac tgg acc atg gaa cac tgc ggg gct                  243
Ala Leu Pro Pro Gly Ala Glu His Trp Thr Met Glu His Cys Gly Ala
             60                  65                  70 gtg tgc ttc gtc aag gat aac cct cag aag tcc tac ttc atc cgc ctt                  291
Val Cys Phe Val Lys Asp Asn Pro Gln Lys Ser Tyr Phe Ile Arg Leu
 75                  80                  85 tat gcg cta cag gct ggt cgg cta ctc tgg gaa cag gag ctg tac tct                  339
Tyr Ala Leu Gln Ala Gly Arg Leu Leu Trp Glu Gln Glu Leu Tyr Ser
 90                  95                 100                 105 cag ctg gtt tat ctc act ccc acc ccg ttc ttc cac act ttt gct gga                  387
Gln Leu Val Tyr Leu Thr Pro Thr Pro Phe Phe His Thr Phe Ala Gly
             110                 115                 120 gat gac tgt caa gta gga ctg aac ttt gcg gat gag agt gaa gcc cag                  435
Asp Asp Cys Gln Val Gly Leu Asn Phe Ala Asp Glu Ser Glu Ala Gln
             125                 130                 135 gcc ttc cgg gcc ttg gtg cag gag aag ata caa aaa agg aat cag agg                  483
Ala Phe Arg Ala Leu Val Gln Glu Lys Ile Gln Lys Arg Asn Gln Arg
     140                 145                 150 caa agc gga gaa aga cgc cag cta cca cca cca cca gca cca atc aat                  531
Gln Ser Gly Glu Arg Arg Gln Leu Pro Pro Pro Pro Ala Pro Ile Asn
 155                 160                 165 gag gag aga aga gga ggg ctc cca cct gtg ccc cca cac ccg ggt gga                  579
Glu Glu Arg Arg Gly Gly Leu Pro Pro Val Pro Pro His Pro Gly Gly
 170                 175                 180                 185 gat cat ggg ggc cca tca ggt ggt cca cta tct cta gga ctt gtg acg                  627
Asp His Gly Gly Pro Ser Gly Gly Pro Leu Ser Leu Gly Leu Val Thr
             190                 195                 200 gtc gac att cag aac cct gac atc aca agt tca cga tac cgt ggg ctc                  675
Val Asp Ile Gln Asn Pro Asp Ile Thr Ser Ser Arg Tyr Arg Gly Leu
             205                 210                 215
```

FIGURE 4 (suite 1)

```
cct gca cct ggc cct ggc cca act gat aag aaa cgc tca ggg aaa aag    723
Pro Ala Pro Gly Pro Gly Pro Thr Asp Lys Lys Arg Ser Gly Lys Lys
        220             225             230 aag atc agc aaa gct gat atc gga gca ccg agt gga ttc aaa cat gtc    771
Lys Ile Ser Lys Ala Asp Ile Gly Ala Pro Ser Gly Phe Lys His Val
    235             240             245 agc cac gtg ggc tgg gat ccc cag aat gga ttt gat gtg aac aac cta    819
Ser His Val Gly Trp Asp Pro Gln Asn Gly Phe Asp Val Asn Asn Leu
250             255             260             265 gac ccg gat ctg cgg agc ttg ttc tcc agg gca gga atc agc gag gcc    867
Asp Pro Asp Leu Arg Ser Leu Phe Ser Arg Ala Gly Ile Ser Glu Ala
            270             275             280 cag ctc act gac gca gag acc tcc aag ctc atc tac gat ttt att gag    915
Gln Leu Thr Asp Ala Glu Thr Ser Lys Leu Ile Tyr Asp Phe Ile Glu
        285             290             295 gac cag gga ggt cta gag gct gtc cgg cag gag atg agg cgc caa gag    963
Asp Gln Gly Gly Leu Glu Ala Val Arg Gln Glu Met Arg Arg Gln Glu
    300             305             310 cca ctc cca cca cct ccg ccg cca tgc aga gga gga gga gga gga gga   1011
Pro Leu Pro Pro Pro Pro Pro Cys Arg Gly Gly Gly Gly Gly Gly
315             320             325 gga gga gga gga gga gga gga gga gga gga gga ggc cag cct ctg aga   1059
Gly Gly Gly Gly Gly Gly Gly Gly Gly Gly Gly Gln Pro Leu Arg
330             335             340             345 cct cct gtt ttg ggg agt aat aag ggt cgc tca cct cca ctg ccc cct   1107
Pro Pro Val Leu Gly Ser Asn Lys Gly Arg Ser Pro Pro Leu Pro Pro
        350             355             360 gta cct atg ggg ggt gcc cca cct cca aca cca cga ggg ccc cca       1155
Val Pro Met Gly Gly Ala Pro Pro Pro Thr Pro Arg Gly Pro Pro
    365             370             375 cca cca ggc cga ggg ggt cct cct cca cca ccc cct cca gcc act gga   1203
Pro Pro Gly Arg Gly Gly Pro Pro Pro Pro Pro Pro Ala Thr Gly
        380             385             390 cga tct gga cca cca cct cct cca ctc cct gga gct ggg gga cca cca   1251
Arg Ser Gly Pro Pro Pro Pro Pro Leu Pro Gly Ala Gly Gly Pro Pro
395             400             405 gca ccg cca cca cca cca cca cca cct cca ccc tgc cct ggg            1299
Ala Pro Pro Pro Pro Pro Pro Pro Pro Pro Pro Cys Pro Gly
410             415             420             425
```

FIGURE 4 (suite 2)

```
agt gga ccc gcc cct ccc ccg ctc cct cct act cca gtg tct ggg ggg    1347
Ser Gly Pro Ala Pro Pro Pro Leu Pro Pro Thr Pro Val Ser Gly Gly
            430             435             440 agc cca gca cct ggt ggg ggc cgg ggt gca ctt ttg gac caa atc cgg    1395
Ser Pro Ala Pro Gly Gly Gly Arg Gly Ala Leu Leu Asp Gln Ile Arg
            445             450             455 cag gga att cag ctg aac aag acc cct gga gct cta gag aac tca gta    1443
Gln Gly Ile Gln Leu Asn Lys Thr Pro Gly Ala Leu Glu Asn Ser Val
            460             465             470 cag caa cca ccc gcg cag cag tca gaa ggc cta gta ggt gcc ctg atg    1491
Gln Gln Pro Pro Ala Gln Gln Ser Glu Gly Leu Val Gly Ala Leu Met
    475             480             485 cat gtc atg cag aag agg agt aga gtc atc cat tcc tca gat gaa ggg    1539
His Val Met Gln Lys Arg Ser Arg Val Ile His Ser Ser Asp Glu Gly
490             495             500             505 gag gat cag acc ggc gag gat gaa gag gat gat gaa tgg gat gac        1584
Glu Asp Gln Thr Gly Glu Asp Glu Glu Asp Asp Glu Trp Asp Asp
                510             515             520 taaagtcatc ttccttccag caagccagtt cctctccaca ctcactctgc catctagatt  1644
ctgctcccgc tggcagcttc ccaattcacc tgttggggaa cctcataccc aatctaaagt  1704
acacatgacg tcacctttca cctctcataa ctcagggatg aaacaggata aaattgagtc  1764
tatgtgtctg agtgtgtgtt cattcacatc ctaaatgagt agtttgggtt tctttccctc  1824
acagtccctt ttggctttga tcttgctttg tgtgttttta ttgagccttt cacaagtatg  1884
atctattatt cctttaagat ttcagccata gccgggtgtg gtggcgcacg cctttaattc  1944
cagcagaagg gaggcagagg caggtggatt tctgagttcg agaccagcct ggtctacaga  2004
gtgagttcca ggacagccag ggctatacag agaaaccctg tctcaaaaaa ccaaaaaaaa  2064
aaaaa                                                              2069
```

FIGURE 5

```
cggagtggga ccgagtgctc gcccaccacc agaagagacg gccctggaca ctccacccca    60
```

| | | | | | | | | | | | | | | | |
|---|---|---|---|---|---|---|---|---|---|---|---|---|---|---|---|
| ccggcgacac | c | atg | agc | tcg | ggc | cag | cag | ccc | ccg | cgg | agg | gtc | acc | aac | 110 |
| | | Met | Ser | Ser | Gly | Gln | Gln | Pro | Pro | Arg | Arg | Val | Thr | Asn | |
| | | 1 | | | 5 | | | | | 10 | | | | | |

| gtg | ggc | tcc | ctg | ctg | ctc | acc | ccg | caa | gaa | aac | gag | tct | ctt | ttc | tcc | 158 |
|---|---|---|---|---|---|---|---|---|---|---|---|---|---|---|---|---|
| Val | Gly | Ser | Leu | Leu | Leu | Thr | Pro | Gln | Glu | Asn | Glu | Ser | Leu | Phe | Ser | |
| 15 | | | | | 20 | | | | | 25 | | | | | | |

| ttc | ctc | ggc | aag | aaa | tgt | gtg | act | atg | tct | tca | gca | gtg | gtg | cag | tta | 206 |
|---|---|---|---|---|---|---|---|---|---|---|---|---|---|---|---|---|
| Phe | Leu | Gly | Lys | Lys | Cys | Val | Thr | Met | Ser | Ser | Ala | Val | Val | Gln | Leu | |
| 30 | | | | 35 | | | | | 40 | | | | | 45 | | |

| tat | gca | gct | gat | cgg | aac | tgt | atg | tgg | tca | aag | aag | tgc | agt | ggt | gtt | 254 |
|---|---|---|---|---|---|---|---|---|---|---|---|---|---|---|---|---|
| Tyr | Ala | Ala | Asp | Arg | Asn | Cys | Met | Trp | Ser | Lys | Lys | Cys | Ser | Gly | Val | |
| | | | | 50 | | | | 55 | | | | | 60 | | | |

| gct | tgt | ctt | gtt | aag | gac | aat | cct | cag | aga | tct | tat | ttt | tta | aga | ata | 302 |
|---|---|---|---|---|---|---|---|---|---|---|---|---|---|---|---|---|
| Ala | Cys | Leu | Val | Lys | Asp | Asn | Pro | Gln | Arg | Ser | Tyr | Phe | Leu | Arg | Ile | |
| | | | 65 | | | | 70 | | | | | 75 | | | | |

| ttt | gac | att | aag | gat | ggg | aaa | tta | ctg | tgg | gaa | caa | gag | cta | tac | aat | 350 |
|---|---|---|---|---|---|---|---|---|---|---|---|---|---|---|---|---|
| Phe | Asp | Ile | Lys | Asp | Gly | Lys | Leu | Leu | Trp | Glu | Gln | Glu | Leu | Tyr | Asn | |
| | | 80 | | | | 85 | | | | | 90 | | | | | |

| aac | ttt | gta | tat | aat | agt | cct | aga | gga | tat | ttt | cat | acc | ttt | gct | gga | 398 |
|---|---|---|---|---|---|---|---|---|---|---|---|---|---|---|---|---|
| Asn | Phe | Val | Tyr | Asn | Ser | Pro | Arg | Gly | Tyr | Phe | His | Thr | Phe | Ala | Gly | |
| | 95 | | | | | 100 | | | | | 105 | | | | | |

| gat | act | tgt | caa | gta | gct | ctt | aat | ttt | gcc | aat | gaa | gaa | gaa | gca | aaa | 446 |
|---|---|---|---|---|---|---|---|---|---|---|---|---|---|---|---|---|
| Asp | Thr | Cys | Gln | Val | Ala | Leu | Asn | Phe | Ala | Asn | Glu | Glu | Glu | Ala | Lys | |
| 110 | | | | 115 | | | | | 120 | | | | | 125 | | |

| aag | ttc | cga | aaa | gca | gtt | aca | gac | ctg | ttg | ggt | cga | cga | caa | agg | aaa | 494 |
|---|---|---|---|---|---|---|---|---|---|---|---|---|---|---|---|---|
| Lys | Phe | Arg | Lys | Ala | Val | Thr | Asp | Leu | Leu | Gly | Arg | Arg | Gln | Arg | Lys | |
| | | | | 130 | | | | | 135 | | | | | 140 | | |

| tct | gaa | aaa | aga | cga | gat | gct | cca | aat | ggt | ccc | aat | cta | ccc | atg | gct | 542 |
|---|---|---|---|---|---|---|---|---|---|---|---|---|---|---|---|---|
| Ser | Glu | Lys | Arg | Arg | Asp | Ala | Pro | Asn | Gly | Pro | Asn | Leu | Pro | Met | Ala | |
| | | | 145 | | | | | 150 | | | | | 155 | | | |

| aca | gtt | gac | ata | aaa | aat | cca | gaa | atc | aca | aca | aac | agg | ttt | tat | agt | 590 |
|---|---|---|---|---|---|---|---|---|---|---|---|---|---|---|---|---|
| Thr | Val | Asp | Ile | Lys | Asn | Pro | Glu | Ile | Thr | Thr | Asn | Arg | Phe | Tyr | Ser | |
| | | | 160 | | | | | 165 | | | | | 170 | | | |

| tca | caa | gtc | aac | aac | atc | tcc | cac | acc | aaa | gaa | aag | aag | aaa | gga | aaa | 638 |
|---|---|---|---|---|---|---|---|---|---|---|---|---|---|---|---|---|
| Ser | Gln | Val | Asn | Asn | Ile | Ser | His | Thr | Lys | Glu | Lys | Lys | Lys | Gly | Lys | |
| | | | 175 | | | | | 180 | | | | | 185 | | | |

| gct | aaa | aag | aag | aga | tta | acc | aag | gca | gat | att | gga | aca | cca | agt | aat | 686 |
|---|---|---|---|---|---|---|---|---|---|---|---|---|---|---|---|---|
| Ala | Lys | Lys | Lys | Arg | Leu | Thr | Lys | Ala | Asp | Ile | Gly | Thr | Pro | Ser | Asn | |
| 190 | | | | | 195 | | | | | 200 | | | | | 205 | |

FIGURE 5 (suite 1)

```
ttc cag cac att gga cat gtt ggt tgg gat cca aat aca ggt ttt gat    734
Phe Gln His Ile Gly His Val Gly Trp Asp Pro Asn Thr Gly Phe Asp
             210                 215                 220 cta aat aat ttg gat cca gaa ttg aag aat ctt ttt gat atg tgt ggg    782
Leu Asn Asn Leu Asp Pro Glu Leu Lys Asn Leu Phe Asp Met Cys Gly
             225                 230                 235 atc tct gag gcc cag ctt aaa gac aga gaa aca tca aaa gtt att tat    830
Ile Ser Glu Ala Gln Leu Lys Asp Arg Glu Thr Ser Lys Val Ile Tyr
             240                 245                 250 gac ttt att gaa aaa aca gga ggt gta gaa gct gtt aaa aat gaa ctc    878
Asp Phe Ile Glu Lys Thr Gly Gly Val Glu Ala Val Lys Asn Glu Leu
             255                 260                 265 cga agg caa gca cca cca cct cct cca ccc tca aga gga gga cct ccc    926
Arg Arg Gln Ala Pro Pro Pro Pro Pro Pro Ser Arg Gly Gly Pro Pro
270              275                 280                 285 cct cct cct ccc cct cct cac agc tca ggc cct cct ccc cct cct gcc    974
Pro Pro Pro Pro Pro Pro His Ser Ser Gly Pro Pro Pro Pro Pro Ala
             290                 295                 300 cgt gga agg ggg gct cct ccc ccg cca cca tca aga gct cct act gct   1022
Arg Gly Arg Gly Ala Pro Pro Pro Pro Pro Ser Arg Ala Pro Thr Ala
             305                 310                 315 gca cct cca cct cca cct cct tct agg cct ggt gtt gtc gtt cct cca   1070
Ala Pro Pro Pro Pro Pro Pro Ser Arg Pro Gly Val Val Val Pro Pro
             320                 325                 330 cct cct cca aac agg atg tac cct cct cca cca gcc ctg cct tcc       1118
Pro Pro Pro Asn Arg Met Tyr Pro Pro Pro Pro Ala Leu Pro Ser
             335                 340                 345 tca gca cct tca ggc cca cca cca cct ccg cct ctg tct atg gca ggg   1166
Ser Ala Pro Ser Gly Pro Pro Pro Pro Pro Pro Leu Ser Met Ala Gly
350              355                 360                 365 tcc aca gca cca cca cct cct cca cca cct ccc cct cca cca ggg cca   1214
Ser Thr Ala Pro Pro Pro Pro Pro Pro Pro Pro Pro Pro Pro Gly Pro
             370                 375                 380 cca cct ccc cct ggc ctg cct tct gat ggt gac cat caa gtt cca gct   1262
Pro Pro Pro Pro Gly Leu Pro Ser Asp Gly Asp His Gln Val Pro Ala
             385                 390                 395 tct tca gga aac aaa gca gct ctt ttg gat caa att aga gag ggt gct   1310
Ser Ser Gly Asn Lys Ala Ala Leu Leu Asp Gln Ile Arg Glu Gly Ala
             400                 405                 410 cag cta aaa aaa gtg gag cag aat agt cgg ccc gtg tcc tgc tca gga   1358
Gln Leu Lys Lys Val Glu Gln Asn Ser Arg Pro Val Ser Cys Ser Gly
             415                 420                 425
```

FIGURE 5 (suite 2)

```
agg gat gca ctt cta gac cag ata cga cag ggc att cag ttg aaa tcc    1406
Arg Asp Ala Leu Leu Asp Gln Ile Arg Gln Gly Ile Gln Leu Lys Ser
430             435                 440                 445 gtg tct gat ggc caa gag tcc aca cca cca acc ccc gcg ccc act tca    1454
Val Ser Asp Gly Gln Glu Ser Thr Pro Pro Thr Pro Ala Pro Thr Ser
                450                 455                 460 gga att gtg ggt gcg ctg atg gaa gtg atg cag aaa agg agc aaa gcc    1502
Gly Ile Val Gly Ala Leu Met Glu Val Met Gln Lys Arg Ser Lys Ala
                465                 470                 475 att cat tcc tca gat gaa gat gaa gat gat gat gat gaa gaa gat ttt    1550
Ile His Ser Ser Asp Glu Asp Glu Asp Asp Asp Asp Glu Glu Asp Phe
                480                 485                 490 cag gat gat gat gag tgg gaa gac tgatctatat tatt                    1588
Gln Asp Asp Asp Glu Trp Glu Asp
    495                 500
```

FIGURE 6

```
gccgccgaag aaggttgggg gaggagttgg gagtttagcg cagtcgccgg agtgcgagga    60
caacgaccat ccggccagag cctacccogg cgggaacggg gagcttccct ttctcacagc   120
ggcccgccgt cggctcctcc ttccgtggtc tcctccctgc gccggaggag ctgcgagatg   180
ctacgcctct gattcccctc ctcccgcccc tgtcacccag aagggaacg agcgctcgcc    240 cactcgccgg agagacggcc ctggctccct accccgccgg cgaaacc atg agc tcc    296
                                                    Met Ser Ser
                                                     1
```

| | | | | | | | | | | | | | | | | |
|---|---|---|---|---|---|---|---|---|---|---|---|---|---|---|---|---|
| ggc | cag | cag | cag | ccg | ccg | ccg | ccg | cgg | agg | gtc | acc | aac | gtg | ggg | tcc | 344 |
| Gly | Gln | Gln | Gln | Pro | Pro | Pro | Pro | Arg | Arg | Val | Thr | Asn | Val | Gly | Ser | |
| | 5 | | | | 10 | | | | | 15 | | | | | | |
| ctg | ctg | ctc | acc | ccg | cag | gag | aac | gag | tcc | ctc | ttc | acc | ttc | ctc | ggc | 392 |
| Leu | Leu | Leu | Thr | Pro | Gln | Glu | Asn | Glu | Ser | Leu | Phe | Thr | Phe | Leu | Gly | |
| 20 | | | | | 25 | | | | 30 | | | | | | 35 | |
| aag | aaa | tgt | gtg | acc | atg | tct | tcg | gca | gtg | gta | cag | tta | tat | gca | gca | 440 |
| Lys | Lys | Cys | Val | Thr | Met | Ser | Ser | Ala | Val | Val | Gln | Leu | Tyr | Ala | Ala | |
| | | | | 40 | | | | | 45 | | | | | 50 | | |
| gat | cgg | aac | tgt | atg | tgg | tca | aag | aag | tgc | agt | ggt | gtt | gct | tgt | ctt | 488 |
| Asp | Arg | Asn | Cys | Met | Trp | Ser | Lys | Lys | Cys | Ser | Gly | Val | Ala | Cys | Leu | |
| | | | 55 | | | | | 60 | | | | | 65 | | | |
| gtt | aag | gac | aat | cca | cag | aga | tct | tat | ttt | tta | aga | ata | ttt | gat | atc | 536 |
| Val | Lys | Asp | Asn | Pro | Gln | Arg | Ser | Tyr | Phe | Leu | Arg | Ile | Phe | Asp | Ile | |
| | | | 70 | | | | 75 | | | | | 80 | | | | |
| aag | gat | ggg | aaa | cta | ttg | tgg | gaa | caa | gag | cta | tac | aat | aac | ttt | gta | 584 |
| Lys | Asp | Gly | Lys | Leu | Leu | Trp | Glu | Gln | Glu | Leu | Tyr | Asn | Asn | Phe | Val | |
| | 85 | | | | | 90 | | | | | 95 | | | | | |
| tat | aat | agt | cct | aga | gga | tat | ttt | cat | acc | ttt | gct | gga | gat | acc | tgt | 632 |
| Tyr | Asn | Ser | Pro | Arg | Gly | Tyr | Phe | His | Thr | Phe | Ala | Gly | Asp | Thr | Cys | |
| 100 | | | | | 105 | | | | 110 | | | | | | 115 | |
| caa | gtt | gct | ctt | aat | ttt | gcc | aat | gaa | gaa | gaa | gca | aaa | aaa | ttc | cga | 680 |
| Gln | Val | Ala | Leu | Asn | Phe | Ala | Asn | Glu | Glu | Glu | Ala | Lys | Lys | Phe | Arg | |
| | | | | 120 | | | | | 125 | | | | | 130 | | |
| aaa | gca | gtt | aca | gac | ttg | ttg | gga | cga | cga | caa | agg | aaa | tct | gag | aaa | 728 |
| Lys | Ala | Val | Thr | Asp | Leu | Leu | Gly | Arg | Arg | Gln | Arg | Lys | Ser | Glu | Lys | |
| | | | 135 | | | | | 140 | | | | | 145 | | | |
| aga | cga | gac | ccc | cca | aat | ggt | cct | aat | cta | ccc | atg | gca | aca | gtt | gac | 776 |
| Arg | Arg | Asp | Pro | Pro | Asn | Gly | Pro | Asn | Leu | Pro | Met | Ala | Thr | Val | Asp | |
| | | 150 | | | | | 155 | | | | | 160 | | | | |
| ata | aaa | aat | cca | gaa | att | aca | aca | aat | aga | ttt | tat | ggt | ccg | caa | atc | 824 |
| Ile | Lys | Asn | Pro | Glu | Ile | Thr | Thr | Asn | Arg | Phe | Tyr | Gly | Pro | Gln | Ile | |
| 165 | | | | | 170 | | | | | 175 | | | | | | |

FIGURE 6 (suite 1)

```
aac aac atc tcc cat acc aaa gaa aag aaa aaa gga aaa gct aaa aag    872
Asn Asn Ile Ser His Thr Lys Glu Lys Lys Lys Gly Lys Ala Lys Lys
180             185             190             195 aag agg tta act aag gca gat att gga aca cca agc aat ttc caa cac    920
Lys Arg Leu Thr Lys Ala Asp Ile Gly Thr Pro Ser Asn Phe Gln His
                200             205             210 att gga cat gtg ggt tgg gat ccg aat act ggc ttt gat ctg aat aat    968
Ile Gly His Val Gly Trp Asp Pro Asn Thr Gly Phe Asp Leu Asn Asn
            215             220             225 ttg gat cca gaa ttg aag aat ctt ttt gat atg tgt gga atc tca gag    1016
Leu Asp Pro Glu Leu Lys Asn Leu Phe Asp Met Cys Gly Ile Ser Glu
        230             235             240 gca caa ctt aaa gac aga gaa aca tca aaa gtt ata tat gac ttc att    1064
Ala Gln Leu Lys Asp Arg Glu Thr Ser Lys Val Ile Tyr Asp Phe Ile
    245             250             255 gaa aaa aca gga ggt gtt gaa gct gtt aaa aat gaa ctg cga agg caa    1112
Glu Lys Thr Gly Gly Val Glu Ala Val Lys Asn Glu Leu Arg Arg Gln
260             265             270             275 gca cca cca cct cca cca cca tca agg gga ggg ccg ccc cct cct ccc    1160
Ala Pro Pro Pro Pro Pro Pro Ser Arg Gly Gly Pro Pro Pro Pro Pro
                280             285             290 ccg cct cca cat agc tcg ggc cct cct ccc cct cct gcc agg gga aga    1208
Pro Pro Pro His Ser Ser Gly Pro Pro Pro Pro Pro Ala Arg Gly Arg
            295             300             305 ggg gct cct cct cca cca cct tca aga gct ccc aca gct gca ccg cca    1256
Gly Ala Pro Pro Pro Pro Pro Ser Arg Ala Pro Thr Ala Ala Pro Pro
        310             315             320 cca ccg cct cca tcc agg cca ggt gta gga gcc cct cca cca ccg cca    1304
Pro Pro Pro Pro Ser Arg Pro Gly Val Gly Ala Pro Pro Pro Pro Pro
    325             330             335 aac agg atg tac cct cct cca ctt cca gct ctt ccc tcc tca gca cct    1352
Asn Arg Met Tyr Pro Pro Pro Leu Pro Ala Leu Pro Ser Ser Ala Pro
340             345             350             355 tca ggg cct cca cca cca cct cca cct ctg tca gtg agc ggg tca gtg    1400
Ser Gly Pro Pro Pro Pro Pro Pro Leu Ser Val Ser Gly Ser Val
                360             365             370 gca cca cca cct ccg ccg cca cct cca cct cca cca ggg cca cca cct    1448
Ala Pro Pro Pro Pro Pro Pro Pro Pro Pro Pro Gly Pro Pro Pro
            375             380             385
```

FIGURE 6 (suite 2)

```
ccc cct ggc ctc cct tct gat ggt gac cac caa gtt cca act cct gca      1496
Pro Pro Gly Leu Pro Ser Asp Gly Asp His Gln Val Pro Thr Pro Ala
        390                 395                 400 gga agc aaa gca gct ctt tta gat caa att aga gag ggt gct cag cta      1544
Gly Ser Lys Ala Ala Leu Leu Asp Gln Ile Arg Glu Gly Ala Gln Leu
    405                 410                 415 aaa aaa gtg gaa cag aac agt cgg ccg gtg tcc tgc tct gga agg gat      1592
Lys Lys Val Glu Gln Asn Ser Arg Pro Val Ser Cys Ser Gly Arg Asp
420                 425                 430                 435 gca ctt tta gac cag ata cga cag ggt att caa ctg aaa tct gta act      1640
Ala Leu Leu Asp Gln Ile Arg Gln Gly Ile Gln Leu Lys Ser Val Thr
                440                 445                 450 gat gcc cca gag tct aca cca cca gca cct gca ccc act tca gga att      1688
Asp Ala Pro Glu Ser Thr Pro Pro Ala Pro Ala Pro Thr Ser Gly Ile
                455                 460                 465 gta ggt gca tta atg gaa gtg atg cag aag agg agc aaa gcc att cat      1736
Val Gly Ala Leu Met Glu Val Met Gln Lys Arg Ser Lys Ala Ile His
        470                 475                 480 tct tca gac gaa gat gag gat gaa gat gat gat gaa gat ttt gag gat      1784
Ser Ser Asp Glu Asp Glu Asp Glu Asp Asp Asp Glu Asp Phe Glu Asp
        485                 490                 495 gat gat gaa tgg gaa gac tgatctatat attatatata tatattttta aggt        1836
Asp Asp Glu Trp Glu Asp
500                 505
```

FIGURE 7

```
agttagaaga taactcacta gacttaacac cagaaaatcc tactctgtaa taaaataatc  60
ccggggtaat ggattggatt tttctatcag gatcgtttac gtatatataa tacactgtcg 120
gagtttagcg cgcttacagc cgctacttgt ggagtccttt ttttttttt tttttttggg 180 tttcagacat ccagtaaaga atagaaacaa gcaacaaact tcagaactga aacaatgctt 240
ttttaagtta tcgcctaaat atattcaaaa aatatagata tgctagattt tcaattatac 300
caaagttcat attttcaaaa tgaatgttaa caaaagaca agttgatggc ccttttcat 360 aaagtatgcg tttagtttca agtaacgccg gctgacgtgg acgatttatc aaagaagtgg 420
ttttggaata ctcttctttt gcaattagaa aaaaggcaaa actaaatgca atgcaagcag 480
ttgcccatgg tacttgaaat tgtgtctctg gtttaaaaga tctatgatat aagtcttaac 540
tgatcttata gttgtttttt tttgaatttt ccaaatagtt tatatgatca ttgaatacgt 600
gcgagacgtc cgaaaagggg ccagtcaata cctatgaaaa aaaatcatga atatgtaata 660
ataaatattg aatgtagaat atacatagta gaaaggaag tgctgtagcg attgccatct 720
ccgctacaaa ttacagttcg ttactttaag tgttgatagg cgtgatttaa t atg gga  777
                                                           Met Gly
                                                             1
```

| | | | | | | | | | | | | | | | | |
|---|---|---|---|---|---|---|---|---|---|---|---|---|---|---|---|---|
| ctc | cta | aac | tct | tca | gat | aag | gaa | att | atc | aaa | agg | gct | cta | cca | aaa | 825 |
| Leu | Leu | Asn | Ser | Ser | Asp | Lys | Glu | Ile | Ile | Lys | Arg | Ala | Leu | Pro | Lys | |
| | 5 | | | | 10 | | | | | 15 | | | | | | |

```
gcg tcg aat aag att att gat gtt acg gtg gct cga cta tac att gca   873
Ala Ser Asn Lys Ile Ile Asp Val Thr Val Ala Arg Leu Tyr Ile Ala
         20              25              30 tac cct gat aaa aat gaa tgg cag tac act gga ctt tca gga gct ctt   921
Tyr Pro Asp Lys Asn Glu Trp Gln Tyr Thr Gly Leu Ser Gly Ala Leu
 35              40              45              50 gct cta gta gac gat ctt gtg ggg aat act ttt ttt ttg aaa tta gtt   969
Ala Leu Val Asp Asp Leu Val Gly Asn Thr Phe Phe Leu Lys Leu Val
             55              60              65 gac atc aat ggc cat aga gga gtt atc tgg gac caa gaa ttg tat gtg  1017
Asp Ile Asn Gly His Arg Gly Val Ile Trp Asp Gln Glu Leu Tyr Val
         70              75              80 aat ttt gaa tac tat caa gac cgt act ttt ttt cat aca ttt gag atg  1065
Asn Phe Glu Tyr Tyr Gln Asp Arg Thr Phe Phe His Thr Phe Glu Met
 85              90              95 gaa gaa tgc ttt gca ggt tta ttg ttt gta gat att aat gaa gca tcg  1113
Glu Glu Cys Phe Ala Gly Leu Leu Phe Val Asp Ile Asn Glu Ala Ser
100             105             110
```

FIGURE 7 (suite 1)

```
cac ttt tta aag aga gtt caa aag cgt gaa aga tat gct aac agg aaa    1161
His Phe Leu Lys Arg Val Gln Lys Arg Glu Arg Tyr Ala Asn Arg Lys
115             120             125             130 act ttg ttg aac aaa aat gct gta gca tta acc aag aaa gta aga gaa    1209
Thr Leu Leu Asn Lys Asn Ala Val Ala Leu Thr Lys Lys Val Arg Glu
                135             140             145 gaa caa aaa tct caa gtg gtg cac ggc cca aga ggg gag tca ttg att    1257
Glu Gln Lys Ser Gln Val Val His Gly Pro Arg Gly Glu Ser Leu Ile
            150             155             160 gac aat caa agg aaa aga tat aat tat gaa gat gtg gac aca att cca    1305
Asp Asn Gln Arg Lys Arg Tyr Asn Tyr Glu Asp Val Asp Thr Ile Pro
        165             170             175 act aca aag cat aag gct cct ccc cct cct ccg cca acg gcc gaa aca    1353
Thr Thr Lys His Lys Ala Pro Pro Pro Pro Pro Thr Ala Glu Thr
    180             185             190 ttt gat tca gac caa aca agt tca ttt tcc gat atc aat tcg aca aca    1401
Phe Asp Ser Asp Gln Thr Ser Ser Phe Ser Asp Ile Asn Ser Thr Thr
195             200             205             210 gca tcc gca ccg act acc cca gcc cct gct ctt cct cct gca tct cct    1449
Ala Ser Ala Pro Thr Thr Pro Ala Pro Ala Leu Pro Pro Ala Ser Pro
                215             220             225 gaa gta aga aaa gaa gaa acg cat cca aag cat agt tta ccg cct tta    1497
Glu Val Arg Lys Glu Glu Thr His Pro Lys His Ser Leu Pro Pro Leu
            230             235             240 cca aat cag ttt gcg cca tta cca gac cct cca caa cat aac tct cca    1545
Pro Asn Gln Phe Ala Pro Leu Pro Asp Pro Pro Gln His Asn Ser Pro
        245             250             255 cct caa aat aac gcg cct tcg caa ccc caa agc aat cca ttt cca ttc    1593
Pro Gln Asn Asn Ala Pro Ser Gln Pro Gln Ser Asn Pro Phe Pro Phe
    260             265             270 cca att cct gaa att ccc tcg aca cag tct gca aca aac cca ttt cca    1641
Pro Ile Pro Glu Ile Pro Ser Thr Gln Ser Ala Thr Asn Pro Phe Pro
275             280             285             290 ttt ccg gta cct cag cag cag ttt aat caa gct cct tca atg ggc ata    1689
Phe Pro Val Pro Gln Gln Gln Phe Asn Gln Ala Pro Ser Met Gly Ile
                295             300             305 cca cag cag aat agg ccc ctt cca cag ttg cct aac aga aat aat cgg    1737
Pro Gln Gln Asn Arg Pro Leu Pro Gln Leu Pro Asn Arg Asn Asn Arg
            310             315             320 cct gtg cca cct cct ccg cca atg cgt acc act act gaa ggt tca ggt    1785
Pro Val Pro Pro Pro Pro Pro Met Arg Thr Thr Thr Glu Gly Ser Gly
        325             330             335
```

FIGURE 7 (suite 2)

```
gtt cgc cta cct gct cct cca cct ccg cca agg cgt ggg cca gca cca    1833
Val Arg Leu Pro Ala Pro Pro Pro Pro Arg Arg Gly Pro Ala Pro
    340             345             350 ccg cct cca cca cat agg cac gta acc agt aat acc ctg aat tct gcc    1881
Pro Pro Pro Pro His Arg His Val Thr Ser Asn Thr Leu Asn Ser Ala
355             360             365             370 ggt gga aat agc ctc ctt cca cag gcc act gga aga aga ggg cca gca    1929
Gly Gly Asn Ser Leu Leu Pro Gln Ala Thr Gly Arg Arg Gly Pro Ala
            375             380             385 cca cca cct cct cca aga gca tct cgc ccc aca cca aac gtt acg atg    1977
Pro Pro Pro Pro Pro Arg Ala Ser Arg Pro Thr Pro Asn Val Thr Met
        390             395             400 caa caa aat cca caa cag tac aat aat tct aac cgc ccc ttt gga tat    2025
Gln Gln Asn Pro Gln Gln Tyr Asn Asn Ser Asn Arg Pro Phe Gly Tyr
    405             410             415 cag aca aat agc aac atg tca tct cca ccc cct cct cca gtg aca act    2073
Gln Thr Asn Ser Asn Met Ser Ser Pro Pro Pro Pro Pro Val Thr Thr
420             425             430 ttc aat acc ctg aca cca caa atg act gca gca act gga caa cct gca    2121
Phe Asn Thr Leu Thr Pro Gln Met Thr Ala Ala Thr Gly Gln Pro Ala
435             440             445             450 gtt ccc ctt cct cag aat act caa gca cct tcg caa gcc aca aat gtg    2169
Val Pro Leu Pro Gln Asn Thr Gln Ala Pro Ser Gln Ala Thr Asn Val
            455             460             465 cca gtg gca cca cca cct cct ccg gca tct tta ggc cag tcg cag ata    2217
Pro Val Ala Pro Pro Pro Pro Pro Ala Ser Leu Gly Gln Ser Gln Ile
        470             475             480 cct cag tca gca ccc tca gca cct att ccg cca acg tta cca tcg acg    2265
Pro Gln Ser Ala Pro Ser Ala Pro Ile Pro Pro Thr Leu Pro Ser Thr
    485             490             495 acg agt gct gca cca cct ccg cca cca gca ttc cta act caa caa cct    2313
Thr Ser Ala Ala Pro Pro Pro Pro Pro Ala Phe Leu Thr Gln Gln Pro
500             505             510 caa tct gga gga gct cca gct cca ccc cca cct cct caa atg cca gct    2361
Gln Ser Gly Gly Ala Pro Ala Pro Pro Pro Pro Gln Met Pro Ala
515             520             525             530 aca tca aca tcc gga ggc ggt tca ttc gct gaa act act gga gat gca    2409
Thr Ser Thr Ser Gly Gly Gly Ser Phe Ala Glu Thr Thr Gly Asp Ala
            535             540             545 ggt cgt gat gca ctt tta gct tca att aga ggg gca ggt ggc ata ggc    2457
Gly Arg Asp Ala Leu Leu Ala Ser Ile Arg Gly Ala Gly Gly Ile Gly
        550             555             560
```

FIGURE 7 (suite 3)

```
gct ttg aga aaa gtt gac aaa tcg cag cta gat aag ccc tca gtt tta    2505
Ala Leu Arg Lys Val Asp Lys Ser Gln Leu Asp Lys Pro Ser Val Leu
        565                 570                 575 ctg cag gaa gca cgt gga gaa tct gct tca cca cca gca gcg gct gga    2553
Leu Gln Glu Ala Arg Gly Glu Ser Ala Ser Pro Pro Ala Ala Ala Gly
        580                 585                 590 aat gga ggc aca cct ggt gga cct ccg gct tct tta gca gat gcg ttg    2601
Asn Gly Gly Thr Pro Gly Gly Pro Pro Ala Ser Leu Ala Asp Ala Leu
595                 600                 605                 610 gca gca gct tta aac aaa aga aaa act aaa gtg gga gct cat gac gat    2649
Ala Ala Ala Leu Asn Lys Arg Lys Thr Lys Val Gly Ala His Asp Asp
                615                 620                 625 atg gac aat ggt gat gat tgg taatggaatg caaacaaaga tgaaactact       2700
Met Asp Asn Gly Asp Asp Trp
                630 gttatagaaa atatgtaatt ttatgtactc actattaatg atcaaagtaa ttgctctttt  2760 tatgtatagt ttctttaatc ggaggaaatt tgatatagg ttcaaaggcg gtcagtgatt   2820 gaatgatcaa ggtaatagtc gggctacaat gatggccatc cctatggccg tttcaaatgt  2880 ttgagaaaat gatgtatagt aaatcctaga ttttagcagt tcgaatcaaa aacccatgta  2940 aaagggtaa atatttccta attataatat ttttgtttaa ttacacatgt agaacaataa   3000 aagtatagaa ttttagatag tat                                          3023
```

FIGURE 8

```
ttctaataat taatgattat gattaagtca ttttttaat aatcttataa taaactaaca 60
ttatgagaca agcaaacttc gtatggttga ataaatttta tttacctctt tacaatgagg 120
acgataagta tgtagaatgt aaaaaatatt aaacccgaat taatgtctca agttttatta 180
atctataaac agttaatata attagcaaaa tttaccagct gctaataagt gcgttgcaaa 240
tttttatagt acatagcgta gtatagtata gtatactaca ctaattatca ctcattggct 300
tgttaactac agtgaaaatg ctaacaaacg ggaggaacca aaacaccact tataccactg 360
```

```
tgagacagca attttttgaat tgcattacaa tccgaaaatt caa atg cct cca tct    415
                                              Met Pro Pro Ser
                                               1 tcc tct ata act caa gag gat aag gca act atc cgt aaa tac ata cct    463
Ser Ser Ile Thr Gln Glu Asp Lys Ala Thr Ile Arg Lys Tyr Ile Pro
 5              10                  15                      20 aaa agc aca aat aaa atc att gca gca gcc gtc gtc aag cta tat gta    511
Lys Ser Thr Asn Lys Ile Ile Ala Ala Ala Val Val Lys Leu Tyr Val
                 25                  30                      35 gct tat cct gat ccg aac aaa tgg aat tat aca ggt ctt tgt ggt gct    559
Ala Tyr Pro Asp Pro Asn Lys Trp Asn Tyr Thr Gly Leu Cys Gly Ala
             40                  45                      50 ctt gta ttg tcc tat gat aca aca gca aaa tgc tgt tgg ttt aaa ctg    607
Leu Val Leu Ser Tyr Asp Thr Thr Ala Lys Cys Cys Trp Phe Lys Leu
         55                  60                      65 gtt gac gtt gtg aat aat agt ggt ata ata tgg gac caa gag ctt tat    655
Val Asp Val Val Asn Asn Ser Gly Ile Ile Trp Asp Gln Glu Leu Tyr
     70                  75                      80 caa aat atg gac tat cgc caa gat cgt aca ttt ttt cat tct ttc gag    703
Gln Asn Met Asp Tyr Arg Gln Asp Arg Thr Phe Phe His Ser Phe Glu
 85                  90                      95                  100 ctt gat aaa tgc cta gca ggt ttt agt ttt gca aac gag aca gac gct    751
Leu Asp Lys Cys Leu Ala Gly Phe Ser Phe Ala Asn Glu Thr Asp Ala
                 105                 110                     115 caa aaa ttt tac aaa aag gtt tta gat aaa ggt tgc cat cct gaa tca    799
Gln Lys Phe Tyr Lys Lys Val Leu Asp Lys Gly Cys His Pro Glu Ser
             120                 125                     130 att gag aat ccg gtt ttg tca ttt att acc aga aaa ggt tct tct aga    847
Ile Glu Asn Pro Val Leu Ser Phe Ile Thr Arg Lys Gly Ser Ser Arg
         135                 140                     145 cat gcg cct aac aac agc aat atc caa cct ccc tca gct gct cct cct    895
His Ala Pro Asn Asn Ser Asn Ile Gln Pro Pro Ser Ala Ala Pro Pro
     150                 155                     160
```

FIGURE 8 (suite 1)

```
gta cct gga aag gaa aat tat aat gct gtt gga tct aaa agt ccc aat    943
Val Pro Gly Lys Glu Asn Tyr Asn Ala Val Gly Ser Lys Ser Pro Asn
165             170             175             180 gag ccc gag ctt tta aat tcg ctt gat ccg agc tta att gat tct cta    991
Glu Pro Glu Leu Leu Asn Ser Leu Asp Pro Ser Leu Ile Asp Ser Leu
                185             190             195 atg aag atg ggc att tcc cag gat caa att gct gaa aac gca gat ttc   1039
Met Lys Met Gly Ile Ser Gln Asp Gln Ile Ala Glu Asn Ala Asp Phe
            200             205             210 gtc aaa gcg tac ctt aat gaa tca gct ggt aca cct acc agt act tct   1087
Val Lys Ala Tyr Leu Asn Glu Ser Ala Gly Thr Pro Thr Ser Thr Ser
        215             220             225 gca cct ccc atc cct cca agc att cct tcc tct cgt ccc cca gag cgt   1135
Ala Pro Pro Ile Pro Pro Ser Ile Pro Ser Ser Arg Pro Pro Glu Arg
    230             235             240 gtt cct tct gtg tct gca cct gct cct ccc cca att cca cct cca tct   1183
Val Pro Ser Val Ser Ala Pro Ala Pro Pro Pro Ile Pro Pro Pro Ser
245             250             255             260 aat gga act gtc tct tct cct cct aac tcc cct ccc cgt cct atc gct   1231
Asn Gly Thr Val Ser Ser Pro Pro Asn Ser Pro Pro Arg Pro Ile Ala
                265             270             275 cct gtt tcg atg aat cct gct att aat tcc acc tcg aaa cct cca ctc   1279
Pro Val Ser Met Asn Pro Ala Ile Asn Ser Thr Ser Lys Pro Pro Leu
            280             285             290 cct cca cca tct tca aga gtc agt gcg gca gct cta gct gct aac aaa   1327
Pro Pro Pro Ser Ser Arg Val Ser Ala Ala Ala Leu Ala Ala Asn Lys
        295             300             305 aaa cga cct cct ccg cct ccg cct cca tcc cgt cgt aat cgt ggt aaa   1375
Lys Arg Pro Pro Pro Pro Pro Pro Ser Arg Arg Asn Arg Gly Lys
    310             315             320 cca ccg att ggt aat ggt tct tct aac tcg tct ctt cct cca cct cca   1423
Pro Pro Ile Gly Asn Gly Ser Ser Asn Ser Ser Leu Pro Pro Pro Pro
325             330             335             340 cca cct cct aga tct aat gct gct ggc tca att cct ttg ccg cct caa   1471
Pro Pro Pro Arg Ser Asn Ala Ala Gly Ser Ile Pro Leu Pro Pro Gln
                345             350             355 ggt aga tct gct cct cct cca cct cct cca agg tct gct cct tcc act   1519
Gly Arg Ser Ala Pro Pro Pro Pro Pro Arg Ser Ala Pro Ser Thr
            360             365             370 ggg aga caa cca ccc cct tta tct tca tct cgt gca gtt tca aac cca   1567
Gly Arg Gln Pro Pro Pro Leu Ser Ser Ser Arg Ala Val Ser Asn Pro
        375             380             385
```

FIGURE 8 (suite 2)

```
cca gcc cct cct cca gct att cct ggt cgt tct gcg cct gca ctt ccc      1615
Pro Ala Pro Pro Pro Ala Ile Pro Gly Arg Ser Ala Pro Ala Leu Pro
    390                 395                 400 cct ctt ggt aat gca tca cga aca agc aca cct cct gtc cct aca cct      1663
Pro Leu Gly Asn Ala Ser Arg Thr Ser Thr Pro Pro Val Pro Thr Pro
405                 410                 415                 420 cct tct ctt cct cct agt gca cct cca tct ttg ccc ccc agt gca cca      1711
Pro Ser Leu Pro Pro Ser Ala Pro Pro Ser Leu Pro Pro Ser Ala Pro
                425                 430                 435 cct tct cta cct atg ggc gca cca gct gct ccc ccc cta cca cct agt      1759
Pro Ser Leu Pro Met Gly Ala Pro Ala Ala Pro Pro Leu Pro Pro Ser
            440                 445                 450 gca cca att gct cct cct cta ccc gct ggt atg cca gct gct cca cca      1807
Ala Pro Ile Ala Pro Pro Leu Pro Ala Gly Met Pro Ala Ala Pro Pro
        455                 460                 465 ttg cct ccc gct gca cca gct cct cct cca gct cca gct cct gcg ccc      1855
Leu Pro Pro Ala Ala Pro Ala Pro Pro Pro Ala Pro Ala Pro Ala Pro
470                 475                 480 gcc gcg cct gtt gct tcg ata gct gaa ttg cct caa caa gac ggc cgt      1903
Ala Ala Pro Val Ala Ser Ile Ala Glu Leu Pro Gln Gln Asp Gly Arg
485                 490                 495                 500 gct aat tta atg gcc agt atc aga gcc agc ggt ggt atg gat tta ctg      1951
Ala Asn Leu Met Ala Ser Ile Arg Ala Ser Gly Gly Met Asp Leu Leu
            505                 510                 515 aaa agc agg aaa gta tct gct tct cct agt gtc gca tct aca aaa act      1999
Lys Ser Arg Lys Val Ser Ala Ser Pro Ser Val Ala Ser Thr Lys Thr
        520                 525                 530 tcg aat cct ccg gta gaa gca ccc cct tct aac aat ctt atg gat gca      2047
Ser Asn Pro Pro Val Glu Ala Pro Pro Ser Asn Asn Leu Met Asp Ala
    535                 540                 545 ttg gca agc gct ttg aac caa cgt aaa acc aaa gtc gct cag agt gac      2095
Leu Ala Ser Ala Leu Asn Gln Arg Lys Thr Lys Val Ala Gln Ser Asp
550                 555                 560 gaa gag gat gaa gac gac gat gag tgg gac tagttattaa tatctttgaa       2145
Glu Glu Asp Glu Asp Asp Asp Glu Trp Asp
565                 570 attacctata cttttttgat tcacacagtc ttttaaagtt ttgttaaacg acttcactat   2205
ttttatttgg atttgtgttt attgtattag agcaaacacc atttattcta aattgaataa   2265
cgcgaatttg tgttgatatt actattcata tatcgcaaca cagtgtgtat ctttacttta   2325
ttgtaagtat gggagcagtc acacatttcg gtaccacaac tttagaaacg tcaagttcaa   2385
```

FIGURE 8 (suite 3)

```
gtccttccac aaccaaaaac gtttggtcaa atagaaacaa atggatcctc tagagtcgac 2445 ctgcagcaa                                                        2454
```

WASP FAMILY PROTEIN FRAGMENTS, AND USE THEREOF

The invention concerns peptide fragments of WASP family proteins or peptides derived from these fragments, and uses thereof in particular within the context of molecule detection processes having an effect on cellular motility.

The cells of our body are capable of moving and they sometimes become round and divide into two sister cells. All these movements are based on the actin cytoskeleton. At a multicellular stage, the cytoskeleton plays an essential role in the organization of the body and homeostasis. For example, cellular migration is essential in embryogenesis and the immune response, as well as in the healing of wounds, where the cells migrate to the damaged regions. These movements are dependent on the normal functioning of the actin cytoskeleton. The consequences of disturbing the functioning of the cytoskeleton can be disastrous to the organism. In metastatic processes, for example, the cytoskeleton's lack of control over tumorous cells can cause them to migrate outside their normal location, allowing them to proliferate in other parts of the body, which makes treatment of the cancer extremely difficult.

The characterisation of proteins capable of polymerising actin and the understanding of the mechanism whereby this polymerisation generates a force, represent the key elements in understanding the functioning of the cytoskeleton in the cell. However, the dynamic properties of the cytoskeleton make it extremely difficult to study. Moreover, the approaches currently available for analysing the cytoskeleton are complicated or tedious.

The first stage in all the processes dependent on the cytoskeleton, such as movement, is the production of filaments of actin, or F-actin. The mechanism of the formation of these biological polymers in the cell is still not known, despite the identification of numerous actin-binding proteins, and the extensive study of actin polymerisation in vitro.

Wiskott-Aldrich syndrome is a disease of the cytoskeleton. Human WASP protein, expressed on the basis of the WAS gene which is mutated in patients affected by this syndrome, and likewise N-WASP protein of bovine origin (which is approx. 45% identical in sequence with human WASP protein) have thus been the subject of investigations aimed at explaining the mechanism of the functioning of the cytoskeleton in the cell (Yarar et al., Current Biology, 9: 555–558 (1999); Rohatgi et al., Cell, 97: 221–231 (1999); Miki et al., The EMBO Journal, 15(19): 5326–5335 (1996)).

These WASP and N-WASP proteins are made up of peptide domains having functional properties which are identifiable in biochemical tests. Thus, these two proteins mainly possess the following domains:
- a plekstrin homology domain which binds to phosphatidylinositol (4,5) biphosphate, the latter itself binding to proteins involved in the formation of actin filaments,
- a Cdc42 binding domain, a protein with GTPase activity inducing actin polymerisation, and hence regulating the cytoskeleton,
- a prolin-rich region,
- a verprolin homology domain, a protein also binding to proteins involved in the formation of actin filaments, said domain comprising a verprolin-homologous sequence in the case of human WASP, and two verprolin-homologous sequences in the case of N-WASP,
- a cofilin homology domain, an actin-binding protein, having an actin-depolymerisation activity dependent on the pH,
- a C-terminal acid segment.

Moreover, it has been shown that these WASP and N-WASP proteins interact with the Arp2/3 complex (a proteinic complex involved in actin polymerisation) and thus induce actin polymerisation.

On this basis, it has been demonstrated that WASP protein is sufficient to act on cellular motility based on actin, and that this function is dependent on the Arp2/3 complex (Yarar et al. 1999, mentioned above). To demonstrate this, the authors of this article prepared microspheres covered with WASP protein and demonstrated that these microspheres polymerise actin, form actin tails, and are endowed with motility based on the actin in the cellular extracts. In cellular extracts in which the Arp2/3 complex has been eliminated, the microspheres covered with WASP protein no longer have any motility and only possess a residual actin polymerisation activity.

With regard to N-WASP protein, it has been demonstrated that the C-terminal part of N-WASP, i.e. the C-terminal fragment of 114 amino acids comprising the verprolin homology domain (V region containing the two verprolin homologous sequences), the cofilin homology domain (C region) and the C-terminal acid segment (A region), or VCA fragment, binds to the Arp2/3 complex and strongly stimulates the latter's capacity to nucleate actin polymerisation (Rohatgi et al. 1999, above-mentioned).

According to recent studies, whole WASP and N-WASP proteins would be required for cellular motility dependent on actin, to the extent that, not only does the C-terminal part of these proteins interact with actin, but also the N-terminal part which keeps the actin filament in the process of formation in proximity to the cellular surface (Loisel et al., Nature, 401: 613–616 (1999); Egile et al., The Journal of Cell Biology, 145: 1319–1332 (1999)).

The invention follows on from the highlighting by the Inventors of the fact that, contrary to what might be supposed from the prior art described above, fragments of these WASP and N-WASP proteins are sufficient to induce actin polymerisation as this allows the movement of the supports to which said fragments are bound in cellular extracts.

The invention aims to provide new fragments, or polypeptides derived from WASP and N-WASP proteins, as well as nucleotide sequences coding for these fragments.

The invention also aims to provide new molecule detection or screening processes having an effect on the formation of the cytoskeleton, in particular cytotoxic molecules or medicaments which can be used within the context of treatment of pathologies linked to abnormal development of the cytoskeleton.

The invention also aims to provide new reagents and kits for implementation of the above-mentioned processes.

The invention also concerns the use:
- of peptide fragments of WASP family proteins in eukaryotic cells, in particular in cells of humans or other mammals, or cells of insects or of micro-organisms such as yeasts, said peptide fragments having the property of WASP family proteins to polymerise actin, inducing cellular motility,
- or peptide sequences derived from the above-mentioned peptide fragments of WASP family proteins, in particular by substitution of one or more amino acids of these fragments, said derived sequences having the above-mentioned property of WASP family proteins and said fragments thereof, for the preparation of reagents which can be used within the framework of implementation of a process for the detection or screening of molecules having an inhibiting or stimulating effect on the formation of the actin cytoskeleton, and hence an inhibiting or stimulating effect on cellular motility.

The term "actin polymerisation property inducing cellular motility" above and below means the property of WASP family proteins, or fragments or sequences derived from these, to polymerise actin, inducing the movement of cells of the organism, or of appropriate supports, such as the microspheres described below, in vivo or in vitro.

The invention also concerns the use of the above-mentioned peptide fragments or derived sequences, within the context of implementation of a process for the detection or screening of molecules capable of being used as medicaments in the treatment of pathologies linked to a dysfunction of the actin polymerisation process within the context of formation of the actin cytoskeleton.

The invention concerns more particularly the use of above-mentioned peptide fragments or derived sequences, within the context of implementation of a process for the detection or screening of molecules having an inhibiting effect on the formation of the actin cytoskeleton, and thus an inhibiting effect on cellular motility, said molecules being capable of being used:

as medicaments in the treatment of metastatic cancers, or as anti-parasitic antibiotics.

The invention concerns more particularly the use of above-mentioned peptide fragments or derived sequences, within the context of implementation of a process for the detection of secondary effects of molecules, in particular of medicaments or molecules from the environment, i.e. a process for the detection of molecules capable of having a cytotoxic effect corresponding to inhibition or stimulation of the formation of the actin cytoskeleton.

The term "WASP family proteins" above and below means the protein produced by the WAS gene, mutated within the context of Wiskott-Aldrich syndrome in humans, as well as proteins which may or may not be of human origin, having at least approx. 45% homology with the above-mentioned human WASP protein, and being involved in the cellular actin polymerisation process, and, possibly, in cellular motility.

The above-mentioned WASP family proteins also possess the common characteristic of possessing at least three major domains:

a WH1/Scar domain in the N-terminal part; this domain has structural characteristics similar to a plekstrin homology domain (or pH domain), and is supposed to interact with polymerised actin and with phospholipids, a prolin rich domain, a WH2/A domain which is divided into three sub-domains, i.e. the above-mentioned verprolin homology sub-domain, cofilin homology sub-domain and acid sub-domain.

Advantageously, the peptide fragments used within the context of the present invention are chosen from WASP, N-WASP, Scar and Las protein fragments, or peptide sequences derived from the above-mentioned peptide fragments as defined above.

The invention concerns more particularly the above-mentioned use of peptide fragments chosen from fragments:

of human or other mammalian WASP protein, in particular bovine or murine WASP protein, of human or other mammalian N-WASP protein, in particular bovine or rat N-WASP protein, of Scar sub-family proteins, such as Scar1/WAVE protein of *Dictyostellium discoideum*, or of *Caenorhabditis elegans*, or of *Drosophila melanogaster*, of mice or of humans.

of proteins of the Las sub-family of micro-organisms, in particular yeasts such as the LAS17/Bee1 protein of *Saccharomyces cerevisiae* or the WASP homologous protein (Wsp1p) of *Schizosaccharomyces pombe*.

Advantageously, the above-mentioned peptide fragments are chosen from those including:

the verprolin homology domain contained in WASP family proteins, or in a protein derived from these, or at least one of the two verprolin homologous sequences when said WASP family proteins contain two of these sequences, or a peptide sequence derived from the above-mentioned domain, in particular by substitution, addition or removal of one or more amino acids, and retaining the property of this domain to bind to actin, and the cofilin homology domain contained in WASP family proteins, or in a protein derived from these, or a peptide sequence derived from the above-mentioned domain, in particular by substitution, addition or removal of one or more amino acids, and retaining the property of this domain to intervene in actin polymerisation.

The above-mentioned peptide fragments used within the framework of the present invention possibly also contain the C-terminal acid segment of said WASP proteins or derivatives.

BRIEF DESCRIPTION OF THE DRAWINGS

FIG. 1 represents the peptide sequence of a human WASP protein (SEQ ID NO: 2).

FIG. 2 represents the peptide sequence of a human N-WASP protein (SEQ ID NO: 12).

FIG. 3 represents the peptide sequence of a human Scar 1 protein (SEQ ID NO: 26).

FIG. 4 represents a peptide sequence of a murine WASP protein (SEQ ID NO: 36).

FIG. 5 represents a peptide sequence of a N-WASP protein (SEQ ID NO: 46).

FIG. 6 represents bovine N-WASP protein (SEQ ID NO: 56).

FIG. 7 represents a peptide sequence of a LAS 17 protein (SEQ ID NO: 66).

FIG. 8 represents a WASP homologous protein of *Schizosaccharomyces pombe* (SEQ ID NO: 76).

Advantageously, the above-mentioned peptide fragments do not contain the plekstrin homology domain, and/or the Cdc42 binding domain, and/or the prolin-rich region, defined above, of said WASP family proteins.

The invention concerns more particularly the above-mentioned use of peptide fragments of WASP family proteins of human origin.

Advantageously, the peptide fragments of WASP family proteins of human origin used are chosen from fragments of human WASP protein including:

the verprolin homology domain delimited by the amino acids situated at positions 430 and 446 of the peptide sequence SEQ ID NO: 2 of human WASP protein represented in FIG. 1, or a peptide sequence derived from the above-mentioned domain as defined above.

and the cofilin homology domain delimited by the amino acids situated at positions 469 and 487 of the peptide sequence SEQ ID NO: 2 of human WASP protein represented in FIG. 1, or a peptide sequence derived from the above-mentioned domain as defined above.

Preferably, the above-mentioned fragments of human WASP protein used are chosen from the following:

fragments of which the N-terminal amino acid corresponds to that situated at one of positions 404 to 430 in FIG. 1, and the C-terminal amino acid corresponds to that situated at one of positions 487 to 502 in FIG. 1, the fragment of 99 amino acids delimited by the amino acids situated at positions 404 and 502 in FIG. 1, i.e. the following SEQ ID NO: 4 peptide:

```
Pro Ser Ser Gly Asn Gly Pro Ala Pro Pro Leu Pro Pro Ala Leu
Val Pro Ala Gly Gly Leu Ala Pro Gly Gly Gly Arg Gly Ala Leu Leu
Asp Gln Ile Arg Gln Gly Ile Gln Leu Asn Lys Thr Pro Gly Ala Pro
Glu Ser Ser Ala Leu Gln Pro Pro Pro Gln Ser Ser Glu Gly Leu Val
Gly Ala Leu Met His Val Met Gln Lys Arg Ser Arg Ala Ile His Ser
Ser Asp Glu Gly Glu Asp Gln Ala Gly Asp Glu Asp Glu Asp Asp Glu
Trp Asp Asp
``` the fragment of 84 amino acids delimited by the amino acids situated at positions 404 and 487 in FIG. 1, i.e. the following SEQ ID NO: 6 peptide:

```
Pro Ser Ser Gly Asn Gly Pro Ala Pro Pro Leu Pro Pro Ala Leu
Val Pro Ala Gly Gly Leu Ala Pro Gly Gly Gly Arg Gly Ala Leu Leu
Asp Gln Ile Arg Gln Gly Ile Gln Leu Asn Lys Thr Pro Gly Ala Pro
Glu Ser Ser Ala Leu Gln Pro Pro Pro Gln Ser Ser Glu Gly Leu Val
Gly Ala Leu Met His Val Met Gln Lys Arg Ser Arg Ala Ile His Ser
Ser Asp Glu Gly
``` the fragment of 73 amino acids delimited by the amino acids situated at positions 430 and 502 in FIG. 1, i.e. the following SEQ ID NO: 8 peptide:

```
Gly Arg Gly Ala Leu Leu Asp Gln Ile Arg Gln Gly Ile Gln Leu Asn
Lys Thr Pro Gly Ala Pro Glu Ser Ser Ala Leu Gln Pro Pro Pro Gln
Ser Ser Glu Gly Leu Val Gly Ala Leu Met His Val Met Gln Lys Arg
Ser Arg Ala Ile His Ser Ser Asp Glu Gly Glu Asp Gln Ala Gly Asp
Glu Asp Glu Asp Asp Glu Trp Asp Asp
``` the fragment of 58 amino acids delimited by the amino acids situated at positions 430 and 487 in FIG. 1, i.e. the following SEQ ID NO: 10 peptide:

```
Gly Arg Gly Ala Leu Leu Asp Gln Ile Arg Gln Gly Ile Gln Leu Asn
Lys Thr Pro Gly Ala Pro Glu Ser Ser Ala Leu Gln Pro Pro Pro Gln
Ser Ser Glu Gly Leu Val Gly Ala Leu Met His Val Met Gln Lys Arg
Ser Arg Ala Ile His Ser Ser Asp Glu Gly
``` or the peptide sequences derived from the above-mentioned peptide fragments, in particular by substitution, addition or removal of one or more amino acids of these fragments, said derived sequences having the property defined above, of WASP family proteins and said fragments thereof.

Advantageously, the peptide fragments of WASP family proteins of human origin used are chosen from the fragments of human N-WASP protein including:

the verprolin homologous sequence delimited by the amino acids situated at positions 405 and 421 of the peptide sequence SEQ ID NO: 12 of human N-WASP protein represented in FIG. 2, or a peptide sequence derived from the above-mentioned domain as defined above, and/or the verprolin homologous sequence delimited by the amino acids situated at positions 433 and 449 of the peptide sequence SEQ ID NO: 12 of human N-WASP protein represented in FIG. 2, or a peptide sequence derived from the above-mentioned domain as defined above, and the cofilin homology domain contained in the above-mentioned N-WASP protein, i.e. the domain delimited by the amino acids situated at positions 470 and 488 of the peptide sequence SEQ ID NO: 12 of human N-WASP protein represented in FIG. 2, or a peptide sequence derived from the above-mentioned domain as defined above.

Preferably, the above-mentioned fragments of the human N-WASP protein used are chosen from the following:

fragments of which the N-terminal amino acid corresponds to that situated at one of positions 392 to 433 in FIG. 2, and the C-terminal amino acid corresponds to that situated at one of positions 488 to 505 in FIG. 2, the fragment of 114 amino acids delimited by the amino acids situated at positions 392 and 505 in FIG. 2, i.e. the following SEQ ID NO: 14 peptide:

Pro Ser Asp Gly Asp His Gln Val Pro Thr Thr Ala Gly Asn Lys Ala

Ala Leu Leu Asp Gln Ile Arg Glu Gly Ala Gln Leu Lys Lys Val Glu

Gln Asn Ser Arg Pro Val Ser Cys Ser Gly Arg Asp Ala Leu Leu Asp

Gln Ile Arg Gln Gly Ile Gln Leu Lys Ser Val Ala Asp Gly Gln Glu

Ser Thr Pro Pro Thr Pro Ala Pro Thr Ser Gly Ile Val Gly Ala Leu

Met Glu Val Met Gln Lys Arg Ser Lys Ala Ile His Ser Ser Asp Glu

Asp Glu Asp Glu Asp Asp Glu Glu Asp Phe Glu Asp Asp Asp Glu Trp

Glu Asp the fragment of 97 amino acids delimited by the amino acids situated at positions 392 and 488 in FIG. 2, i.e. the following SEQ ID NO: 16 peptide:

Pro Ser Asp Gly Asp His Gln Val Pro Thr Thr Ala Gly Asn Lys Ala

Ala Leu Leu Asp Gln Ile Arg Glu Gly Ala Gln Leu Lys Lys Val Glu

Gln Asn Ser Arg Pro Val Ser Cys Ser Gly Arg Asp Ala Leu Leu Asp

Gln Ile Arg Gln Gly Ile Gln Leu Lys Ser Val Ala Asp Gly Gln Glu

Ser Thr Pro Pro Thr Pro Ala Pro Thr Ser Gly Ile Val Gly Ala Leu

Met Glu Val Met Gln Lys Arg Ser Lys Ala Ile His Ser Ser Asp Glu

Asp the fragment of 101 amino acids delimited by the amino acids situated at positions 405 and 505 in FIG. 2, i.e. the following SEQ ID NO: 18 peptide:

Asn Lys Ala Ala Leu Leu Asp Gln Ile Arg Glu Gly Ala Gln Leu Lys

Lys Val Glu Gln Asn Ser Arg Pro Val Ser Cys Ser Gly Arg Asp Ala

Leu Leu Asp Gln Ile Arg Gln Gly Ile Gln Leu Lys Ser Val Ala Asp

Gly Gln Glu Ser Thr Pro Pro Thr Pro Ala Pro Thr Ser Gly Ile Val

Gly Ala Leu Met Glu Val Met Gln Lys Arg Ser Lys Ala Ile His Ser

Ser Asp Glu Asp Glu Asp Glu Asp Asp Glu Glu Asp Phe Glu Asp Asp

Asp Glu Trp Glu Asp the fragment of 84 amino acids delimited by the amino acids situated at positions 405 and 488 in FIG. 2, i.e. the following SEQ ID NO: 20 peptide:

Asn Lys Ala Ala Leu Leu Asp Gln Ile Arg Glu Gly Ala Gln Leu Lys

Lys Val Glu Gln Asn Ser Arg Pro Val Ser Cys Ser Gly Arg Asp Ala

Leu Leu Asp Gln Ile Arg Gln Gly Ile Gln Leu Lys Ser Val Ala Asp

Gly Gln Glu Ser Thr Pro Pro Thr Pro Ala Pro Thr Ser Gly Ile Val

Gly Ala Leu Met Glu Val Met Gln Lys Arg Ser Lys Ala Ile His Ser

Ser Asp Glu Asp the fragment of 73 amino acids delimited by the amino acids situated at positions 433 and 505 in FIG. 2, i.e. the following SEQ ID NO: 22 peptide:

Gly Arg Asp Ala Leu Leu Asp Gln Ile Arg Gln Gly Ile Gln Leu Lys

Ser Val Ala Asp Gly Gln Glu Ser Thr Pro Pro Thr Pro Ala Pro Thr

Ser Gly Ile Val Gly Ala Leu Met Glu Val Met Gln Lys Arg Ser Lys

Ala Ile His Ser Ser Asp Glu Asp Glu Asp Glu Asp Asp Glu Glu Asp

Phe Glu Asp Asp Asp Glu Trp Glu Asp the fragment of 56 amino acids delimited by the amino acids situated at positions 433 and 488 in FIG. 2, i.e. the following SEQ ID NO: 24 peptide:

Gly Arg Asp Ala Leu Leu Asp Gln Ile Arg Gln Gly Ile Gln Leu Lys

Ser Val Ala Asp Gly Gln Glu Ser Thr Pro Pro Thr Pro Ala Pro Thr

Ser Gly Ile Val Gly Ala Leu Met Glu Val Met Gln Lys Arg Ser Lys

Ala Ile His Ser Ser Asp Glu Asp or the peptide sequences derived from the above-mentioned peptide fragments, in particular by substitution, addition or removal of one or more amino acids of these fragments, said derived sequences having the property defined above, of WASP family proteins and said fragments thereof.

Advantageously, the peptide fragments of WASP family proteins of human origin used are chosen from the fragments of human Scar1 protein including:
the verprolin homology domain delimited by the amino acids situated at positions 497 and 513 of the peptide sequence SEQ ID NO: 26 of human Scar1 protein represented in FIG. 3, or a peptide sequence derived from the above-mentioned domain as defined above,
and the cofilin homology domain delimited by the amino acids situated at positions 531 and 546 of the peptide sequence SEQ ID NO: 26 of human Scar1 protein represented in FIG. 3, or a peptide sequence derived from the above-mentioned domain as defined above.

Preferably, the above-mentioned human Scar1 protein fragments used are chosen from the following:
fragments of which the N-terminal amino acid corresponds to that situated at one of positions 433 to 497 in FIG. 3, and the C-terminal amino acid corresponds to that situated at one of positions 546 to 559 in FIG. 3,
the fragment of 117 amino acids delimited by the amino acids situated at positions 443 and 559 in FIG. 3, i.e. the following SEQ ID NO: 28 peptide:

```
Val Thr Val Thr Ala Leu Ala His Pro Pro Ser Gly
Leu His Pro Thr Pro Ser Thr Ala Pro Gly Pro His
Val Pro Leu Met Pro Pro Ser Pro Pro Ser Gln Val
Ile Pro Ala Ser Glu Pro Lys Arg His Pro Ser Thr
Leu Pro Val Ile Ser Asp Ala Arg Ser Val Leu Leu
Glu Ala Ile Arg Ile Ala Val Glu Tyr Ser Asp Ser
Glu Asp Asp Ser Glu Phe Asp Glu Lys Gly Ile Gln
Leu Arg Lys Val Glu Glu Gln Arg Glu Gln Glu Ala
Val Asp Trp Leu Glu
``` the fragment of 104 amino acids delimited by the amino acids situated at positions 443 and 546 in FIG. 3, i.e. the following SEQ ID NO: 30 peptide:

```
Val Thr Val Thr Ala Leu Ala His Pro Pro Ser Gly
Leu His Pro Thr Pro Ser Thr Ala Pro Gly Pro His
Val Pro Leu Met Pro Pro Ser Pro Pro Ser Gln Val
Ile Pro Ala Ser Glu Pro Lys Arg His Pro Ser Thr
Leu Pro Val Ile Ser Asp Ala Arg Ser Val Leu Leu
Glu Ala Ile Arg Lys Gly Ile Gln Leu Arg Lys Val
Glu Glu Gln Arg Glu Gln Glu Ala Lys His Glu Arg
Ile Glu Asn Asp Val Ala Thr Ile Leu Ser Arg Arg
Ile Ala Val Glu Tyr Ser Asp Ser
``` the fragment of 63 amino acids delimited by the amino acids situated at positions 497 and 559 in FIG. 3, i.e. the following SEQ ID NO: 32 peptide:

```
Ala Arg Ser Val Leu Leu Glu Ala Ile Arg Lys Gly
Ile Gln Leu Arg Lys Val Glu Glu Gln Arg Glu Gln
Glu Ala Lys His Glu Arg Ile Glu Asn Asp Val Ala
Thr Ile Leu Ser Arg Arg Ile Ala Val Glu Tyr Ser
Asp Ser Glu Asp Asp Ser Glu Phe Asp Glu Val Asp
Trp Leu Glu
``` the fragment of 50 amino acids delimited by the amino acids situated at positions 497 and 546 in FIG. 3, i.e. the following SEQ ID NO: 34 peptide:

```
Ala Arg Ser Val Leu Leu Glu Ala Ile Arg Lys Gly
Ile Gln Leu Arg Lys Val Glu Glu Gln Arg Glu Gln
Glu Ala Lys His Glu Arg Ile Glu Asn Asp Val Ala
Thr Ile Leu Ser Arg Arg Ile Ala Val Glu Tyr Ser
Asp Ser
``` or the peptide sequences derived from the above-mentioned peptide fragments, in particular by substitution, addition or removal of one or more amino acids of these fragments, said derived sequences having the property defined above, of WASP family proteins and said fragments thereof.

The invention concerns more particularly the above-mentioned use of peptide fragments of WASP family proteins of non-human origin.

Advantageously, the peptide fragments of WASP family proteins of non-human origin used are chosen from:
fragments of non-human mammalian WASP family proteins, such as:
fragments of murine WASP protein, themselves chosen from:
those including:
the verprolin homology domain delimited by the amino acids situated at positions 448 and 465 of the peptide sequence SEQ ID NO: 36 of murine WASP protein represented in FIG. 4, or a peptide sequence derived from the above-mentioned domain as defined above,
and the cofilin homology domain delimited by the amino acids situated at positions 487 and 505 of the peptide sequence SEQ ID NO: 36 of murine WASP protein represented in FIG. 4, or a peptide sequence derived from the above-mentioned domain as defined above,
fragments of which the N-terminal amino acid corresponds to that situated at one of positions 420 to 448 in FIG. 4, and the C-terminal amino acid corresponds to that situated at one of positions 505 to 520 in FIG. 4,
the fragment of 101 amino acids delimited by the amino acids situated at positions 420 and 520 in FIG. 4, i.e. the following SEQ ID NO: 38 peptide:

```
Pro Pro Pro Cys Pro Gly Ser Gly Pro Ala Pro Pro
Pro Leu Pro Pro Thr Pro Val Ser Gly Gly Ser Pro
Ala Pro Gly Gly Gly Arg Gly Ala Leu Leu Asp Gln
Ile Arg Gln Gly Ile Gln Leu Asn Lys Thr Pro Gly
```

-continued

Ala Leu Glu Asn Ser Val Gln Gln Pro Pro Ala Gln

Gln Ser Glu Gln Leu Val Gly Ala Leu Met His Val

Met Gln Lys Arg Ser Arg Val Ile His Ser Ser Asp

Glu Gly Glu Asp Gln Thr Gly Glu Asp Glu Asp

Asp Glu Trp Asp Asp the fragment of 86 amino acids delimited by the amino acids situated at positions 420 and 505 in FIG. 4, i.e. the following SEQ ID NO: 40 peptide:

Pro Pro Pro Cys Pro Gly Ser Gly Pro Ala Pro Pro

Pro Leu Pro Pro Thr Pro Val Ser Gly Gly Ser Pro

Ala Pro Gly Gly Gly Arg Gly Ala Leu Leu Asp Gln

Ile Arg Gln Gly Ile Gln Leu Asn Lys Thr Pro Gly

Ala Leu Glu Asn Ser Val Gln Gln Pro Pro Ala Gln

Gln Ser Glu Gly Leu Val Gly Ala Leu Met His Val

Met Gln Lys Arg Ser Arg Val Ile His Ser Ser Asp

Glu Gly the fragment of 73 amino acids delimited by the amino acids situated at positions 448 and 520 in FIG. 4, i.e. the following SEQ ID NO: 42 peptide:

Gly Arg Gly Ala Leu Leu Asp Gln Ile Arg Gln Gly

Ile Gln Leu Asn Lys Thr Pro Gly Ala Leu Glu Asn

Ser Val Gln Gln Pro Pro Ala Gln Gln Ser Glu Gly

Leu Val Gly Ala Leu Met His Val Met Gln Lys Arg

Ser Arg Val Ile His Ser Ser Asp Glu Gly Glu Asp

Gln Thr Gly Glu Asp Glu Glu Asp Asp Glu Trp Asp

Asp the fragment of 58 amino acids delimited by the amino acids situated at positions 448 and 505 in FIG. 4, i.e. the following SEQ ID NO: 44 peptide:

Gly Arg Gly Ala Leu Leu Asp Gln Ile Arg Gln Gly

Ile Gln Leu Asn Lys Thr Pro Gly Ala Leu Glu Asn

Ser Val Gln Gln Pro Pro Ala Gln Gln Ser Glu Gly

Leu Val Gly Ala Leu Met His Val Met Gln Lys Arg

Ser Arg Val Ile His Ser Ser Asp Glu Gly fragments of rat N-WASP protein, themselves chosen from:
  those including:
    the verprolin homologous sequence delimited by the amino acids situated at positions 401 and 417 of the peptide sequence SEQ ID NO: 46 of rat N-WASP protein represented in FIG. 5, or a peptide sequence derived from the above-mentioned domain as defined above,
    and the verprolin homologous sequence delimited by the amino acids situated at positions 429 and 444 of the peptide sequence SEQ ID NO: 46 of rat N-WASP protein represented in FIG. 5, or a peptide sequence derived from the above-mentioned domain as defined above,
    and the cofilin homology domain contained in the above-mentioned N-WASP protein, i.e. the domain delimited by the amino acids situated at positions 466 and 484 of the peptide sequence SEQ ID NO: 46 of rat N-WASP protein represented in FIG. 5, or a peptide sequence derived from the above-mentioned domain as defined above,
  fragments of which the N-terminal amino acid corresponds to that situated at one of positions 401 to 429 in FIG. 5, and the C-terminal amino acid corresponds to that situated at one of positions 484 to 501 in FIG. 5,
  the fragment of 101 amino acids delimited by the amino acids situated at positions 401 and 501 in FIG. 5, i.e. the following SEQ ID NO: 48 peptide:

Asn Lys Ala Ala Leu Leu Asp Gln Ile Arg Glu Gly

Ala Gln Leu Lys Lys Val Glu Gln Asn Ser Arg Pro

Val Ser Cys Ser Gly Arg Asp Ala Leu Leu Asp Gln

Ile Arg Gln Gly Ile Gln Leu Lys Ser Val Ser Asp

Gly Gln Glu Ser Thr Pro Pro Thr Pro Ala Pro Thr

Ser Gly Ile Val Ser Asp Glu Asp Glu Asp Asp Asp

Asp Glu Glu Asp Phe Gln Asp Asp Asp Glu Trp Glu

Asp the fragment of 84 amino acids delimited by the amino acids situated at positions 401 and 484 in FIG. 5, i.e. the following SEQ ID NO: 50 peptide:

Asn Lys Ala Ala Leu Leu Asp Gln Ile Arg Glu Gly

Ala Gln Leu Lys Lys Val Glu Gln Asn Ser Arg Pro

Val Ser Cys Ser Gly Arg Asp Ala Leu Leu Asp Gln

Ile Arg Gln Gly Ile Gln Leu Lys Ser Val Ser Asp

Gly Gln Glu Ser Thr Pro Pro Thr Pro Ala Pro Thr

Ser Gly Ile Val Gly Ala Leu Met Glu Val Met Gln

Lys Arg Ser Lys Ala Ile His Ser Ser Asp Glu Asp the fragment of 73 amino acids delimited by the amino acids situated at positions 429 and 501 in FIG. 5, i.e. the following SEQ ID NO: 52 peptide:

Gly Arg Asp Ala Leu Leu Asp Gln Ile Arg Gln Gly

Ile Gln Leu Lys Ser Val Ser Asp Gly Gln Glu Ser

Thr Pro Pro Thr Pro Ala Pro Thr Ser Gly Ile Val

Gly Ala Leu Met Glu Val Met Gln Lys Arg Ser Lys

Ala Ile His Ser Ser Asp Glu Asp Glu Asp Asp

-continued

Asp Glu Glu Asp Phe Gln Asp Asp Glu Trp Glu

Asp the fragment of 56 amino acids delimited by the amino acids situated at positions 429 and 484 in FIG. 5, i.e. the following SEQ ID NO: 54 peptide:

Gly Arg Asp Ala Leu Leu Asp Gln Ile Arg Gln Gly

Ile Gln Leu Lys Ser Val Ser Asp Gly Gln Glu Ser

Thr Pro Pro Thr Pro Ala Pro Thr Ser Gly Ile Val

Gly Ala Leu Met Glu Val Met Gln Lys Arg Ser Lys

Ala Ile His Ser Ser Asp Glu Asp fragments of bovine N-WASP protein, themselves chosen from:
  those including:
    the verprolin homology domain delimited by the amino acids situated at positions 405 and 421 of the peptide sequence SEQ ID NO: 56 of bovine N-WASP protein represented in FIG. 6, or a peptide sequence derived from the above-mentioned domain as defined above,
    and/or the verprolin homology domain delimited by the amino acids situated at positions 433 and 488 of the peptide sequence SEQ ID NO: 56 of bovine N-WASP protein represented in FIG. 6, or a peptide sequence derived from the above-mentioned domain as defined above,
    and the cofilin homology domain delimited by the amino acids situated at positions 470 and 488 of the peptide sequence SEQ ID NO: 56 of bovine N-WASP protein represented in FIG. 6, or a peptide sequence derived from the above-mentioned domain as defined above,
  fragments of which the N-terminal amino acid corresponds to that situated at one of positions 405 to 433 in FIG. 6, and the C-terminal amino acid corresponds to that situated at one of positions 488 to 505 in FIG. 6,
  the fragment of 101 amino acids delimited by the amino acids situated at positions 405 and 505 in FIG. 6, i.e. the following SEQ ID NO: 58 peptide:

Ser Lys Ala Ala Leu Leu Asp Gln Ile Arg Glu Gly

Ala Gln Leu Lys Lys Val Glu Gln Asn Ser Arg Pro

Val Ser Cys Ser Gly Arg Asp Ala Leu Leu Asp Gln

Ile Arg Gln Gly Ile Gln Leu Lys Ser Val Thr Asp

Ala Pro Glu Ser Thr Pro Pro Ala Pro Ala Pro Thr

Ser Gly Ile Val Gly Ala Leu Met Glu Val Met Gln

Lys Arg Ser Lys Ala Ile His Ser Ser Asp Glu Asp

Glu Asp Glu Asp Asp Glu Asp Phe Glu Asp Asp

Asp Glu Trp Glu Asp the fragment of 84 amino acids delimited by the amino acids situated at positions 405 and 488 in FIG. 6, i.e. the following SEQ ID NO: 60 peptide:

Ser Lys Ala Ala Leu Leu Asp Gln Ile Arg Glu Gly

Ala Gln Leu Lys Lys Val Glu Gln Asn Ser Arg Pro

Val Ser Cys Ser Gly Arg Asp Ala Leu Leu Asp Gln

Ile Arg Gln Gly Ile Gln Leu Lys Ser Val Thr Asp

Ala Pro Glu Ser Thr Pro Pro Ala Pro Ala Pro Thr

Ser Gly Ile Val Gly Ala Leu Met Glu Val Met Gln

Lys Arg Ser Lys Ala Ile His Ser Ser Asp Glu Asp the fragment of 73 amino acids delimited by the amino acids situated at positions 433 and 488 in FIG. 6, i.e. the following SEQ ID NO: 62 peptide:

Gly Arg Asp Ala Leu Leu Asp Gln Ile Arg Gln Gly

Ile Gln Leu Lys Ser Val Thr Asp Ala Pro Glu Ser

Thr Pro Pro Ala Pro Ala Pro Thr Ser Gly Ile Val

Gly Ala Leu Met Glu Val Met Gln Lys Arg Ser Lys

Ala Ile His Ser Ser Asp Glu Asp Glu Asp Glu Asp

Asp Asp Glu Asp Phe Glu Asp Asp Asp Glu Trp Glu

Asp the fragment of 56 amino acids delimited by the amino acids situated at positions 433 and 488 in FIG. 6, i.e. the following SEQ ID NO: 64 peptide:

Gly Arg Asp Ala Leu Leu Asp Gln Ile Arg Gln Gly

Ile Gln Leu Lys Ser Val Thr Asp Ala Pro Glu Ser

Thr Pro Pro Ala Pro Ala Pro Thr Ser Gly Ile Val

Gly Ala Leu Met Glu Val Met Gln Lys Arg Ser Lys

Ala Ile His Ser Ser Asp Glu Asp fragments of WASP family proteins of micro-organisms, such as:
  fragments of *Saccharomyces cerevisiae* Las17 protein, themselves chosen from:
    those including:
      the verprolin homology domain delimited by the amino acids situated at positions 447 and 466 of the peptide sequence SEQ ID NO: 66 of Las17 protein represented in FIG. 7, or a peptide sequence derived from the above-mentioned domain as defined above,
      and the cofilin homology domain delimited by the amino acids situated at positions 607 and 624 of the peptide sequence SEQ ID NO: 66 of Las17 protein represented in FIG. 7, or a peptide sequence derived from the above-mentioned domain as defined above,
    fragments of which the N-terminal amino acid corresponds to that situated at one of positions 422 to 447 in FIG. 7, and the C-terminal amino acid corresponds to that situated at one of positions 624 to 633 in FIG. 7,
    the fragment of 212 amino acids delimited by the amino acids situated at positions 422 and 633 in FIG. 7, i.e. the following SEQ ID NO: 68 peptide:

Ser Asn Met Ser Ser Pro Pro Pro Pro Val Thr
Thr Phe Asn Thr Leu Thr Pro Gln Met Thr Ala Ala
Thr Gly Gln Pro Ala Val Pro Leu Pro Gln Asn Thr
Gln Ala Pro Ser Gln Ala Thr Asn Val Pro Val Ala
Pro Pro Pro Pro Ala Ser Leu Gly Gln Ser Gln
Ile Pro Gln Ser Ala Pro Ser Ala Pro Ile Pro Pro
Thr Leu Pro Ser Thr Thr Ser Ala Ala Pro Pro Pro
Pro Pro Ala Phe Leu Thr Gln Gln Pro Gln Ser Gly
Gly Ala Pro Ala Pro Pro Pro Pro Gln Met Pro
Ala Thr Ser Thr Ser Gly Gly Gly Ser Phe Ala Glu
Thr Thr Gly Asp Ala Gly Arg Asp Ala Leu Leu Ala
Ser Ile Arg Gly Ala Gly Gly Ile Gly Ala Leu Arg
Lys Val Asp Lys Ser Gln Leu Asp Lys Pro Ser Val
Leu Leu Gln Glu Ala Arg Gly Glu Ser Ala Ser Pro
Pro Ala Ala Ala Gly Asn Gly Gly Thr Pro Gly Gly
Pro Pro Ala Ser Leu Ala Asp Ala Leu Ala Ala Ala
Leu Asn Lys Arg Lys Thr Lys Val Gly Ala His Asp
Asp Met Asp Asn Gly Asp Asp Trp the fragment of 203 amino acids delimited by the amino acids situated at positions 422 and 624 in FIG. 7, i.e. the following SEQ ID NO: 70 peptide:

Ser Asn Met Ser Ser Pro Pro Pro Pro Val Thr
Thr Phe Asn Thr Leu Thr Pro Gln Met Thr Ala Ala
Thr Gly Gln Pro Ala Val Pro Leu Pro Gln Asn Thr
Gln Ala Pro Ser Gln Ala Thr Asn Val Pro Val Ala
Pro Pro Pro Pro Ala Ser Leu Gly Gln Ser Gln
Ile Pro Gln Ser Ala Pro Ser Ala Pro Ile Pro Pro
Thr Leu Pro Ser Thr Thr Ser Ala Ala Pro Pro Pro
Pro Pro Ala Phe Leu Thr Gln Gln Pro Gln Ser Gly
Gly Ala Pro Ala Pro Pro Pro Pro Gln Met Pro
Ala Thr Ser Thr Ser Gly Gly Gly Ser Phe Ala Glu
Thr Thr Gly Asp Ala Gly Arg Asp Ala Leu Leu Ala
Ser Ile Arg Gly Ala Gly Gly Ile Gly Ala Leu Arg
Lys Val Asp Lys Ser Gln Leu Asp Lys Pro Ser Val
Leu Leu Gln Glu Ala Arg Gly Glu Ser Ala Ser Pro
Pro Ala Ala Ala Gly Asn Gly Gly Thr Pro Gly Gly
Pro Pro Ala Ser Leu Ala Asp Ala Leu Ala Ala Ala
Leu Asn Lys Arg Lys Thr Lys Val Gly Ala His the fragment of 187 amino acids delimited by the amino acids situated at positions 447 and 633 in FIG. 7, i.e. the following SEQ ID NO: 72 peptide:

Gly Gln Pro Ala Val Pro Leu Pro Gln Asn Thr Gln
Ala Pro Ser Gln Ala Thr Asn Val Pro Val Ala Pro
Pro Pro Pro Ala Ser Leu Gly Gln Ser Gln Ile
Pro Gln Ser Ala Pro Ser Ala Pro Ile Pro Pro Thr
Leu Pro Ser Thr Thr Ser Ala Ala Pro Pro Pro
Pro Ala Phe Leu Thr Gln Gln Pro Gln Ser Gly Gly
Ala Pro Ala Pro Pro Pro Pro Gln Met Pro Ala
Thr Ser Thr Ser Gly Gly Gly Ser Phe Ala Glu Thr
Thr Gly Asp Ala Gly Arg Asp Ala Leu Leu Ala Ser
Ile Arg Gly Ala Gly Gly Ile Gly Ala Leu Arg Lys
Val Asp Lys Ser Gln Leu Asp Lys Pro Ser Val Leu
Leu Gln Glu Ala Arg Gly Glu Ser Ala Ser Pro Pro
Ala Ala Ala Gly Asn Gly Gly Thr Pro Gly Gly Pro
Pro Ala Ser Leu Ala Asp Ala Leu Ala Ala Ala Leu
Asn Lys Arg Lys Thr Lys Val Gly Ala His Asp Asp
Met Asp Asn Gly Asp Asp Trp the fragment of 178 amino acids delimited by the amino acids situated at positions 447 and 624 in FIG. 7, i.e. the following SEQ ID NO: 74 peptide:

Gly Gln Pro Ala Val Pro Leu Pro Gln Asn Thr Gln
Ala Pro Ser Gln Ala Thr Asn Val Pro Val Ala Pro
Pro Pro Pro Ala Ser Leu Gly Gln Ser Gln Ile
Pro Gln Ser Ala Pro Ser Ala Pro Ile Pro Pro Thr
Leu Pro Ser Thr Thr Ser Ala Ala Pro Pro Pro
Pro Ala Phe Leu Thr Gln Gln Pro Gln Ser Gly Gly
Ala Pro Ala Pro Pro Pro Pro Gln Met Pro Ala
Thr Ser Thr Ser Gly Gly Gly Ser Phe Ala Glu Thr
Thr Gly Asp Ala Gly Arg Asp Ala Leu Leu Ala Ser
Ile Arg Gly Ala Gly Gly Ile Gly Ala Leu Arg Lys
Val Asp Lys Ser Gln Leu Asp Lys Pro Ser Val Leu
Leu Gln Glu Ala Arg Gly Glu Ser Ala Ser Pro Pro
Ala Ala Ala Gly Asn Gly Gly Thr Pro Gly Gly Pro
Pro Ala Ser Leu Ala Asp Ala Leu Ala Ala Ala Leu
Asn Lys Arg Lys Thr Lys Val Gly Ala His fragments of WASP homologous protein (Wsp1p) of *Schizosaccharomyces pombe*, themselves chosen from:
those including:
the verprolin homology domain delimited by the amino acids situated at positions 501 and 517 of the peptide sequence SEQ ID NO: 76 of WASP homologous protein (Wsp1p) of *Schizosaccharomyces pombe* represented in FIG. 8, or a peptide sequence derived from the above-mentioned domain as defined above, and the cofilin homology domain delimited by the amino acids situated at positions 548 and 565 of the peptide sequence SEQ ID NO: 76 of WASP homologous protein (Wsp1p) of *Schizosaccharomyces pombe* represented in FIG. 8, or a peptide sequence derived from the above-mentioned domain as defined above, fragments of which the N-terminal amino acid corresponds to that situated at one of positions 477 to 501 in FIG. 8, and the C-terminal amino acid corresponds to that situated at one of positions 565 to 574 in FIG. 8, the fragment of 98 amino acids delimited by the amino acids situated at positions 477 and 574 in FIG. 8, i.e. the following SEQ ID NO: 78 peptide:

Pro Pro Ala Pro Ala Pro Ala Pro Ala Ala Pro Val Ala Ser Ile Ala

Glu Leu Pro Gln Gln Asp Gly Arg Ala Asn Leu Met Ala Ser Ile Arg

Ala Ser Gly Gly Met Asp Leu Leu Lys Ser Arg Lys Val Ser Ala Ser

Pro Ser Val Ala Ser Thr Lys Thr Ser Asn Pro Pro Val Glu Ala Pro

Pro Ser Asn Asn Leu Met Asp Ala Leu Ala Ser Ala Leu Asn Gln Arg

Lys Thr Lys Val Ala Gln Ser Asp Glu Glu Asp Glu Asp Asp Asp Glu

Trp Asp the fragment of 89 amino acids delimited by the amino acids situated at positions 477 and 565 in FIG. 8, i.e. the following SEQ ID NO: 80 peptide:

Pro Pro Ala Pro Ala Pro Ala Pro Ala Ala Pro Val Ala Ser Ile Ala

Glu Leu Pro Gln Gln Asp Gly Arg Ala Asn Leu Met Ala Ser Ile Arg

Ala Ser Gly Gly Met Asp Leu Leu Lys Ser Arg Lys Val Ser Ala Ser

Pro Ser Val Ala Ser Thr Lys Thr Ser Asn Pro Pro Val Glu Ala Pro

Pro Ser Asn Asn Leu Met Asp Ala Leu Ala Ser Ala Leu Asn Gln Arg

Lys Thr Lys Val Ala Gln Ser Asp Glu the fragment of 74 amino acids delimited by the amino acids situated at positions 501 and 574 in FIG. 8, i.e. the following SEQ ID NO: 82 peptide:

Ala Asn Leu Met Ala Ser Ile Arg Ala Ser Gly Gly Met Asp Leu Leu

Lys Ser Arg Lys Val Ser Ala Ser Pro Ser Val Ala Ser Thr Lys Thr

Ser Asn Pro Pro Val Glu Ala Pro Pro Ser Asn Asn Leu Met Asp Ala

Leu Ala Ser Ala Leu Asn Gln Arg Lys Thr Lys Val Ala Gln Ser Asp

Glu Glu Asp Glu Asp Asp Asp Glu Trp Asp the fragment of 65 amino acids delimited by the amino acids situated at positions 501 and 565 in FIG. 8, i.e. the following SEQ ID NO: 84 peptide:

```
Ala Asn Leu Met Ala Ser Ile Arg Ala Ser Gly Gly Met Asp Leu Leu

Lys Ser Arg Lys Val Ser Ala Ser Pro Ser Val Ala Ser Thr Lys Thr

Ser Asn Pro Pro Val Glu Ala Pro Pro Ser Asn Asn Leu Met Asp Ala

Leu Ala Ser Ala Leu Asn Gln Arg Lys Thr Lys Val Ala Gln Ser Asp

Glu
``` the peptide sequences derived from the above-mentioned peptide fragments, in particular by substitution, addition or removal of one or more amino acids of these fragments, said derived sequences having the property defined above, of WASP family proteins and said fragments thereof.

The invention also concerns the above-mentioned use of above-defined peptide fragments, or sequences derived from these, fused on the N-terminal or C-terminal side with one or more peptide sequences facilitating the detection and purification of the above-mentioned peptide fragments or derived sequences, without greatly affecting the above-mentioned property of the latter to polymerise actin, inducing cellular motility. Among such peptide sequences fused to peptide fragments, or to sequences derived from the latter, of the invention, we may cite that of glutathion-S-transferase (GST, described in Smith D. B. and Johnson K. S., Gene 67: 31–141 (1988)) fused to the N-terminal part of the above-mentioned peptide fragments or derived sequences, or that of epitopes recognised by specific antibodies, such as that of the myc9E10 epitope (described in Evan G. I. et al., Molecular and Cellular Biology 5: 3610–3616 (1985)) fused to the C-terminal part of the above-mentioned peptide fragments or derived sequences.

The invention also concerns the above-mentioned peptide fragments, or sequences derived from these, as such, i.e. more particularly peptide fragments of WASP family proteins of eukaryotic cells chosen from those including:

the verprolin homology domain contained in WASP family proteins, or in a protein derived from the latter, or at least one of the two verprolin homologous sequences when said WASP family proteins contain two of these sequences, or one peptide sequence derived from the above-mentioned domain, in particular by substitution, addition or removal of one or more amino acids, and retaining the property of this domain to bind to actin, and the cofilin homology domain contained in WASP family proteins, or in a protein derived from the latter, or a peptide sequence derived from the above-mentioned domain, in particular by substitution, addition or removal of one or more amino acids, and retaining the property of this domain to intervene in actin polymerisation, or peptide sequences derived from the above-mentioned peptide fragments of WASP family proteins, in particular by substitution, addition or removal of one or more amino acids of these fragments, said derived sequences having the above-mentioned property of WASP protein and said fragments, to the exclusion:
of the peptide fragment of human WASP protein delimited by the amino acids situated at positions 429 to 503 of the peptide sequence represented in FIG. 1,
of the peptide fragment of human WASP protein delimited by the amino acids situated at positions 187 to 489 of the peptide sequence represented in FIG. 1,
of the peptide fragment of human WASP protein delimited by the amino acids situated at positions 422 to 489 of the peptide sequence represented in FIG. 1,
of the peptide fragment of human N-WASP protein delimited by the amino acids situated at positions 392 to 505 of the peptide sequence represented in FIG. 2,
of the peptide fragment of human Scar1 protein delimited by the amino acids situated at positions 443 to 559 of the peptide sequence represented in FIG. 3,
of the peptide fragment of bovine N-WASP protein delimited by the amino acids situated at positions 392 to 505, and that delimited by the amino acids situated at positions 392 to 485 of the peptide sequence represented in FIG. 6.

The invention concerns more particularly the above-mentioned peptide fragments of human WASP protein, or peptide sequences derived from the latter, said fragments being chosen from those including:
the verprolin homology domain delimited by the amino acids situated at positions 430 and 446 of the peptide sequence SEQ ID NO: 2 of human WASP protein represented in FIG. 1, or a peptide sequence derived from the above-mentioned domain as defined above,
and the cofilin homology domain delimited by the amino acids situated at positions 469 and 487 of the peptide sequence SEQ ID NO: 2 of human WASP protein represented in FIG. 1, or a peptide sequence derived from the above-mentioned domain as defined above.

The invention concerns still more particularly fragments of human WASP protein, chosen from fragments of which the N-terminal amino acid corresponds to that situated at one of positions 404 to 430 in FIG. 1, and the C-terminal amino acid corresponds to that situated at one of positions 487 to 502 in FIG. 1, and more particularly the above-mentioned SEQ ID NO: 4, SEQ ID NO: 6, SEQ ID NO: 8 and SEQ ID NO: 10 peptides, or the sequences derived from the latter as defined above.

The invention concerns more particularly the above-mentioned peptide fragments of human N-WASP protein, or peptide sequences derived from the latter, said fragments being chosen from those including:
the verprolin homologous sequence delimited by the amino acids situated at positions 405 and 421 of the peptide sequence SEQ ID NO: 12 of human N-WASP protein represented in FIG. 2, or a peptide sequence derived from the above-mentioned domain as defined above,
and/or the verprolin homologous sequence delimited by the amino acids situated at positions 433 and 449 of the peptide sequence SEQ ID NO: 12 of human N-WASP protein represented in FIG. 2, or a peptide sequence derived from the above-mentioned domain as defined above,
and the cofilin homology domain contained in the above-mentioned N-WASP protein, i.e. the domain delimited by the amino acids situated at positions 470 and 488 of the peptide sequence SEQ ID NO: 12 of human N-WASP protein represented in FIG. 2, or a peptide sequence derived from the above-mentioned domain as defined above.

The invention concerns still more particularly fragments of human N-WASP protein, chosen from fragments of which the N-terminal amino acid corresponds to that situated at one of positions 392 to 433 in FIG. 2, and the C-terminal amino acid corresponds to that situated at one of positions 488 to 505 in FIG. 2, and more particularly the above-mentioned SEQ ID NO: 16, SEQ ID NO: 18, SEQ ID NO: 20, SEQ ID NO: 22 and SEQ ID NO: 24 peptides, or the sequences derived from the latter as defined above.

The invention concerns more particularly the above-mentioned peptide fragments of human Scar1 protein, or peptide sequences derived from the latter, said fragments being chosen from those including:

the verprolin homology domain delimited by the amino acids situated at positions 497 and 513 of the peptide sequence SEQ ID NO: 26 of human Scar1 protein represented in FIG. 3, or a peptide sequence derived from the above-mentioned domain as defined above, and the cofilin homology domain delimited by the amino acids situated at positions 531 and 546 of the peptide sequence SEQ ID NO: 26 of human Scar1 protein represented in FIG. 3, or a peptide sequence derived from the above-mentioned domain as defined above.

The invention concerns still more particularly fragments of human Scar1 protein, chosen from fragments of which the N-terminal amino acid corresponds to that situated at one of positions 443 to 497 in FIG. 3, and the C-terminal amino acid corresponds to that situated at one of positions 546 to 559 in FIG. 3, and more particularly the above-mentioned SEQ ID NO: 28, SEQ ID NO: 30, SEQ ID NO: 32 and SEQ ID NO: 34 peptides, or the sequences derived from the latter as defined above.

The invention concerns more particularly the above-mentioned peptide fragments of murine WASP protein, or peptide sequences derived from the latter, said fragments being chosen from those including:

the verprolin homology domain delimited by the amino acids situated at positions 448 and 465 of the peptide sequence SEQ ID NO: 36 of murine WASP protein represented in FIG. 4, or a peptide sequence derived from the above-mentioned domain as defined above, and the cofilin homology domain delimited by the amino acids situated at positions 487 and 505 of the peptide sequence SEQ ID NO: 36 of murine WASP protein represented in FIG. 4, or a peptide sequence derived from the above-mentioned domain as defined above.

The invention concerns still more particularly fragments of murine WASP protein, chosen from fragments of which the N-terminal amino acid corresponds to that situated at one of positions 420 to 448 in FIG. 4, and the C-terminal amino acid corresponds to that situated at one of positions 505 to 520 in FIG. 4, and more particularly the above-mentioned SEQ ID NO: 38, SEQ ID NO: 40, SEQ ID NO: 42 and SEQ ID NO: 44 peptides, or the sequences derived from the latter as defined above.

The invention concerns more particularly the above-mentioned peptide fragments of rat N-WASP protein, or peptide sequences derived from the latter, said fragments being chosen from those including:

the verprolin homologous sequence delimited by the amino acids situated at positions 401 and 417 of the peptide sequence SEQ ID NO: 46 of rat N-WASP protein represented in FIG. 5, or a peptide sequence derived from the above-mentioned domain as defined above, and/or the verprolin homologous sequence delimited by the amino acids situated at positions 429 and 444 of the peptide sequence SEQ ID NO: 46 of rat N-WASP protein represented in FIG. 5, or a peptide sequence derived from the above-mentioned domain as defined above, and the cofilin homology domain contained in the above-mentioned N-WASP protein, i.e. the domain delimited by the amino acids situated at positions 466 and 484 of the peptide sequence SEQ ID NO: 46 of rat N-WASP protein represented in FIG. 5, or a peptide sequence derived from the above-mentioned domain as defined above.

The invention concerns still more particularly fragments of rat N-WASP protein chosen from fragments of which the N-terminal amino acid corresponds to that situated at one of positions 401 to 429 in FIG. 5, and the C-terminal amino acid corresponds to that situated at one of positions 484 to 501 in FIG. 5, and more particularly the above-mentioned SEQ ID NO: 48, SEQ ID NO: 50, SEQ ID NO: 52 and SEQ ID NO: 54 peptides, or the sequences derived from the latter as defined above.

The invention concerns more particularly the above-mentioned peptide fragments of bovine N-WASP protein, or peptide sequences derived from the latter, said fragments being chosen from those including:

the verprolin homology domain delimited by the amino acids situated at positions 405 and 421 of the peptide sequence SEQ ID NO: 56 of bovine N-WASP protein represented in FIG. 6, or a peptide sequence derived from the above-mentioned domain as defined above, and/or the verprolin homology domain delimited by the amino acids situated at positions 433 and 488 of the peptide sequence SEQ ID NO: 56 of bovine N-WASP protein represented in FIG. 6, or a peptide sequence derived from the above-mentioned domain as defined above, and the cofilin homology domain delimited by the amino acids situated at positions 470 and 488 of the peptide sequence SEQ ID NO: 56 of bovine N-WASP protein represented in FIG. 6, or a peptide sequence derived from the above-mentioned domain as defined above.

The invention concerns still more particularly fragments of bovine N-WASP protein chosen from fragments of which the N-terminal amino acid corresponds to that situated at one of positions 405 to 433 in FIG. 6, and the C-terminal amino acid corresponds to that situated at one of positions 488 to 505 in FIG. 6, and more particularly the above-mentioned SEQ ID NO: 58, SEQ ID NO: 60, SEQ ID NO: 62 and SEQ ID NO: 64 peptides, or the sequences derived from the latter as defined above.

The invention concerns more particularly the above-mentioned peptide fragments of *Saccharomyces cerevisiae* Las17 protein, or peptide sequences derived from the latter, said fragments being chosen from those including:

the verprolin homology domain delimited by the amino acids situated at positions 447 and 466 of the peptide sequence SEQ ID NO: 66 of Las17 protein represented in FIG. 7, or a peptide sequence derived from the above-mentioned domain as defined above.

and the cofilin homology domain delimited by the amino acids situated at positions 607 and 624 of the peptide sequence SEQ ID NO: 66 of Las17 protein represented in FIG. 7, or a peptide sequence derived from the above-mentioned domain as defined above.

The invention concerns still more particularly fragments of *Saccharomyces cerevisiae* Las17 protein chosen from fragments of which the N-terminal amino acid corresponds to that situated at one of positions 422 to 447 in FIG. 7, and the C-terminal amino acid corresponds to that situated at one of positions 624 to 633 in FIG. 7, and more particularly the above-mentioned SEQ ID NO: 68, SEQ ID NO: 70, SEQ ID NO: 72 and SEQ ID NO: 74 peptides, or the sequences derived from the latter as defined above.

The invention concerns more particularly the above-mentioned peptide fragments of *Schizosaccharomyces pombe* (Wsp1p) protein, or peptide sequences derived from the latter, said fragments being chosen from those including:
  the verprolin homology domain delimited by the amino acids situated at positions 501 and 517 of the peptide sequence SEQ ID NO: 76 of WASP homologous protein (Wsp1p) of *Schizosaccharomyces pombe* represented in FIG. 8, or a peptide sequence derived from the above-mentioned domain as defined above,
  and the cofilin homology domain delimited by the amino acids situated at positions 548 and 565 of the peptide sequence SEQ ID NO: 76 of WASP homologous protein (Wsp1p) of *Schizosaccharomyces pombe* represented in FIG. 8, or a peptide sequence derived from the above-mentioned domain as defined above.

The invention concerns still more particularly fragments of WASP homologous protein (Wsp1p) of *Schizosaccharomyces pombe* chosen from fragments of which the N-terminal amino acid corresponds to that situated at one of positions 477 to 501 in FIG. 8, and the C-terminal amino acid corresponds to that situated at one of positions 565 to 574 in FIG. 8, and more particularly the above-mentioned SEQ ID NO: 78, SEQ ID NO: 80, SEQ ID NO: 82 and SEQ ID NO: 84 peptides, or the sequences derived from the latter as defined above.

The invention also concerns the nucleotide sequences coding for the above-mentioned peptide fragments, or for the proteins derived from the latter, or for the fusion proteins as described above.

The invention concerns more particularly:
  the nucleotide sequences of which the 5' end corresponds to the nucleotide situated at one of positions 1244 to 1322 of the nucleotide sequence SEQ ID NO: 1 represented in FIG. 1, and the 3' end corresponds to the nucleotide situated at one of positions 1495 to 1540 in FIG. 1, said nucleotide sequences coding for the above-mentioned fragments of human WASP protein, of which the N-terminal amino acid corresponds to that situated at one of positions 404 to 430 in FIG. 1, and the C-terminal amino acid corresponds to that situated at one of positions 487 to 502 in FIG. 1,
  nucleotide sequence SEQ ID NO: 3 delimited by the nucleotides situated at positions 1244 and 1540 of FIG. 1, and coding for the peptide fragment of human WASP protein corresponding to the above-mentioned SEQ ID NO: 4 peptide,
  nucleotide sequence SEQ ID NO: 5 delimited by the nucleotides situated at positions 1244 and 1495 of FIG. 1, and coding for the peptide fragment of human WASP protein corresponding to the above-mentioned SEQ ID NO: 6 peptide,
  nucleotide sequence SEQ ID NO: 7 delimited by the nucleotides situated at positions 1322 and 1540 of FIG. 1, and coding for the peptide fragment of human WASP protein corresponding to the above-mentioned SEQ ID NO: 8 peptide,
  nucleotide sequence SEQ ID NO: 9 delimited by the nucleotides situated at positions 1322 and 1495 of FIG. 1, and coding for the peptide fragment of human WASP protein corresponding to the above-mentioned SEQ ID NO: 10 peptide,
  the nucleotide sequences derived by degeneration of the genetic code of the above-mentioned nucleotide sequences, and coding for the above-mentioned peptide fragments,
  the nucleotide sequences derived from the above-mentioned nucleotide sequences and coding for the sequences derived from said peptide fragments as defined above.

The invention concerns still more particularly:
  the nucleotide sequences of which the 5' end corresponds to the nucleotide situated at one of positions 1174 to 1299 of the nucleotide sequence SEQ ID NO: 11 represented in FIG. 2, and the 3' end corresponds to the nucleotide situated at one of positions 1464 to 1515 in FIG. 2, said nucleotide sequences coding for the above-mentioned fragments of N-WASP protein, of which the N-terminal amino acid corresponds to that situated at one of positions 392 to 433 in FIG. 2 and the C-terminal amino acid corresponds to that situated at one of positions 488 to 505 in FIG. 2, to the exclusion of the nucleotide sequence delimited by the nucleotides situated at positions 1174 to 1515 coding for the peptide fragment of N-WASP protein delimited by the amino acids situated at positions 392 to 505 of the peptide sequence represented in FIG. 2,
  nucleotide sequence SEQ ID NO: 15 delimited by the nucleotides situated at positions 1174 and 1464 coding for the peptide fragment of N-WASP protein corresponding to the above-mentioned SEQ ID NO: 16 peptide, nucleotide sequence SEQ ID NO: 17 delimited by the nucleotides situated at positions 1213 and 1515 coding for the peptide fragment of N-WASP protein corresponding to the above-mentioned SEQ ID NO: 18 peptide,
  nucleotide sequence SEQ ID NO: 19 delimited by the nucleotides situated at positions 1213 and 1464 coding for the peptide fragment of N-WASP protein corresponding to the above-mentioned SEQ ID NO: 20 peptide,
  nucleotide sequence SEQ ID NO: 21 delimited by the nucleotides situated at positions 1297 and 1515 coding for the peptide fragment of N-WASP protein corresponding to the above-mentioned SEQ ID NO: 22 peptide,
  nucleotide sequence SEQ ID NO: 23 delimited by the nucleotides situated at positions 1297 and 1464 coding for the peptide fragment of N-WASP protein corresponding to the above-mentioned SEQ ID NO: 24 peptide,
  the nucleotide sequences derived by degeneration of the genetic code of the above-mentioned nucleotide sequences, and coding for the above-mentioned peptide fragments,
  the nucleotide sequences derived from the above-mentioned nucleotide sequences and coding for the sequences derived from said peptide fragments as defined above.

The invention concerns still more particularly:
the nucleotide sequences of which the 5' end corresponds to the nucleotide situated at one of positions 1327 to 1489 of the nucleotide sequence SEQ ID NO: 26 represented in FIG. 3, and the 3' end corresponds to the nucleotide situated at one of positions 1638 to 1677 in FIG. 3, said nucleotide sequences coding for the above-mentioned fragments of human Scar1 protein, of which the N-terminal amino acid corresponds to that situated at one of positions 546 to 497 in FIG. 3 and the C-terminal amino acid corresponds to that situated at one of positions 487 to 559 in FIG. 3, nucleotide sequence SEQ ID NO: 27 delimited by the nucleotides situated at positions 1327 and 1677 in FIG. 3, and coding for the peptide fragment of human Scar1 protein corresponding to the above-mentioned SEQ ID NO: 28 peptide, nucleotide sequence SEQ ID NO: 29 delimited by the nucleotides situated at positions 1327 and 1638 in FIG. 3, and coding for the peptide fragment of human Scar1 protein corresponding to the above-mentioned SEQ ID NO: 30 peptide, nucleotide sequence SEQ ID NO: 31 delimited by the nucleotides situated at positions 1489 and 1677 in FIG. 3, and coding for the peptide fragment of human Scar1 protein corresponding to the above-mentioned SEQ ID NO: 32 peptide, nucleotide sequence SEQ ID NO: 33 delimited by the nucleotides situated at positions 1489 and 1638 in FIG. 3, and coding for the peptide fragment of human Scar1 protein corresponding to the above-mentioned SEQ ID NO: 34 peptide, the nucleotide sequences derived by degeneration of the genetic code of the above-mentioned nucleotide sequences, and coding for the above-mentioned peptide fragments, the nucleotide sequences derived from the above-mentioned nucleotide sequences and coding for the sequences derived from said peptide fragments as defined above.

The invention concerns still more particularly:
the nucleotide sequences of which the 5' end corresponds to the nucleotide situated at one of positions 1282 to 1366 of the nucleotide sequence SEQ ID NO: 36 represented in FIG. 4, and the 3' end corresponds to the nucleotide situated at one of positions 1539 to 1584 in FIG. 4, said nucleotide sequences coding for the above-mentioned fragments of murine WASP protein, of which the N-terminal amino acid corresponds to that situated at one of positions 420 to 448 in FIG. 4 and the C-terminal amino acid corresponds to that situated at one of positions 505 to 520 in FIG. 4, nucleotide sequence SEQ ID NO: 37 delimited by the nucleotides situated at positions 1282 and 1584 in FIG. 4, and coding for the peptide fragment of murine WASP protein corresponding to the above-mentioned SEQ ID NO: 38 peptide, nucleotide sequence SEQ ID NO: 39 delimited by the nucleotides situated at positions 1282 and 1584 in FIG. 4, and coding for the peptide fragment of murine WASP protein corresponding to the above-mentioned SEQ ID NO: 40 peptide, nucleotide sequence SEQ ID NO: 41 delimited by the nucleotides situated at positions 1366 and 1584 in FIG. 4, and coding for the peptide fragment of murine WASP protein corresponding to the above-mentioned SEQ ID NO: 42 peptide, nucleotide sequence SEQ ID NO: 43 delimited by the nucleotides situated at positions 1366 and 1539 in FIG. 4, and coding for the peptide fragment of murine WASP protein corresponding to the above-mentioned SEQ ID NO: 44 peptide, the nucleotide sequences derived by degeneration of the genetic code of the above-mentioned nucleotide sequences, and coding for the above-mentioned peptide fragments, the nucleotide sequences derived from the above-mentioned nucleotide sequences and coding for the sequences derived from said peptide fragments as defined above.

The invention concerns still more particularly:
the nucleotide sequences of which the 5' end corresponds to the nucleotide situated at one of positions 1272 to 1356 of the nucleotide sequence SEQ ID NO: 46 represented in FIG. 5, and the 3' end corresponds to the nucleotide situated at one of positions 1523 to 1574 in FIG. 5, said nucleotide sequences coding for the above-mentioned fragments of rat N-WASP protein, of which the N-terminal amino acid corresponds to that situated at one of positions 401 to 429 in FIG. 5 and the C-terminal amino acid corresponds to that situated at one of positions 484 to 501 in FIG. 5, nucleotide sequence SEQ ID NO: 47 delimited by the nucleotides situated at positions 1272 and 1574 in FIG. 5, and coding for the peptide fragment of rat N-WASP protein corresponding to the above-mentioned SEQ ID NO: 48 peptide, nucleotide sequence SEQ ID NO: 49 delimited by the nucleotides situated at positions 1272 and 1523 in FIG. 5, and coding for the peptide fragment of rat N-WASP protein corresponding to the above-mentioned SEQ ID NO: 50 peptide, nucleotide sequence SEQ ID NO: 51 delimited by the nucleotides situated at positions 1356 and 1574 in FIG. 5, and coding for the peptide fragment of rat N-WASP protein corresponding to the above-mentioned SEQ ID NO: 52 peptide, nucleotide sequence SEQ ID NO: 53 delimited by the nucleotides situated at positions 1356 and 1523 in FIG. 5, and coding for the peptide fragment of rat N-WASP protein corresponding to the above-mentioned SEQ ID NO: 54 peptide, the nucleotide sequences derived by degeneration of the genetic code of the above-mentioned nucleotide sequences, and coding for the above-mentioned peptide fragments, the nucleotide sequences derived from the above-mentioned nucleotide sequences and coding for the sequences derived from said peptide fragments as defined above.

The invention concerns still more particularly:
the nucleotide sequences of which the 5' end corresponds to the nucleotide situated at one of positions 1500 to 1584 of the nucleotide sequence SEQ ID NO: 56 represented in FIG. 6, and the 3' end corresponds to the nucleotide situated at one of positions 1751 to 1802 in FIG. 6, said nucleotide sequences coding for the above-mentioned fragments of bovine N-WASP protein, of which the N-terminal amino acid corresponds to that situated at one of positions 405 to 433 in FIG. 6 and the C-terminal amino acid corresponds to that situated at one of positions 488 to 505 in FIG. 6, nucleotide sequence SEQ ID NO: 57 delimited by the nucleotides situated at positions 1500 and 1802 in FIG.

6, and coding for the peptide fragment of bovine N-WASP protein corresponding to the above-mentioned SEQ ID NO: 58 peptide, nucleotide sequence SEQ ID NO: 59 delimited by the nucleotides situated at positions 1500 and 1751 in FIG. 6, and coding for the peptide fragment of bovine N-WASP protein corresponding to the above-mentioned SEQ ID NO: 60 peptide, nucleotide sequence SEQ ID NO: 61 delimited by the nucleotides situated at positions 1584 and 1802 in FIG. 6, and coding for the peptide fragment of bovine N-WASP protein corresponding to the above-mentioned SEQ ID NO: 62 peptide, nucleotide sequence SEQ ID NO: 63 delimited by the nucleotides situated at positions 1584 and 1751 in FIG. 6, and coding for the peptide fragment of bovine N-WASP protein corresponding to the above-mentioned SEQ ID NO: 64 peptide, the nucleotide sequences derived by degeneration of the genetic code of the above-mentioned nucleotide sequences, and coding for the above-mentioned peptide fragments, the nucleotide sequences derived from the above-mentioned nucleotide sequences and coding for the sequences derived from said peptide fragments as defined above.

The invention concerns still more particularly:

the nucleotide sequences of which the 5' end corresponds to the nucleotide situated at one of positions 2035 to 2110 of the nucleotide sequence SEQ ID NO: 66 represented in FIG. 7, and the 3' end corresponds to the nucleotide situated at one of positions 2643 to 2670 in FIG. 7, said nucleotide sequences coding for the above-mentioned fragments of *Saccharomyces cerevisiae* Las17 protein, of which the N-terminal amino acid corresponds to that situated at one of positions 422 to 447 in FIG. 7 and the C-terminal amino acid corresponds to that situated at one of positions 624 to 633 in FIG. 7, nucleotide sequence SEQ ID NO: 67 delimited by the nucleotides situated at positions 2035 and 2670 in FIG. 7, and coding for the peptide fragment of *Saccharomyces cerevisiae* Las17 protein corresponding to the above-mentioned SEQ ID NO: 68 peptide, nucleotide sequence SEQ ID NO: 69 delimited by the nucleotides situated at positions 2035 and 2643 in FIG. 7, and coding for the peptide fragment of *Saccharomyces cerevisiae* Las 17 protein corresponding to the above-mentioned SEQ ID NO: 70 peptide, nucleotide sequence SEQ ID NO: 71 delimited by the nucleotides situated at positions 2110 and 2670 in FIG. 7, and coding for the peptide fragment of *Saccharomyces cerevisiae* Las17 protein corresponding to the above-mentioned SEQ ID NO: 72 peptide, nucleotide sequence SEQ ID NO: 73 delimited by the nucleotides situated at positions 2110 and 2643 in FIG. 7, and coding for the peptide fragment of *Saccharomyces cerevisiae* Las17 protein corresponding to the above-mentioned SEQ ID NO: 74 peptide, the nucleotide sequences derived by degeneration of the genetic code of the above-mentioned nucleotide sequences, and coding for the above-mentioned peptide fragments, the nucleotide sequences derived from the above-mentioned nucleotide sequences and coding for the sequences derived from said peptide fragments as defined above.

The invention concerns still more particularly:

the nucleotide sequences of which the 5' end corresponds to the nucleotide situated at one of positions 1429 to 1501 of the nucleotide sequence SEQ ID NO: 76 represented in FIG. 8, and the 3' end corresponds to the nucleotide situated at one of positions 1695 to 1722 in FIG. 8, said nucleotide sequences coding for the above-mentioned fragments of WASP homologous protein (Wsp1p) of *Schizosaccharomyces pombe*, of which the N-terminal amino acid corresponds to that situated at one of positions 477 to 501 in FIG. 8 and the C-terminal amino acid corresponds to that situated at one of positions 565 to 574 in FIG. 8, nucleotide sequence SEQ ID NO: 77 delimited by the nucleotides situated at positions 1429 and 1722 in FIG. 8, and coding for the peptide fragment of WASP homologous protein (Wsp1p) of *Schizosaccharomyces pombe* corresponding to the above-mentioned SEQ ID NO: 78 peptide, nucleotide sequence SEQ ID NO: 79 delimited by the nucleotides situated at positions 1429 and 1695 in FIG. 8, and coding for the peptide fragment of WASP homologous protein (Wsp1p) of *Schizosaccharomyces pombe* corresponding to the above-mentioned SEQ ID NO: 80 peptide, nucleotide sequence SEQ ID NO: 81 delimited by the nucleotides situated at positions 1501 and 1722 in FIG. 8, and coding for the peptide fragment of WASP homologous protein (Wsp1p) of *Schizosaccharomyces pombe* corresponding to the above-mentioned SEQ ID NO: 82 peptide, nucleotide sequence SEQ ID NO: 83 delimited by the nucleotides situated at positions 1501 and 1695 in FIG. 8, and coding for the peptide fragment of WASP homologous protein (Wsp1p) of *Schizosaccharomyces pombe* corresponding to the above-mentioned SEQ ID NO: 84 peptide, the nucleotide sequences derived by degeneration of the genetic code of the above-mentioned nucleotide sequences, and coding for the above-mentioned peptide fragments, the nucleotide sequences derived from the above-mentioned nucleotide sequences and coding for the sequences derived from said peptide fragments as defined above.

The invention also concerns vectors, in particular plasmids, containing a nucleotide sequence as defined above.

The invention also concerns host cells transformed by an above-mentioned vector, said cells expressing the above-mentioned peptide fragments, or the derived sequences described above, in recombinant form. Advantageously, the above-mentioned host cells are chosen from the following: *Escherichia coli* D5α and *Escherichia coli* BL21.

The invention also concerns reagents for the implementation of a process for the detection or screening of molecules having an inhibiting or stimulating effect on the formation of the actin cytoskeleton, and hence an inhibiting or stimulating effect on cellular motility, said reagent comprising at least one peptide fragment defined above, bound or adsorbed to a support capable of moving under the effect of actin polymerisation, when said support bound to said fragment is placed in a medium containing the elements necessary for actin polymerisation, in particular when said support is added to a medium containing mainly Arp2/3 complex, VASP protein (vasodilator-stimulated phosphoprotein), colifin, and capping proteins, this medium possibly being, for example, an extract prepared from supernatants of lysed cells from the organism.

Capping protein is an element essential for WASP-dependent motility. These proteins are capable of converting actin polymerisation into actin-dependent movement, spatially limiting polymerisation to certain sites in the cellular cytoskeleton. By comparison, in the absence of capping proteins, actin polymerisation still takes place, but since it is uncontrolled, it cannot generate any force. Capping proteins are made up of two sub-units, alpha (p34) and beta (p32) which are both required for capping activity. The dimer is associated with the plus end of the filament which is normally favoured for the addition of actin monomers and thus blocks the addition of monomers. Genes coding for capping proteins have been identified in all species studied to date, and have been shown to be indispensable for the survival of organisms. In humans, Cap beta 1, beta2, G and CapZ have been identified to date. It is also known that multifunctional proteins such as gelsolin and villin also have a capping activity in addition to their other actin-modifying activities.

The invention concerns more particularly reagents as defined above, chosen from microspheres whose diameter is advantageously between approx. 100 nm and approx. 10,000 nm, the material constituting the microspheres itself being chosen preferably from polystyrenes or latex, said microspheres each advantageously containing approx. 5,000 to approx. 50,000 molecules of above-mentioned peptide fragment or a sequence derived according to the invention.

Advantageously, the above-mentioned peptide fragment, or its derived sequence, are adsorbed onto the surface of said microspheres, said reagent being obtained by simple mixing of said microspheres with said peptide fragment, or with its derived sequence.

The invention concerns more particularly reagents as defined above, chosen from drops of oil, in particular oil of C14 to C18, such as palmitic acid, whose diameter is advantageously between approx. 1 μm and approx. 20 μm.

The invention also concerns any process for the detection or screening of molecules as defined above, having an inhibiting or stimulating effect on the formation of the actin cytoskeleton, and hence an inhibiting or stimulating effect on cellular motility, said process comprising:
  a stage of placing the tested molecule in the presence of a reagent as described above, into a medium containing actin and the elements necessary for actin polymerisation, in particular into an extract of cellular supernatant or other medium as defined above,
  followed by the eventual detection of inhibition or activation of the actin polymerisation process on the surface of said reagent, compared with a control (i.e. a medium as described above not containing the tested molecule, and containing said reagent), respectively demonstrating an inhibiting or stimulating effect on the formation of the actin cytoskeleton.

Advantageously, the above-mentioned medium into which the tested molecule is placed in the presence of said reagent, contains a compound marked in particular by fluorescence, making it possible to detect movement of said reagent. By way of illustration, the above-mentioned marked compound is a fluorescent derivative of actin, such as actin-rhodamine (available commercially), enabling actin polymerisation to be made visible by epifluorescence microscopy.

The invention also concerns the use of the process as defined above, for detection or screening of molecules, as defined above, capable of being used as medicaments in the treatment of pathologies linked to a dysfunction of the actin polymerisation process within the context of formation of the actin cytoskeleton, or capable of having a cytotoxic effect corresponding to inhibition or stimulation of the formation of the actin cytoskeleton.

The invention also concerns a kit for implementation of an above-mentioned process, comprising
  a reagent as defined above,
  possibly a marked compound defined above enabling polymerisation of actin to be made visible, in particular actin marked with fluorescence,
  possibly an appropriate medium containing the elements necessary for actin polymerisation, in particular an extract of cellular supernatant as defined above.

The invention will be further illustrated by means of the following detailed description of preparation of microspheres coated with a peptide fragment of the invention, and of detection of actin polymerisation on the surface of these microspheres in an extract of cellular supernatant.

I) Material and Methods

The sequence coding for the WH2/A domain of human WASP protein (i.e. the fragment of 99 amino acids delimited by the amino acids situated at positions 404 and 502 in FIG. 1, also designated peptide SEQ ID NO: 4) and that coding for the myc9E10 epitope were amplified by PCR. The myc epitope fused to the carboxy-terminal portion of the protein serves as a molecular tag, making possible the detection of the protein by immunological approaches without needing an anti-WASP antibody. This DNA sequence was introduced into the pGEX2T vector (Pharmacia) downstream of the sequence coding for glutathion-S-transferase (GST), generating the WH2/A-pGEX2T plasmid. The GST domain was chosen in this work, as it facilitates purification of the recombinant protein, and it has been shown that this domain does not inhibit the actin-polymerisation capacity of the GST-VCA protein derived from N-WASP in a pyrene-actin test (Rohatgi et al., 1999). FIG. 3 shows the organisation into domains of GST-WH2. This recombinant protein is made up of GST and WH2/A domains, of 237 and 99 residues and of a myc9E10 epitope of 9 residues, respectively.

Purification and characterisation of the GST-WH2/A protein were carried out as follows.

E. coli bacteria (strain BL21) were transformed with WH2/1-pGEX2T plasmid. The bacteria were cultivated in standard LB medium containing the antibiotic ampicillin to keep bacteria comprising the plasmid under selection pressure. The bacteria were cultivated in suspension at 37° C. until the culture reached an optical density of 0.8 to 600 nm. Subsequently, isopropylthio-β-D-galactoside (IPTG) was added to the medium, with a final concentration of 1 mM to induce production of the protein. After 2 hours, the bacteria were collected by centrifugation, and the pellets were stored at −80° C. The pellets were thawed and added to extraction buffer (saline solution buffered with phosphate pH 7.2, 200 NaCl, 2 mM EDTA (ethylenediaminetetraacetic acid)) containing 1 μg/ml of each of the following protease inhibitors: leupeptin, benzamidin, pepstatin, in a ratio of 1 gr of pellet to 10 volumes of extraction buffer. The suspension was sonicated until it was no longer viscous. The extract was centrifuged at 20,000×g for 10 minutes at 4° C. and the supernatant containing the GST-WH2/A protein was conserved. The GST-WH2/A protein was purified from the bacterial extract by affinity chromatography on resin coupled to glutathione (Pharmacia) and eluated with 20 mM glutathione reduced according to the manufacturers' recommendations. The purification was confirmed by analysis of the GST-WH2/A by electrophoresis on acrylamide gel. The presence of the myc epitope in the GST-WH2/A sequence was confirmed by immunological impression with an antibody directed against this epitope.

The GST-WH2/A protein was absorbed onto 500 nm latex beads (Polyscience Inc., 400 Valley Road, Warrington Pa., USA) following the manufacturers' instructions. These beads, added to the extracts prepared from cells, are capable of polymerising actin sufficiently to bring about the movement of these beads.

Adsorption of the GST-WA protein onto drops of oil: a water-oil emulsion was prepared as follows: 100 µl of oil are mixed with 900 µl of borate buffer 0.1 MpH=8.5 (boric acid buffered with NaOH). The solution is sonicated (wave) for a few seconds and a white foam is obtained. The size of the oil drops is between 20 µm and 1 µm. In a 1.5 ml Eppendorf, 20 µl of this solution are mixed with 100 µl of the abovementioned GST-WH2/A protein (also designated GST-WA) (1 mg/ml in borate buffer). This solution is left to incubate at ambient temperature for 12 hours (overnight) on a rotating agitator. After incubation, the solution is centrifuged for approx. one minute at 5000 rpm with a small table-top centrifuge. Drops of oil are located in the upper part of the solution. A too strong and/or too prolonged centrifugation brings about fusion of the oil drops. The bottom part of the solution (buffer alone) is removed with a pipette and the top part of the solution is resuspended in PBS (Phosphate Buffer Saline). The oil drops are cleaned at least four times in this manner and finally resuspended in 100 µl of PBS. 1 µl of this solution is mixed with 10 µl of HeLa extracts.

Inhibition of actin polymerisation induced by GST-WA protein: 10 µm polystyrene particles (Polysciences inc.) are covered to saturation with GST-WA protein according to the manufacturer's protocol. The particles are resuspended to 1% solid in PBS (Phosphate Buffer Saline) and stored on ice. To test the independence of the actin polymerisation mechanism induced by GST-WA we prepared three solutions. Each sample contained 15 µl of HeLa extracts (supplemented with ATP, creatine phosphate and actin marked with rhodamine), 0.5 µl of GST-WA particles and 1.5 µl of PBS (A), or 1.5 µl of GST-WA protein at 1 mg/ml (B) or 1.5 µl of GST-PRO protein (PRO corresponding to the fragment delimited by the amino acids situated at positions 235 to 584 of the ActA protein of *Listeria monocytogenes*) at 1 mg/ml (C). 6 µl of the final mixture of these three solutions were sealed between slide and coverglass. We observed fluorescence (rhodamine actin) around the particles for thirty minutes and measured the intensity of fluorescence on a population of forty beads using a microscope (Leica) and a linear digital camera (Micromax Princeton instrument). The average intensity M (arbitrary unit) was 95,000±13,000 for sample A (positive control). For sample B, M=0±1000, the actin polymerisation on the surface of the particles was inhibited by the addition of GST-WA in solution. For sample C, M=4000±1500; the addition to the solution of the GST-PRO protein did not inhibit the actin polymerisation on the surface of the particles. The intensity was lower than in case A (PBS); this is probably due to the activity induced by GST-PRO in the extracts which results in a very high consumption of rhodamine actin. These results show that the actin polymerisation mechanism induced by the GST-WA protein is independent of the GST-PRO actin polymerisation mechanism.

B) Uses

1) Uses of GST-WH2/A Beads and of the Cellular Actin Polymerisation Test

Cellular movement dependent on the actin cytoskeleton occurs during embryonic development, immune response and healing of wounds. However, the molecular mechanism whereby the cytoskeleton participates in physiological or physio-pathological processes are still poorly understood. This is due to the fact that few in vitro experimental systems are available for studying these processes.

The invention proposes an in vitro test for actin polymerisation on the surface of beads, and shows that the system reproduces the essential characteristics of actin polymerisation in human cells. For example, these beads recruit large proteins for actin polymerisation in cells, such as Arp2/3 complex and cofilin. Moreover, the components recruited onto the surface of the beads, are targets for tyrosine kinase signalling pathways. Thanks to this in vitro system, it is now possible to study the conditions necessary for actin polymerisation in cells, a process which up to now has not been accessible to direct experimental manipulation.

a) Anti-metastatic Component Screening Process

At present, it has not been possible to develop anti-metastatic medicaments targeted at the actin cytoskeleton, as simple tests for screening banks of chemicals have not been available. The beads of the invention "mimic" the dynamic cytoskeleton of cells in motion and thus constitute an ideal test for researching molecules affecting the dynamics of the cytoskeleton. Chemicals thus identified will subsequently be used to develop medicaments for treatment of metastatic cancers.

b) Anti-parasitic Antibiotic Screening Process

The system of beads described here is based on human proteins which are necessary for actin polymerisation in human cells. However, these proteins have been conserved throughout evolution, from yeast to humans, via amoebae. Despite the conservation of their basic function, these proteins also diverge at the level of their primary sequence, suggesting particular functional differences. As in the case of metastatic cancers, the actin cytoskeleton of parasites is rarely the target of medicaments used in the treatment of parasitoses, despite the important role which it plays in the infectious cycle of numerous parasites (for example amoebae). It is conceivable that medicaments which affect the human actin cytoskeleton only when they are used in a strong concentration, affect that of parasites at much lower concentrations. This is why, thanks to the universal nature of the evolution of the actin cytoskeleton, the system of beads of the invention also enables research into medicaments which can be used in the treatment of parasitoses.

c) Detection of Secondary Effects of Medicaments

In another test, the beads are used to verify and confirm that medicaments have no secondary effects on cellular actin polymerisation. Thus it is possible to avoid the disastrous consequences of drug treatments unintentionally affecting cellular migration during the development of the embryo in pregnant women. For example after some years of use, it has been shown that the teratogenic properties of valproic acid, an anti-epileptic medicament, are due to its secondary effects on the actin cytoskeleton.

2) Process for Screening Molecules Affecting Cellular Actin Polymerisation

The most effective screening tests carried out on new medicaments have the following properties: they are simple, cheap and quick. The cellular actin polymerisation test of the invention has all these characteristics. Beads measuring 200–500 nm can be produced by absorbing purified GST-WH2/A recombinant protein on their surface. Once prepared, the beads are stable for several months at 4° C. The beads are then added to extracts prepared from supernatants of lysed cells in culture. The volume of extract necessary for an experiment is of the order of a few microlitres, reducing the cost of the experiment. These extracts have the advantage that they can be produced in a large quantity and stored for a long period, at −80° C. Before the addition of these beads, a fluorescent actin derivative (commercial actin-rhodamine) is added to the extract to make the actin polymerisation visible by epifluorescence microscopy. The actin polymerisation is observed 15 min after the addition of the beads, resulting in an accumulation of fluorescent actin around the beads. Starting with a stock of standardised reagents, the experiment takes less than 30 min and one person is capable of dealing with several samples in parallel.

This process can be automated, enabling the rapid screening of a large number samples.

To identify the active components, it is necessary to test the chemical products at variable concentrations. The inventors have shown that low quantities of solvents used to dissolve these products (water, ethanol, dimethyl sulphoxide) do not disturb the system of the invention. Moreover, this screening test has been validated by showing that it is sensitive to known medicaments inhibiting actin polymerisation, such as latrunculin and cytochalasin D.

The invention claimed is:

1. A process for the detection or screening of molecules, having a modulating effect on the formation of actin cytoskeleton, and hence a modulating effect on cellular motility, said process comprising:
   a stage of placing a test molecule in the presence of a reagent in a medium containing actin and elements necessary for actin polymerization,
   followed by detecting any inhibition or activation of the actin polymerization process on the surface of said reagent, compared with a control, respectively demonstrating an inhibiting or stimulating effect on the formation of the actin cytoskeleton by the test molecule, and wherein said reagent comprises the WASP peptide fragment consisting of SEQ ID NO: 4, bound or adsorbed to a support capable of moving under the effect of actin polymerization, when said support bound to said fragment is placed in a medium containing the elements necessary for actin polymerization.

2. A process for the detection or screening of molecules, having a modulating effect on the formation of actin cytoskeleton, and hence a modulating effect on cellular motility, said process comprising:
   placing a test molecule in the presence of a reagent in a medium containing actin and the elements necessary for actin polymerization,
   detecting any inhibition or activation of the actin polymerization process on the surface of said reagent, compared with a control, respectively demonstrating an inhibiting or stimulating effect on the formation of the actin cytoskeleton by the test molecule, and wherein said reagent comprises the WASP peptide fragment consisting of SEQ ID NO: 4, bound or adsorbed to a support capable of moving under the effect of actin polymerization, when said support bound to said fragment is placed in a medium containing the elements necessary for actin polymerization, and wherein said reagent is in a form chosen from microspheres.

3. A process for the detection or screening of molecules, having a modulating effect on the formation of actin cytoskeleton, and hence a modulating effect on cellular motility, said process comprising:
   placing a test molecule in the presence of a reagent in a medium containing actin and the elements necessary for actin polymerization, detecting any inhibition or activation of the actin polymerization polymerisation process on the surface of said reagent, compared with a control, respectively demonstrating an inhibiting or stimulating effect on the formation of the actin cytoskeleton by the test molecule, and wherein said reagent contains a WASP peptide fragment consisting of SEQ ID NO: 4, bound or adsorbed to a support capable of moving under the effect of actin polymerization, when said support bound to said fragment is placed in a medium containing the elements necessary for actin polymerization.

4. The process according to claim 3, wherein said reagent is in the form of microsphere.

5. The process according to claim 4, wherein said microspheres have a diameter approximately between 100 nm and approximately 10,000 nm.

6. The process according to claim 4, wherein said microspheres comprise a material selected from the group consisting of polystyrene and latex.

7. The process according to claim 5, wherein said microspheres comprise a material selected from the group consisting of polystyrene and latex.

8. The process according to claim 3, wherein said support is a microsphere.

* * * * *

SEQUENCE LISTING

<160> NUMBER OF SEQ ID NOS: 84

<210> SEQ ID NO 1
<211> LENGTH: 1806
<212> TYPE: DNA
<213> ORGANISM: Homo sapiens
<220> FEATURE:
<221> NAME/KEY: CDS
<222> LOCATION: (35)..(1540)

<400> SEQUENCE: 1

```
agcctcgcca gagaagacaa gggcagaaag cacc atg agt ggg ggc cca atg gga        55
                                    Met Ser Gly Gly Pro Met Gly
                                    1               5 gga agg ccc ggg ggc cga gga gca cca gcg gtt cag cag aac ata ccc          103
Gly Arg Pro Gly Gly Arg Gly Ala Pro Ala Val Gln Gln Asn Ile Pro
            10                  15                  20 tcc acc ctc ctc cag gac cac gag aac cag cga ctc ttt gag atg ctt          151
Ser Thr Leu Leu Gln Asp His Glu Asn Gln Arg Leu Phe Glu Met Leu
    25                  30                  35 gga cga aaa tgc ttg acg ctg gcc act gca gtt gtt cag ctg tac ctg          199
Gly Arg Lys Cys Leu Thr Leu Ala Thr Ala Val Val Gln Leu Tyr Leu
40                  45                  50                  55 gcg ctg ccc cct gga gct gag cac tgg acc aag gag cat tgt ggg gct          247
Ala Leu Pro Pro Gly Ala Glu His Trp Thr Lys Glu His Cys Gly Ala
                60                  65                  70 gtg tgc ttc gtg aag gat aac ccc cag aag tcc tac ttc atc cgc ctt          295
Val Cys Phe Val Lys Asp Asn Pro Gln Lys Ser Tyr Phe Ile Arg Leu
            75                  80                  85 tac ggc ctt cag gct ggt cgg ctg ctc tgg gaa cag gag ctg tac tca          343
Tyr Gly Leu Gln Ala Gly Arg Leu Leu Trp Glu Gln Glu Leu Tyr Ser
        90                  95                  100 cag ctt gtc tac tcc acc ccc acc ccc ttc ttc cac acc ttc gct gga          391
Gln Leu Val Tyr Ser Thr Pro Thr Pro Phe Phe His Thr Phe Ala Gly
    105                 110                 115 gat gac tgc caa gcg ggg ctg aac ttt gca gac gag gac gag gcc cag          439
Asp Asp Cys Gln Ala Gly Leu Asn Phe Ala Asp Glu Asp Glu Ala Gln
120                 125                 130                 135 gcc ttc cgg gcc ctc gtg cag gag aag ata caa aaa agg aat cag agg          487
Ala Phe Arg Ala Leu Val Gln Glu Lys Ile Gln Lys Arg Asn Gln Arg
                140                 145                 150 caa agt gga gac aga cgc cag cta ccc cca cca aca cca gcc aat            535
Gln Ser Gly Asp Arg Arg Gln Leu Pro Pro Pro Thr Pro Ala Asn
            155                 160                 165 gaa gag aga aga gga ggg ctc cca ccc ctg ccc ctg cat cca ggt gga         583
Glu Glu Arg Arg Gly Gly Leu Pro Pro Leu Pro Leu His Pro Gly Gly
        170                 175                 180
```

-continued

```
gac caa gga ggc cct cca gtg ggt ccg ctc tcc ctg ggg ctg gcg aca      631
Asp Gln Gly Gly Pro Pro Val Gly Pro Leu Ser Leu Gly Leu Ala Thr
    185                 190                 195 gtg gac atc cag aac cct gac atc acg agt tca cga tac cgt ggg ctc      679
Val Asp Ile Gln Asn Pro Asp Ile Thr Ser Ser Arg Tyr Arg Gly Leu
200                 205                 210                 215 cca gca cct gga cct agc cca gct gat aag aaa cgc tca ggg aag aag      727
Pro Ala Pro Gly Pro Ser Pro Ala Asp Lys Lys Arg Ser Gly Lys Lys
                220                 225                 230 aag atc agc aaa gct gat att ggt gca ccc agt gga ttc aag cat gtc      775
Lys Ile Ser Lys Ala Asp Ile Gly Ala Pro Ser Gly Phe Lys His Val
        235                 240                 245 agc cac gtg ggg tgg gac ccc cag aat gga ttt gac gtg aac aac ctc      823
Ser His Val Gly Trp Asp Pro Gln Asn Gly Phe Asp Val Asn Asn Leu
            250                 255                 260 gac cca gat ctg cgg agt ctg ttc tcc agg gca gga atc agc gag gcc      871
Asp Pro Asp Leu Arg Ser Leu Phe Ser Arg Ala Gly Ile Ser Glu Ala
265                 270                 275 cag ctc acc gac gcc gag acc tct aaa ctt atc tac gac ttc att gag      919
Gln Leu Thr Asp Ala Glu Thr Ser Lys Leu Ile Tyr Asp Phe Ile Glu
280                 285                 290                 295 gac cag ggt ggg ctg gag gct gtg cgg cag gag atg agg cgc cag gag      967
Asp Gln Gly Gly Leu Glu Ala Val Arg Gln Glu Met Arg Arg Gln Glu
                300                 305                 310 cca ctt ccg ccg ccc cca ccg cca tct cga gga ggg aac cag ctc ccc     1015
Pro Leu Pro Pro Pro Pro Pro Pro Ser Arg Gly Gly Asn Gln Leu Pro
        315                 320                 325 cgg ccc cct att gtg ggg ggt aac aag ggt cgt tct ggt cca ctg ccc     1063
Arg Pro Pro Ile Val Gly Gly Asn Lys Gly Arg Ser Gly Pro Leu Pro
            330                 335                 340 cct gta cct ttg ggg att gcc cca ccc cca aca ccc cgg gga ccc         1111
Pro Val Pro Leu Gly Ile Ala Pro Pro Pro Thr Pro Arg Gly Pro
345                 350                 355 cca ccc cca ggc cga ggg ggc cct cca cca cca ccc cct cca gct act     1159
Pro Pro Pro Gly Arg Gly Gly Pro Pro Pro Pro Pro Pro Pro Ala Thr
360                 365                 370                 375 gga cgt tct gga cca ctg ccc cct cca ccc cct gga gct ggt ggg cca     1207
Gly Arg Ser Gly Pro Leu Pro Pro Pro Pro Gly Ala Gly Gly Pro
                380                 385                 390 ccc atg cca cca cca ccg cca cca ccg cca ccg ccc agc tcc ggg         1255
Pro Met Pro Pro Pro Pro Pro Pro Pro Pro Pro Pro Ser Ser Gly
        395                 400                 405 aat gga cca gcc cct ccc cca ctc cct cct gct ctg gtg cct gcc ggg     1303
Asn Gly Pro Ala Pro Pro Pro Leu Pro Pro Ala Leu Val Pro Ala Gly
            410                 415                 420 ggc ctg gcc cct ggt ggg ggt cgg gga gcg ctt ttg gat caa atc cgg     1351
Gly Leu Ala Pro Gly Gly Gly Arg Gly Ala Leu Leu Asp Gln Ile Arg
425                 430                 435 cag gga att cag ctg aac aag acc cct ggg gcc cca gag agc tca gcg     1399
Gln Gly Ile Gln Leu Asn Lys Thr Pro Gly Ala Pro Glu Ser Ser Ala
440                 445                 450                 455 ctg cag cca cca cct cag agc tca gag gga ctg gtg ggg gcc ctg atg     1447
Leu Gln Pro Pro Pro Gln Ser Ser Glu Gly Leu Val Gly Ala Leu Met
                460                 465                 470 cac gtg atg cag aag aga agc aga gcc atc cac tcc tcc gac gaa ggg     1495
His Val Met Gln Lys Arg Ser Arg Ala Ile His Ser Ser Asp Glu Gly
            475                 480                 485 gag gac cag gct ggc gat gaa gat gaa gat gat gaa tgg gat gac         1540
Glu Asp Gln Ala Gly Asp Glu Asp Glu Asp Asp Glu Trp Asp Asp
490                 495                 500
```

-continued

```
<br>

tgagtggctg agttacttgc tgccctgtgc tcctccccgc aggacatggc tccccctcca   1600
cctgctctgt gcccaccctc cactctcctc ttccagggcc cccaaccccc catttcttcc   1660
ccaccaaccc ctccaatgct gttatccctg cctggtcctc acactcaccc aacaatccca   1720
aggccctttt tatacaaaaa ttctcagttc tcttcactca aggattttta aagaaaaata   1780
aagaattgt ctttctgtct ctctat                                        1806

<210> SEQ ID NO 2
<211> LENGTH: 502
<212> TYPE: PRT
<213> ORGANISM: Homo sapiens

<400> SEQUENCE: 2

Met Ser Gly Gly Pro Met Gly Gly Arg Pro Gly Gly Arg Gly Ala Pro
1               5                   10                  15

Ala Val Gln Gln Asn Ile Pro Ser Thr Leu Leu Gln Asp His Glu Asn
            20                  25                  30

Gln Arg Leu Phe Glu Met Leu Gly Arg Lys Cys Leu Thr Leu Ala Thr
        35                  40                  45

Ala Val Val Gln Leu Tyr Leu Ala Leu Pro Pro Gly Ala Glu His Trp
    50                  55                  60

Thr Lys Glu His Cys Gly Ala Val Cys Phe Val Lys Asp Asn Pro Gln
65                  70                  75                  80

Lys Ser Tyr Phe Ile Arg Leu Tyr Gly Leu Gln Ala Gly Arg Leu Leu
                85                  90                  95

Trp Glu Gln Glu Leu Tyr Ser Gln Leu Val Tyr Ser Thr Pro Thr Pro
            100                 105                 110

Phe Phe His Thr Phe Ala Gly Asp Asp Cys Gln Ala Gly Leu Asn Phe
        115                 120                 125

Ala Asp Glu Asp Glu Ala Gln Ala Phe Arg Ala Leu Val Gln Glu Lys
    130                 135                 140

Ile Gln Lys Arg Asn Gln Arg Gln Ser Gly Asp Arg Arg Gln Leu Pro
145                 150                 155                 160

Pro Pro Pro Thr Pro Ala Asn Glu Glu Arg Arg Gly Gly Leu Pro Pro
                165                 170                 175

Leu Pro Leu His Pro Gly Gly Asp Gln Gly Gly Pro Pro Val Gly Pro
            180                 185                 190

Leu Ser Leu Gly Leu Ala Thr Val Asp Ile Gln Asn Pro Asp Ile Thr
        195                 200                 205

Ser Ser Arg Tyr Arg Gly Leu Pro Ala Pro Gly Pro Ser Pro Ala Asp
    210                 215                 220

Lys Lys Arg Ser Gly Lys Lys Lys Ile Ser Lys Ala Asp Ile Gly Ala
225                 230                 235                 240

Pro Ser Gly Phe Lys His Val Ser His Val Gly Trp Asp Pro Gln Asn
                245                 250                 255

Gly Phe Asp Val Asn Asn Leu Asp Pro Asp Leu Arg Ser Leu Phe Ser
            260                 265                 270

Arg Ala Gly Ile Ser Glu Ala Gln Leu Thr Asp Ala Glu Thr Ser Lys
        275                 280                 285

Leu Ile Tyr Asp Phe Ile Glu Asp Gln Gly Gly Leu Glu Ala Val Arg
    290                 295                 300

Gln Glu Met Arg Arg Gln Glu Pro Leu Pro Pro Pro Pro Pro Pro Ser
305                 310                 315                 320
```

```
                    -continued

Arg Gly Gly Asn Gln Leu Pro Arg Pro Pro Ile Val Gly Gly Asn Lys
                325                 330                 335

Gly Arg Ser Gly Pro Leu Pro Val Pro Leu Gly Ile Ala Pro Pro
            340                 345                 350

Pro Pro Thr Pro Arg Gly Pro Pro Pro Gly Arg Gly Pro Pro
            355                 360                 365

Pro Pro Pro Pro Ala Thr Gly Arg Ser Gly Pro Leu Pro Pro Pro
370                 375                 380

Pro Pro Gly Ala Gly Pro Pro Met Pro Pro Pro Pro Pro
385                 390                 395                 400

Pro Pro Pro Pro Ser Ser Gly Asn Gly Pro Ala Pro Pro Leu Pro
                405                 410                 415

Pro Ala Leu Val Pro Ala Gly Gly Leu Ala Pro Gly Gly Arg Gly
                420                 425                 430

Ala Leu Leu Asp Gln Ile Arg Gln Gly Ile Gln Leu Asn Lys Thr Pro
            435                 440                 445

Gly Ala Pro Glu Ser Ser Ala Leu Gln Pro Pro Gln Ser Ser Glu
    450                 455                 460

Gly Leu Val Gly Ala Leu Met His Val Met Gln Lys Arg Ser Arg Ala
465                 470                 475                 480

Ile His Ser Ser Asp Glu Gly Glu Asp Gln Ala Gly Asp Glu Asp Glu
                485                 490                 495

Asp Asp Glu Trp Asp Asp
            500

<210> SEQ ID NO 3
<211> LENGTH: 297
<212> TYPE: DNA
<213> ORGANISM: Artificial sequence
<220> FEATURE:
<223> OTHER INFORMATION: Description of the artificial sequence:
      Fragment of the human WASP protein
<220> FEATURE:
<221> NAME/KEY: CDS
<222> LOCATION: (1)..(297)

<400> SEQUENCE: 3 ccc agc tcc ggg aat gga cca gcc cct ccc cca ctc cct cct gct ctg        48
Pro Ser Ser Gly Asn Gly Pro Ala Pro Pro Leu Pro Pro Ala Leu
  1               5                  10                  15 gtg cct gcc ggg ggc ctg gcc cct ggt ggg ggt cgg gga gcg ctt ttg        96
Val Pro Ala Gly Gly Leu Ala Pro Gly Gly Gly Arg Gly Ala Leu Leu
                 20                  25                  30 gat caa atc cgg cag gga att cag ctg aac aag acc cct ggg gcc cca       144
Asp Gln Ile Arg Gln Gly Ile Gln Leu Asn Lys Thr Pro Gly Ala Pro
             35                  40                  45 gag agc tca gcg ctg cag cca cca cct cag agc tca gag gga ctg gtg       192
Glu Ser Ser Ala Leu Gln Pro Pro Pro Gln Ser Ser Glu Gly Leu Val
         50                  55                  60 ggg gcc ctg atg cac gtg atg cag aag aga agc aga gcc atc cac tcc       240
Gly Ala Leu Met His Val Met Gln Lys Arg Ser Arg Ala Ile His Ser
 65                  70                  75                  80 tcc gac gaa ggg gag gac cag gct ggc gat gaa gat gaa gat gat gaa       288
Ser Asp Glu Gly Glu Asp Gln Ala Gly Asp Glu Asp Glu Asp Asp Glu
                 85                  90                  95 tgg gat gac                                                            297
Trp Asp Asp

<210> SEQ ID NO 4
```

-continued

```
<211> LENGTH: 99
<212> TYPE: PRT
<213> ORGANISM: Artificial sequence
<220> FEATURE:
<223> OTHER INFORMATION: Description of the artificial sequence:
      Fragment of the human WASP protein

<400> SEQUENCE: 4

Pro Ser Ser Gly Asn Gly Pro Ala Pro Pro Leu Pro Pro Ala Leu
 1               5                  10                  15

Val Pro Ala Gly Gly Leu Ala Pro Gly Gly Gly Arg Gly Ala Leu Leu
            20                  25                  30

Asp Gln Ile Arg Gln Gly Ile Gln Leu Asn Lys Thr Pro Gly Ala Pro
        35                  40                  45

Glu Ser Ser Ala Leu Gln Pro Pro Pro Gln Ser Ser Glu Gly Leu Val
    50                  55                  60

Gly Ala Leu Met His Val Met Gln Lys Arg Ser Arg Ala Ile His Ser
65                  70                  75                  80

Ser Asp Glu Gly Glu Asp Gln Ala Gly Asp Glu Asp Glu Asp Asp Glu
                85                  90                  95
Trp Asp Asp

<210> SEQ ID NO 5
<211> LENGTH: 252
<212> TYPE: DNA
<213> ORGANISM: Artificial sequence
<220> FEATURE:
<223> OTHER INFORMATION: Description of the artificial sequence:
      Fragment of the human WASP protein
<220> FEATURE:
<221> NAME/KEY: CDS
<222> LOCATION: (1)..(252)

<400> SEQUENCE: 5 ccc agc tcc ggg aat gga cca gcc cct ccc cca ctc cct cct gct ctg     48
Pro Ser Ser Gly Asn Gly Pro Ala Pro Pro Leu Pro Pro Ala Leu
 1               5                  10                  15 gtg cct gcc ggg ggc ctg gcc cct ggt ggg ggt cgg gga gcg ctt ttg     96
Val Pro Ala Gly Gly Leu Ala Pro Gly Gly Gly Arg Gly Ala Leu Leu
            20                  25                  30 gat caa atc cgg cag gga att cag ctg aac aag acc cct ggg gcc cca    144
Asp Gln Ile Arg Gln Gly Ile Gln Leu Asn Lys Thr Pro Gly Ala Pro
        35                  40                  45 gag agc tca gcg ctg cag cca cca cct cag agc tca gag gga ctg gtg    192
Glu Ser Ser Ala Leu Gln Pro Pro Pro Gln Ser Ser Glu Gly Leu Val
    50                  55                  60 ggg gcc ctg atg cac gtg atg cag aag aga agc aga gcc atc cac tcc    240
Gly Ala Leu Met His Val Met Gln Lys Arg Ser Arg Ala Ile His Ser
65                  70                  75                  80 tcc gac gaa ggg                                                    252
Ser Asp Glu Gly <210> SEQ ID NO 6
<211> LENGTH: 84
<212> TYPE: PRT
<213> ORGANISM: Artificial sequence
<220> FEATURE:
<223> OTHER INFORMATION: Description of the artificial sequence:
      Fragment of the human WASP protein

<400> SEQUENCE: 6

Pro Ser Ser Gly Asn Gly Pro Ala Pro Pro Leu Pro Pro Ala Leu
 1               5                  10                  15
```

```
Val Pro Ala Gly Gly Leu Ala Pro Gly Gly Arg Gly Ala Leu Leu
            20                  25                  30

Asp Gln Ile Arg Gln Gly Ile Gln Leu Asn Lys Thr Pro Gly Ala Pro
            35                  40                  45

Glu Ser Ser Ala Leu Gln Pro Pro Gln Ser Ser Glu Gly Leu Val
 50                      55                  60

Gly Ala Leu Met His Val Met Gln Lys Arg Ser Arg Ala Ile His Ser
 65                  70                  75                  80
Ser Asp Glu Gly

<210> SEQ ID NO 7
<211> LENGTH: 219
<212> TYPE: DNA
<213> ORGANISM: Artificial sequence
<220> FEATURE:
<223> OTHER INFORMATION: Description of the artificial sequence:
      Fragment of the human WASP protein
<220> FEATURE:
<221> NAME/KEY: CDS
<222> LOCATION: (1)..(219)

<400> SEQUENCE: 7 ggt cgg gga gcg ctt ttg gat caa atc cgg cag gga att cag ctg aac      48
Gly Arg Gly Ala Leu Leu Asp Gln Ile Arg Gln Gly Ile Gln Leu Asn
 1               5                  10                  15 aag acc cct ggg gcc cca gag agc tca gcg ctg cag cca cca cct cag     96
Lys Thr Pro Gly Ala Pro Glu Ser Ser Ala Leu Gln Pro Pro Pro Gln
            20                  25                  30 agc tca gag gga ctg gtg ggg gcc ctg atg cac gtg atg cag aag aga    144
Ser Ser Glu Gly Leu Val Gly Ala Leu Met His Val Met Gln Lys Arg
        35                  40                  45 agc aga gcc atc cac tcc tcc gac gaa ggg gag gac cag gct ggc gat    192
Ser Arg Ala Ile His Ser Ser Asp Glu Gly Glu Asp Gln Ala Gly Asp
    50                  55                  60 gaa gat gaa gat gat gaa tgg gat gac                                 219
Glu Asp Glu Asp Asp Glu Trp Asp Asp
 65                  70

<210> SEQ ID NO 8
<211> LENGTH: 73
<212> TYPE: PRT
<213> ORGANISM: Artificial sequence
<220> FEATURE:
<223> OTHER INFORMATION: Description of the artificial sequence:
      Fragment of the human WASP protein

<400> SEQUENCE: 8

Gly Arg Gly Ala Leu Leu Asp Gln Ile Arg Gln Gly Ile Gln Leu Asn
 1               5                  10                  15

Lys Thr Pro Gly Ala Pro Glu Ser Ser Ala Leu Gln Pro Pro Pro Gln
            20                  25                  30

Ser Ser Glu Gly Leu Val Gly Ala Leu Met His Val Met Gln Lys Arg
        35                  40                  45

Ser Arg Ala Ile His Ser Ser Asp Glu Gly Glu Asp Gln Ala Gly Asp
    50                  55                  60

Glu Asp Glu Asp Asp Glu Trp Asp Asp
 65                  70

<210> SEQ ID NO 9
<211> LENGTH: 174
<212> TYPE: DNA
<213> ORGANISM: Artificial sequence
<220> FEATURE:
```

<223> OTHER INFORMATION: Description of the artificial sequence:
      Fragment of the human WASP protein
<220> FEATURE:
<221> NAME/KEY: CDS
<222> LOCATION: (1)..(174)

<400> SEQUENCE: 9

```
ggt cgg gga gcg ctt ttg gat caa atc cgg cag gga att cag ctg aac      48
Gly Arg Gly Ala Leu Leu Asp Gln Ile Arg Gln Gly Ile Gln Leu Asn
 1               5                  10                  15 aag acc cct ggg gcc cca gag agc tca gcg ctg cag cca cca cct cag      96
Lys Thr Pro Gly Ala Pro Glu Ser Ser Ala Leu Gln Pro Pro Pro Gln
                 20                  25                  30 agc tca gag gga ctg gtg ggg gcc ctg atg cac gtg atg cag aag aga     144
Ser Ser Glu Gly Leu Val Gly Ala Leu Met His Val Met Gln Lys Arg
             35                  40                  45 agc aga gcc atc cac tcc tcc gac gaa ggg                             174
Ser Arg Ala Ile His Ser Ser Asp Glu Gly
         50                  55
```

<210> SEQ ID NO 10
<211> LENGTH: 58
<212> TYPE: PRT
<213> ORGANISM: Artificial sequence
<220> FEATURE:
<223> OTHER INFORMATION: Description of the artificial sequence:
      Fragment of the human WASP protein

<400> SEQUENCE: 10

```
Gly Arg Gly Ala Leu Leu Asp Gln Ile Arg Gln Gly Ile Gln Leu Asn
 1               5                  10                  15

Lys Thr Pro Gly Ala Pro Glu Ser Ser Ala Leu Gln Pro Pro Pro Gln
                 20                  25                  30

Ser Ser Glu Gly Leu Val Gly Ala Leu Met His Val Met Gln Lys Arg
             35                  40                  45

Ser Arg Ala Ile His Ser Ser Asp Glu Gly
         50                  55
```

<210> SEQ ID NO 11
<211> LENGTH: 1518
<212> TYPE: DNA
<213> ORGANISM: Homosapiens
<220> FEATURE:
<221> NAME/KEY: CDS
<222> LOCATION: (1)..(1518)

<400> SEQUENCE: 11

```
atg agc tcc gtc cag cag cag ccg ccg ccg ccg cgg agg gtc acc aac      48
Met Ser Ser Val Gln Gln Gln Pro Pro Pro Pro Arg Arg Val Thr Asn
 1               5                  10                  15 gtg ggg tcc ctg ttg ctc acc ccg cag gag aac gag tcc ctc ttc act      96
Val Gly Ser Leu Leu Leu Thr Pro Gln Glu Asn Glu Ser Leu Phe Thr
                 20                  25                  30 ttc ctc ggc aag aaa tgt gtg act atg tct tca gca gtg gtg cag tta     144
Phe Leu Gly Lys Lys Cys Val Thr Met Ser Ser Ala Val Val Gln Leu
             35                  40                  45 tat gca gca gat cgg aac tgt atg tgg tca aag aag tgc agt ggt gtt     192
Tyr Ala Ala Asp Arg Asn Cys Met Trp Ser Lys Lys Cys Ser Gly Val
         50                  55                  60 gct tgt ctt gtt aag gac aat cca cag aga tct cat ttt tta aga ata     240
Ala Cys Leu Val Lys Asp Asn Pro Gln Arg Ser His Phe Leu Arg Ile
 65                  70                  75                  80
```

```
ttt gac att aag gat ggg aaa cta ttg tgg gaa caa gag cta tac aat        288
Phe Asp Ile Lys Asp Gly Lys Leu Leu Trp Glu Gln Glu Leu Tyr Asn
                 85                  90                  95 aac ttt gta tat aat agt cct aga gga tat ttt cat acc ttt gct gga        336
Asn Phe Val Tyr Asn Ser Pro Arg Gly Tyr Phe His Thr Phe Ala Gly
            100                 105                 110 gat act tgt caa gtt gct ctt aat ttt gcc aat gaa gaa gaa gca aaa        384
Asp Thr Cys Gln Val Ala Leu Asn Phe Ala Asn Glu Glu Glu Ala Lys
        115                 120                 125 aaa ttt cga aaa gca gtt aca gac ctt ttg ggc cgt cga caa agg aaa        432
Lys Phe Arg Lys Ala Val Thr Asp Leu Leu Gly Arg Arg Gln
Arg Lys     130                 135                 140 tct gag aaa aga cga gat ccc cca aat ggt cct aat cta ccc atg gct        480
Ser Glu Lys Arg Arg Asp Pro Pro Asn Gly Pro Asn Leu Pro Met Ala
145             150                 155                 160 aca gtt gat ata aaa aat cca gaa atc aca aca aat aga ttt tat ggt        528
Thr Val Asp Ile Lys Asn Pro Glu Ile Thr Thr Asn Arg Phe Tyr Gly
                165                 170                 175 cca caa gtc aac aac atc tcc cat acc aaa gaa aag aag aag gga aaa        576
Pro Gln Val Asn Asn Ile Ser His Thr Lys Glu Lys Lys Lys Gly Lys
            180                 185                 190 gct aaa aag aag aga tta acc aag gga gat ata gga aca cca agc aat        624
Ala Lys Lys Lys Arg Leu Thr Lys Gly Asp Ile Gly Thr Pro Ser Asn
        195                 200                 205 ttc cag cac att gga cat gtt ggt tgg gat cca aat aca ggc tct gat        672
Phe Gln His Ile Gly His Val Gly Trp Asp Pro Asn Thr Gly Ser Asp
    210                 215                 220 ctg aat aat ttg gat cca gaa ttg aag aat ctt ttt gat atg tgt gga        720
Leu Asn Asn Leu Asp Pro Glu Leu Lys Asn Leu Phe Asp Met Cys Gly
225                 230                 235                 240 atc tta gag gca caa ctt aaa gaa aga gaa aca tta aaa gtt ata tat        768
Ile Leu Glu Ala Gln Leu Lys Glu Arg Glu Thr Leu Lys Val Ile Tyr
                245                 250                 255 gac ttt att gaa aaa aca gga ggt gtt gaa gct gtt aaa aat gaa ctg        816
Asp Phe Ile Glu Lys Thr Gly Gly Val Glu Ala Val Lys Asn Glu Leu
            260                 265                 270 cgg agg caa gca cca cca cct cca cca cca tca agg gga ggg cca cct        864
Arg Arg Gln Ala Pro Pro Pro Pro Pro Ser Arg Gly Gly Pro Pro
        275                 280                 285 cct cct cct ccc cct cca cat agc tcg ggt cct cct cct cct cct gct        912
Pro Pro Pro Pro Pro Pro His Ser Ser Gly Pro Pro Pro Pro Pro Ala
    290                 295                 300 agg gga aga ggc gct cct ccc cca cca cct tca aga gct ccc aca gct        960
Arg Gly Arg Gly Ala Pro Pro Pro Pro Ser Arg Ala Pro Thr Ala
305             310                 315                 320 gca cct cca cca ccg cct cct tcc agg cca agt gta gaa gtc cct cca       1008
Ala Pro Pro Pro Pro Pro Ser Arg Pro Ser Val Glu Val Pro Pro
                325                 330                 335 cca ccg cca aat agg atg tac cct cct cca cct cca gcc ctt ccc tcc       1056
Pro Pro Pro Asn Arg Met Tyr Pro Pro Pro Pro Ala Leu Pro Ser
            340                 345                 350 tca gca cct tca ggg cct cca cca cca cct cca tct gtg ttg ggg gta       1104
Ser Ala Pro Ser Gly Pro Pro Pro Pro Pro Pro Ser Val Leu Gly Val
        355                 360                 365 ggg cca gtg gca cca ccc cca ccg cct cca cct cca cct cct cct ggg       1152
Gly Pro Val Ala Pro Pro Pro Pro Pro Pro Pro Pro Pro Pro Pro Gly
    370                 375                 380 cca ccg ccc ccg cct ggc ctg cct tct gat ggg gac cat cag gtt cca       1200
Pro Pro Pro Pro Pro Gly Leu Pro Ser Asp Gly Asp His Gln Val Pro
```

-continued

```
                385                 390                 395                 400
act act gca gga aac aaa gca gct ctt tta gat caa att aga gag ggt         1248
Thr Thr Ala Gly Asn Lys Ala Ala Leu Leu Asp Gln Ile Arg Glu Gly
                    405                 410                 415 gct cag cta aaa aaa gtg gag cag aac agt cgg cca gtg tcc tgc tct         1296
Ala Gln Leu Lys Lys Val Glu Gln Asn Ser Arg Pro Val Ser Cys Ser
            420                 425                 430 gga cga gat gca ctg tta gac cag ata cga cag ggt atc caa cta aaa         1344
Gly Arg Asp Ala Leu Leu Asp Gln Ile Arg Gln Gly Ile Gln Leu Lys
        435                 440                 445 tct gtg gct gat ggc caa gag tct aca cca cca aca cct gca ccc act         1392
Ser Val Ala Asp Gly Gln Glu Ser Thr Pro Pro Thr Pro Ala Pro Thr
    450                 455                 460 tca gga att gtg ggt gca tta atg gaa gtg atg cag aaa agg agc aaa         1440
Ser Gly Ile Val Gly Ala Leu Met Glu Val Met Gln Lys Arg Ser Lys
465                 470                 475                 480 gcc att cat tct tca gat gaa gat gaa gat gaa gat gat gaa gaa gat         1488
Ala Ile His Ser Ser Asp Glu Asp Glu Asp Glu Asp Asp Glu Glu Asp
                    485                 490                 495 ttt gag gat gat gat gag tgg gaa gac tga                                 1518
Phe Glu Asp Asp Asp Glu Trp Glu Asp
                500                 505

<210> SEQ ID NO 12
<211> LENGTH: 505
<212> TYPE: PRT
<213> ORGANISM: Homo sapiens

<400> SEQUENCE: 12

Met Ser Ser Val Gln Gln Pro Pro Pro Arg Arg Val Thr Asn
  1               5                  10                  15

Val Gly Ser Leu Leu Leu Thr Pro Gln Glu Asn Glu Ser Leu Phe Thr
                 20                  25                  30

Phe Leu Gly Lys Lys Cys Val Thr Met Ser Ser Ala Val Val Gln Leu
             35                  40                  45

Tyr Ala Ala Asp Arg Asn Cys Met Trp Ser Lys Lys Cys Ser Gly Val
         50                  55                  60

Ala Cys Leu Val Lys Asp Asn Pro Gln Arg Ser His Phe Leu Arg Ile
 65                  70                  75                  80

Phe Asp Ile Lys Asp Gly Lys Leu Leu Trp Glu Gln Glu Leu Tyr Asn
                 85                  90                  95

Asn Phe Val Tyr Asn Ser Pro Arg Gly Tyr Phe His Thr Phe Ala Gly
            100                 105                 110

Asp Thr Cys Gln Val Ala Leu Asn Phe Ala Asn Glu Glu Glu Ala Lys
        115                 120                 125

Lys Phe Arg Lys Ala Val Thr Asp Leu Leu Gly Arg Arg Gln Arg Lys
    130                 135                 140

Ser Glu Lys Arg Arg Asp Pro Pro Asn Gly Pro Asn Leu Pro Met Ala
145                 150                 155                 160

Thr Val Asp Ile Lys Asn Pro Glu Ile Thr Thr Asn Arg Phe Tyr Gly
                165                 170                 175

Pro Gln Val Asn Asn Ile Ser His Thr Lys Glu Lys Lys Lys Gly Lys
            180                 185                 190

Ala Lys Lys Lys Arg Leu Thr Lys Gly Asp Ile Gly Thr Pro Ser Asn
        195                 200                 205

Phe Gln His Ile Gly His Val Gly Trp Asp Pro Asn Thr Gly Ser Asp
    210                 215                 220
```

```
Leu Asn Asn Leu Asp Pro Glu Leu Lys Asn Leu Phe Asp Met Cys Gly
225                 230                 235                 240

Ile Leu Glu Ala Gln Leu Lys Glu Arg Glu Thr Leu Lys Val Ile Tyr
                245                 250                 255

Asp Phe Ile Glu Lys Thr Gly Gly Val Glu Ala Val Lys Asn Glu Leu
                260                 265                 270

Arg Arg Gln Ala Pro Pro Pro Pro Ser Arg Gly Gly Pro Pro
            275                 280                 285

Pro Pro Pro Pro Pro His Ser Ser Gly Pro Pro Pro Pro Ala
    290                 295                 300

Arg Gly Arg Gly Ala Pro Pro Pro Ser Arg Ala Pro Thr Ala
305                 310                 315                 320

Ala Pro Pro Pro Pro Pro Ser Arg Pro Ser Val Glu Val Pro Pro
                325                 330                 335

Pro Pro Pro Asn Arg Met Tyr Pro Pro Pro Pro Ala Leu Pro Ser
            340                 345                 350

Ser Ala Pro Ser Gly Pro Pro Pro Pro Pro Ser Val Leu Gly Val
        355                 360                 365

Gly Pro Val Ala Pro Pro Pro Pro Pro Pro Pro Pro Pro Gly
    370                 375                 380

Pro Pro Pro Pro Gly Leu Pro Ser Asp Gly Asp His Gln Val Pro
385                 390                 395                 400

Thr Thr Ala Gly Asn Lys Ala Ala Leu Leu Asp Gln Ile Arg Glu Gly
                405                 410                 415

Ala Gln Leu Lys Lys Val Glu Gln Asn Ser Arg Pro Val Ser Cys Ser
                420                 425                 430

Gly Arg Asp Ala Leu Leu Asp Gln Ile Arg Gln Gly Ile Gln Leu Lys
            435                 440                 445

Ser Val Ala Asp Gly Gln Glu Ser Thr Pro Pro Thr Pro Ala Pro Thr
    450                 455                 460

Ser Gly Ile Val Gly Ala Leu Met Glu Val Met Gln Lys Arg Ser Lys
465                 470                 475                 480

Ala Ile His Ser Ser Asp Glu Asp Glu Asp Asp Glu Glu Asp
                485                 490                 495

Phe Glu Asp Asp Glu Trp Glu Asp
            500                 505

<210> SEQ ID NO 13
<211> LENGTH: 342
<212> TYPE: DNA
<213> ORGANISM: Artificial sequence
<220> FEATURE:
<223> OTHER INFORMATION: Description of the artificial sequence:
      Fragment of the human N-WASP protein
<220> FEATURE:
<221> NAME/KEY: CDS
<222> LOCATION: (1)..(342)

<400> SEQUENCE: 13 cct tct gat ggg gac cat cag gtt cca act act gca gga aac aaa gca        48
Pro Ser Asp Gly Asp His Gln Val Pro Thr Thr Ala Gly Asn Lys Ala
  1               5                  10                  15 gct ctt tta gat caa att aga gag ggt gct cag cta aaa aaa gtg gag        96
Ala Leu Leu Asp Gln Ile Arg Glu Gly Ala Gln Leu Lys Lys Val Glu
             20                  25                  30 cag aac agt cgg cca gtg tcc tgc tct gga cga gat gca ctg tta gac       144
Gln Asn Ser Arg Pro Val Ser Cys Ser Gly Arg Asp Ala Leu Leu Asp
```

```
                35                  40                  45
cag ata cga cag ggt atc caa cta aaa tct gtg gct gat ggc caa gag      192
Gln Ile Arg Gln Gly Ile Gln Leu Lys Ser Val Ala Asp Gly Gln Glu
    50                  55                  60 tct aca cca cca aca cct gca ccc act tca gga att gtg ggt gca tta      240
Ser Thr Pro Pro Thr Pro Ala Pro Thr Ser Gly Ile Val Gly Ala Leu
65                  70                  75                  80 atg gaa gtg atg cag aaa agg agc aaa gcc att cat tct tca gat gaa      288
Met Glu Val Met Gln Lys Arg Ser Lys Ala Ile His Ser Ser Asp Glu
                85                  90                  95 gat gaa gat gaa gat gat gaa gaa gat ttt gag gat gat gat gag tgg      336
Asp Glu Asp Glu Asp Asp Glu Glu Asp Phe Glu Asp Asp Asp Glu Trp
            100                 105                 110 gaa gac                                                              342
Glu Asp
```

<210> SEQ ID NO 14
<211> LENGTH: 114
<212> TYPE: PRT
<213> ORGANISM: Artificial sequence
<220> FEATURE:
<223> OTHER INFORMATION: Description of the artificial sequence:
      Fragment of the human N-WASP protein

<400> SEQUENCE: 14

```
Pro Ser Asp Gly Asp His Gln Val Pro Thr Thr Ala Gly Asn Lys Ala
 1               5                  10                  15

Ala Leu Leu Asp Gln Ile Arg Glu Gly Ala Gln Leu Lys Lys Val Glu
            20                  25                  30

Gln Asn Ser Arg Pro Val Ser Cys Ser Gly Arg Asp Ala Leu Leu Asp
        35                  40                  45

Gln Ile Arg Gln Gly Ile Gln Leu Lys Ser Val Ala Asp Gly Gln Glu
    50                  55                  60

Ser Thr Pro Pro Thr Pro Ala Pro Thr Ser Gly Ile Val Gly Ala Leu
65                  70                  75                  80

Met Glu Val Met Gln Lys Arg Ser Lys Ala Ile His Ser Ser Asp Glu
                85                  90                  95

Asp Glu Asp Glu Asp Asp Glu Glu Asp Phe Glu Asp Asp Asp Glu Trp
            100                 105                 110
Glu Asp
```

<210> SEQ ID NO 15
<211> LENGTH: 291
<212> TYPE: DNA
<213> ORGANISM: Artificial sequence
<220> FEATURE:
<223> OTHER INFORMATION: Description of the artificial sequence:
      Fragment of the human N-WASP protein
<220> FEATURE:
<221> NAME/KEY: CDS
<222> LOCATION: (1)..(291)

<400> SEQUENCE: 15

```
cct tct gat ggg gac cat cag gtt cca act act gca gga aac aaa gca       48
Pro Ser Asp Gly Asp His Gln Val Pro Thr Thr Ala Gly Asn Lys Ala
 1               5                  10                  15 gct ctt tta gat caa att aga gag ggt gct cag cta aaa aaa gtg gag       96
Ala Leu Leu Asp Gln Ile Arg Glu Gly Ala Gln Leu Lys Lys Val Glu
            20                  25                  30 cag aac agt cgg cca gtg tcc tgc tct gga cga gat gca ctg tta gac      144
Gln Asn Ser Arg Pro Val Ser Cys Ser Gly Arg Asp Ala Leu Leu Asp
        35                  40                  45
```

```
cag ata cga cag ggt atc caa cta aaa tct gtg gct gat ggc caa gag      192
Gln Ile Arg Gln Gly Ile Gln Leu Lys Ser Val Ala Asp Gly Gln Glu
 50                  55                  60 tct aca cca cca aca cct gca ccc act tca gga att gtg ggt gca tta      240
Ser Thr Pro Pro Thr Pro Ala Pro Thr Ser Gly Ile Val Gly Ala Leu
 65                  70                  75                  80 atg gaa gtg atg cag aaa agg agc aaa gcc att cat tct tca gat gaa      288
Met Glu Val Met Gln Lys Arg Ser Lys Ala Ile His Ser Ser Asp Glu
                 85                  90                  95 gat                                                                  291
Asp

<210> SEQ ID NO 16
<211> LENGTH: 97
<212> TYPE: PRT
<213> ORGANISM: Artificial sequence
<220> FEATURE:
<223> OTHER INFORMATION: Description of the artificial sequence:
      Fragment of the human N-WASP protein

<400> SEQUENCE: 16

Pro Ser Asp Gly Asp His Gln Val Pro Thr Thr Ala Gly Asn Lys Ala
 1               5                  10                  15

Ala Leu Leu Asp Gln Ile Arg Glu Gly Ala Gln Leu Lys Lys Val Glu
                20                  25                  30

Gln Asn Ser Arg Pro Val Ser Cys Ser Gly Arg Asp Ala Leu Leu Asp
            35                  40                  45

Gln Ile Arg Gln Gly Ile Gln Leu Lys Ser Val Ala Asp Gly Gln Glu
 50                  55                  60

Ser Thr Pro Pro Thr Pro Ala Pro Thr Ser Gly Ile Val Gly Ala Leu
 65                  70                  75                  80

Met Glu Val Met Gln Lys Arg Ser Lys Ala Ile His Ser Ser Asp Glu
                 85                  90                  95
Asp

<210> SEQ ID NO 17
<211> LENGTH: 303
<212> TYPE: DNA
<213> ORGANISM: Artificial sequence
<220> FEATURE:
<223> OTHER INFORMATION: Description of the artificial sequence:
      Fragment of the human N-WASP protein
<220> FEATURE:
<221> NAME/KEY: CDS
<222> LOCATION: (1)..(303)

<400> SEQUENCE: 17 aac aaa gca gct ctt tta gat caa att aga gag ggt gct cag cta aaa      48
Asn Lys Ala Ala Leu Leu Asp Gln Ile Arg Glu Gly Ala Gln Leu Lys
 1               5                  10                  15 aaa gtg gag cag aac agt cgg cca gtg tcc tgc tct gga cga gat gca      96
Lys Val Glu Gln Asn Ser Arg Pro Val Ser Cys Ser Gly Arg Asp Ala
                20                  25                  30 ctg tta gac cag ata cga cag ggt atc caa cta aaa tct gtg gct gat     144
Leu Leu Asp Gln Ile Arg Gln Gly Ile Gln Leu Lys Ser Val Ala Asp
            35                  40                  45 ggc caa gag tct aca cca cca aca cct gca ccc act tca gga att gtg     192
Gly Gln Glu Ser Thr Pro Pro Thr Pro Ala Pro Thr Ser Gly Ile Val
 50                  55                  60 ggt gca tta atg gaa gtg atg cag aaa agg agc aaa gcc att cat tct     240
Gly Ala Leu Met Glu Val Met Gln Lys Arg Ser Lys Ala Ile His Ser
 65                  70                  75                  80
```

```
tca gat gaa gat gaa gat gaa gat gat gaa gaa gat ttt gag gat gat      288
Ser Asp Glu Asp Glu Asp Glu Asp Asp Glu Glu Asp Phe Glu Asp Asp
                85                  90                  95 gat gag tgg gaa gac                                                  303
Asp Glu Trp Glu Asp
        100
```

<210> SEQ ID NO 18
<211> LENGTH: 101
<212> TYPE: PRT
<213> ORGANISM: Artificial sequence
<220> FEATURE:
<223> OTHER INFORMATION: Description of the artificial sequence:
      Fragment of the human N-WASP protein

<400> SEQUENCE: 18

```
Asn Lys Ala Ala Leu Leu Asp Gln Ile Arg Glu Gly Ala Gln Leu Lys
 1               5                  10                  15

Lys Val Glu Gln Asn Ser Arg Pro Val Ser Cys Ser Gly Arg Asp Ala
                20                  25                  30

Leu Leu Asp Gln Ile Arg Gln Gly Ile Gln Leu Lys Ser Val Ala Asp
            35                  40                  45

Gly Gln Glu Ser Thr Pro Pro Thr Pro Ala Pro Thr Ser Gly Ile Val
 50                  55                  60

Gly Ala Leu Met Glu Val Met Gln Lys Arg Ser Lys Ala Ile His Ser
 65                  70                  75                  80

Ser Asp Glu Asp Glu Asp Glu Asp Asp Glu Glu Asp Phe Glu Asp Asp
                85                  90                  95

Asp Glu Trp Glu Asp
        100
```

<210> SEQ ID NO 19
<211> LENGTH: 252
<212> TYPE: DNA
<213> ORGANISM: Artificial sequence
<220> FEATURE:
<223> OTHER INFORMATION: Description of the artificial sequence:
      Fragment of the human N-WASP protein
<220> FEATURE:
<221> NAME/KEY: CDS
<222> LOCATION: (1)..(252)

<400> SEQUENCE: 19

```
aac aaa gca gct ctt tta gat caa att aga gag ggt gct cag cta aaa       48
Asn Lys Ala Ala Leu Leu Asp Gln Ile Arg Glu Gly Ala Gln Leu Lys
 1               5                  10                  15 aaa gtg gag cag aac agt cgg cca gtg tcc tgc tct gga cga gat gca       96
Lys Val Glu Gln Asn Ser Arg Pro Val Ser Cys Ser Gly Arg Asp Ala
                20                  25                  30 ctg tta gac cag ata cga cag ggt atc caa cta aaa tct gtg gct gat      144
Leu Leu Asp Gln Ile Arg Gln Gly Ile Gln Leu Lys Ser Val Ala Asp
            35                  40                  45 ggc caa gag tct aca cca cca aca cct gca ccc act tca gga att gtg      192
Gly Gln Glu Ser Thr Pro Pro Thr Pro Ala Pro Thr Ser Gly Ile Val
 50                  55                  60 ggt gca tta atg gaa gtg atg cag aaa agg agc aaa gcc att cat tct      240
Gly Ala Leu Met Glu Val Met Gln Lys Arg Ser Lys Ala Ile His Ser
 65                  70                  75                  80 tca gat gaa gat                                                      252
Ser Asp Glu Asp
```

-continued

<210> SEQ ID NO 20
<211> LENGTH: 84
<212> TYPE: PRT
<213> ORGANISM: Artificial sequence
<220> FEATURE:
<223> OTHER INFORMATION: Description of the artificial sequence:
      Fragment of the human N-WASP protein

<400> SEQUENCE: 20

Asn Lys Ala Ala Leu Leu Asp Gln Ile Arg Glu Gly Ala Gln Leu Lys
 1               5                  10                  15

Lys Val Glu Gln Asn Ser Arg Pro Val Ser Cys Ser Gly Arg Asp Ala
                20                  25                  30

Leu Leu Asp Gln Ile Arg Gln Gly Ile Gln Leu Lys Ser Val Ala Asp
            35                  40                  45

Gly Gln Glu Ser Thr Pro Pro Thr Pro Ala Pro Thr Ser Gly Ile Val
        50                  55                  60

Gly Ala Leu Met Glu Val Met Gln Lys Arg Ser Lys Ala Ile His Ser
65                  70                  75                  80
Ser Asp Glu Asp

<210> SEQ ID NO 21
<211> LENGTH: 219
<212> TYPE: DNA
<213> ORGANISM: Artificial sequence
<220> FEATURE:
<223> OTHER INFORMATION: Description of the artificial sequence:
      Fragment of the human N-WASP protein
<220> FEATURE:
<221> NAME/KEY: CDS
<222> LOCATION: (1)..(219)

<400> SEQUENCE: 21 gga cga gat gca ctg tta gac cag ata cga cag ggt atc caa cta aaa        48
Gly Arg Asp Ala Leu Leu Asp Gln Ile Arg Gln Gly Ile Gln Leu Lys
 1               5                  10                  15 tct gtg gct gat ggc caa gag tct aca cca cca aca cct gca ccc act        96
Ser Val Ala Asp Gly Gln Glu Ser Thr Pro Pro Thr Pro Ala Pro Thr
                20                  25                  30 tca gga att gtg ggt gca tta atg gaa gtg atg cag aaa agg agc aaa       144
Ser Gly Ile Val Gly Ala Leu Met Glu Val Met Gln Lys Arg Ser Lys
            35                  40                  45 gcc att cat tct tca gat gaa gat gaa gat gaa gat gat gaa gaa gat       192
Ala Ile His Ser Ser Asp Glu Asp Glu Asp Glu Asp Asp Glu Glu Asp
        50                  55                  60 ttt gag gat gat gat gag tgg gaa gac                                   219
Phe Glu Asp Asp Asp Glu Trp Glu Asp
65                  70

<210> SEQ ID NO 22
<211> LENGTH: 73
<212> TYPE: PRT
<213> ORGANISM: Artificial sequence
<220> FEATURE:
<223> OTHER INFORMATION: Description of the artificial sequence:
      Fragment of the human N-WASP protein

<400> SEQUENCE: 22

Gly Arg Asp Ala Leu Leu Asp Gln Ile Arg Gln Gly Ile Gln Leu Lys
 1               5                  10                  15

Ser Val Ala Asp Gly Gln Glu Ser Thr Pro Pro Thr Pro Ala Pro Thr
                20                  25                  30

Ser Gly Ile Val Gly Ala Leu Met Glu Val Met Gln Lys Arg Ser Lys
            35                  40                  45

```
Ala Ile His Ser Ser Asp Glu Asp Glu Asp Asp Glu Glu Asp
    50                  55                  60

Phe Glu Asp Asp Asp Glu Trp Glu Asp
65                  70

<210> SEQ ID NO 23
<211> LENGTH: 168
<212> TYPE: DNA
<213> ORGANISM: Artificial sequence
<220> FEATURE:
<223> OTHER INFORMATION: Description of the artificial sequence:
      Fragment of the human N-WASP protein
<220> FEATURE:
<221> NAME/KEY: CDS
<222> LOCATION: (1)..(168)

<400> SEQUENCE: 23 gga cga gat gca ctg tta gac cag ata cga cag ggt atc caa cta aaa    48
Gly Arg Asp Ala Leu Leu Asp Gln Ile Arg Gln Gly Ile Gln Leu Lys
1               5                   10                  15 tct gtg gct gat ggc caa gag tct aca cca cca aca cct gca ccc act    96
Ser Val Ala Asp Gly Gln Glu Ser Thr Pro Pro Thr Pro Ala Pro Thr
            20                  25                  30 tca gga att gtg ggt gca tta atg gaa gtg atg cag aaa agg agc aaa   144
Ser Gly Ile Val Gly Ala Leu Met Glu Val Met Gln Lys Arg Ser Lys
        35                  40                  45 gcc att cat tct tca gat gaa gat                                    168
Ala Ile His Ser Ser Asp Glu Asp
    50                  55

<210> SEQ ID NO 24
<211> LENGTH: 56
<212> TYPE: PRT
<213> ORGANISM: Artificial sequence
<220> FEATURE:
<223> OTHER INFORMATION: Description of the artificial sequence:
      Fragment of the human N-WASP protein

<400> SEQUENCE: 24

Gly Arg Asp Ala Leu Leu Asp Gln Ile Arg Gln Gly Ile Gln Leu Lys
1               5                   10                  15

Ser Val Ala Asp Gly Gln Glu Ser Thr Pro Pro Thr Pro Ala Pro Thr
            20                  25                  30

Ser Gly Ile Val Gly Ala Leu Met Glu Val Met Gln Lys Arg Ser Lys
        35                  40                  45

Ala Ile His Ser Ser Asp Glu Asp
    50                  55

<210> SEQ ID NO 25
<211> LENGTH: 1758
<212> TYPE: DNA
<213> ORGANISM: Homo sapiens
<220> FEATURE:
<221> NAME/KEY: CDS
<222> LOCATION: (1)..(1677)

<400> SEQUENCE: 25 atg ccg cta gtg aaa aga aac atc gat cct agg cac ttg tgc cac aca    48
Met Pro Leu Val Lys Arg Asn Ile Asp Pro Arg His Leu Cys His Thr
1               5                   10                  15 gca ctg cct aga ggc att aag aat gaa ctg gaa tgt gta acc aat att    96
Ala Leu Pro Arg Gly Ile Lys Asn Glu Leu Glu Cys Val Thr Asn Ile
            20                  25                  30
```

```
tcc ttg gca aat ata att aga caa cta agt agc cta agt aaa tat gct    144
Ser Leu Ala Asn Ile Ile Arg Gln Leu Ser Ser Leu Ser Lys Tyr Ala
         35                  40                  45 gaa gat ata ttt gga gaa tta ttc aat gaa gca cat agt ttt tcc ttc    192
Glu Asp Ile Phe Gly Glu Leu Phe Asn Glu Ala His Ser Phe Ser Phe
 50                  55                  60 aga gtc aac tca ttg caa gaa cgt gtg gac cgt tta tct gtt agt gtt    240
Arg Val Asn Ser Leu Gln Glu Arg Val Asp Arg Leu Ser Val Ser Val
 65                  70                  75                  80 aca cag ctt gat cca aag gaa gaa gaa ttg tct ttg caa gat ata aca    288
Thr Gln Leu Asp Pro Lys Glu Glu Glu Leu Ser Leu Gln Asp Ile Thr
                 85                  90                  95 atg agg aaa gct ttc cga agt tct aca att caa gac cag cag ctt ttc    336
Met Arg Lys Ala Phe Arg Ser Ser Thr Ile Gln Asp Gln Gln Leu Phe
            100                 105                 110 gat cgc aag act ttg cct att cca tta cag gag acg tac gat gtt tgt    384
Asp Arg Lys Thr Leu Pro Ile Pro Leu Gln Glu Thr Tyr Asp Val Cys
            115                 120                 125 gaa cag cct cca cct ctc aat ata ctc act cct tat aga gat gat ggt    432
Glu Gln Pro Pro Pro Leu Asn Ile Leu Thr Pro Tyr Arg Asp Asp Gly
        130                 135                 140 aaa gaa ggt ctg aag ttt tat acc aat cct tcg tat ttc ttt gat cta    480
Lys Glu Gly Leu Lys Phe Tyr Thr Asn Pro Ser Tyr Phe Phe Asp Leu
145                 150                 155                 160 tgg aaa gaa aaa atg ttg caa gat aca gag gat aag agg aag gaa aag    528
Trp Lys Glu Lys Met Leu Gln Asp Thr Glu Asp Lys Arg Lys Glu Lys
                165                 170                 175 agg aag cag aag cag aaa aat cta gat cgt cct cat gaa cca gaa aaa    576
Arg Lys Gln Lys Gln Lys Asn Leu Asp Arg Pro His Glu Pro Glu Lys
            180                 185                 190 gtg cca aga gca cct cat gac agg cgg cga gaa tgg cag aag ctg gcc    624
Val Pro Arg Ala Pro His Asp Arg Arg Arg Glu Trp Gln Lys Leu Ala
            195                 200                 205 caa ggt cca gag ctg gct gaa gat gat gct aat ctc tta cat aag cat    672
Gln Gly Pro Glu Leu Ala Glu Asp Asp Ala Asn Leu Leu His Lys His
        210                 215                 220 att gaa gtt gct aat ggc cca gcc tct cat ttt gaa aca aga cct cag    720
Ile Glu Val Ala Asn Gly Pro Ala Ser His Phe Glu Thr Arg Pro Gln
225                 230                 235                 240 aca tac gtg gat cat atg gat gga tct tac tca ctt tct gcc ttg cca    768
Thr Tyr Val Asp His Met Asp Gly Ser Tyr Ser Leu Ser Ala Leu Pro
                245                 250                 255 ttt agt cag atg agt gag ctt ctg act aga gct gag gaa agg gta tta    816
Phe Ser Gln Met Ser Glu Leu Leu Thr Arg Ala Glu Glu Arg Val Leu
            260                 265                 270 gtc aga cca cat gaa cca cct cca cct cca cca atg cat gga gca gga    864
Val Arg Pro His Glu Pro Pro Pro Pro Pro Met His Gly Ala Gly
            275                 280                 285 gat gca aaa ccg ata ccc acc tgt atc agt tct gct aca ggt ttg ata    912
Asp Ala Lys Pro Ile Pro Thr Cys Ile Ser Ser Ala Thr Gly Leu Ile
        290                 295                 300 gaa aat cgc cct cag tca cca gct aca ggc aga aca cct gtg ttt gtg    960
Glu Asn Arg Pro Gln Ser Pro Ala Thr Gly Arg Thr Pro Val Phe Val
305                 310                 315                 320 agc ccc act ccc cca cct cct cca cca cct ctt cca tct gcc ttg tca    1008
Ser Pro Thr Pro Pro Pro Pro Pro Pro Leu Pro Ser Ala Leu Ser
                325                 330                 335 act tcc tca tta aga gct tca atg act tca act cct ccc cct cca gta    1056
Thr Ser Ser Leu Arg Ala Ser Met Thr Ser Thr Pro Pro Pro Pro Val
            340                 345                 350
```

```
cct ccc cca cct cca cct cca gcc act gct ttg caa gct cca gca gta      1104
Pro Pro Pro Pro Pro Pro Pro Ala Thr Ala Leu Gln Ala Pro Ala Val
        355                 360                 365 cca cca cct cca gct cct ctt cag att gcc cct gga gtt ctt cac cca      1152
Pro Pro Pro Pro Ala Pro Leu Gln Ile Ala Pro Gly Val Leu His Pro
    370                 375                 380 gct cct cct cca att gca cct cct cta gta cag ccc tct cca cca gta      1200
Ala Pro Pro Pro Ile Ala Pro Pro Leu Val Gln Pro Ser Pro Pro Val
385                 390                 395                 400 gct aga gct gcc cca gta tgt gag act gta cca gtt cat cca ctc cca      1248
Ala Arg Ala Ala Pro Val Cys Glu Thr Val Pro Val His Pro Leu Pro
                405                 410                 415 caa ggt gaa gtt cag ggg ctg cct cca ccc cca ccg cct cct ctg          1296
Gln Gly Glu Val Gln Gly Leu Pro Pro Pro Pro Pro Pro Pro Leu
            420                 425                 430 cct cca cct ggc att cga cca tca tca cct gtc aca gtt aca gct ctt      1344
Pro Pro Pro Gly Ile Arg Pro Ser Ser Pro Val Thr Val Thr Ala Leu
        435                 440                 445 gct cat cct ccc tct ggg cta cat cca act cca tct act gcc cca ggt      1392
Ala His Pro Pro Ser Gly Leu His Pro Thr Pro Ser Thr Ala Pro Gly
    450                 455                 460 ccc cat gtt cca tta atg cct cca tct cct cca tca caa gtt ata cct      1440
Pro His Val Pro Leu Met Pro Pro Ser Pro Pro Ser Gln Val Ile Pro
465                 470                 475                 480 gct tct gag cca aag cgc cat cca tca acc cta cct gta atc agt gat      1488
Ala Ser Glu Pro Lys Arg His Pro Ser Thr Leu Pro Val Ile Ser Asp
                485                 490                 495 gcc agg agt gtg cta ctg gaa gca ata cga aaa ggt att cag cta cgc      1536
Ala Arg Ser Val Leu Leu Glu Ala Ile Arg Lys Gly Ile Gln Leu Arg
            500                 505                 510 aaa gta gaa gag cag cgt gaa cag gaa gct aag cat gaa cgc att gaa      1584
Lys Val Glu Glu Gln Arg Glu Gln Glu Ala Lys His Glu Arg Ile Glu
        515                 520                 525 aac gat gtt gcc acc atc ctg tct cgc cgt att gct gtt gaa tat agt      1632
Asn Asp Val Ala Thr Ile Leu Ser Arg Arg Ile Ala Val Glu Tyr Ser
    530                 535                 540 gat tcg gaa gat gat tca gaa ttt gat gaa gta gat tgg ttg gag          1677
Asp Ser Glu Asp Asp Ser Glu Phe Asp Glu Val Asp Trp Leu Glu
545                 550                 555 taagaaaaat gcattgataa atattacaaa actgaatgca aatgtccttt gtggtgcttg    1737
ttccttgaaa atgtttggtc a                                              1758

<210> SEQ ID NO 26
<211> LENGTH: 559
<212> TYPE: PRT
<213> ORGANISM: Homo sapiens

<400> SEQUENCE: 26

Met Pro Leu Val Lys Arg Asn Ile Asp Pro Arg His Leu Cys His Thr
1               5                   10                  15

Ala Leu Pro Arg Gly Ile Lys Asn Glu Leu Glu Cys Val Thr Asn Ile
            20                  25                  30

Ser Leu Ala Asn Ile Ile Arg Gln Leu Ser Ser Leu Ser Lys Tyr Ala
        35                  40                  45

Glu Asp Ile Phe Gly Glu Leu Phe Asn Glu Ala His Ser Phe Ser Phe
    50                  55                  60

Arg Val Asn Ser Leu Gln Glu Arg Val Asp Arg Leu Ser Val Ser Val
65                  70                  75                  80
```

```
Thr Gln Leu Asp Pro Lys Glu Glu Leu Ser Leu Gln Asp Ile Thr
                85                  90                  95

Met Arg Lys Ala Phe Arg Ser Ser Thr Ile Gln Asp Gln Leu Phe
            100                 105                 110

Asp Arg Lys Thr Leu Pro Ile Pro Leu Gln Glu Thr Tyr Asp Val Cys
            115                 120                 125

Glu Gln Pro Pro Pro Leu Asn Ile Leu Thr Pro Tyr Arg Asp Asp Gly
    130                 135                 140

Lys Glu Gly Leu Lys Phe Tyr Thr Asn Pro Ser Tyr Phe Phe Asp Leu
145                 150                 155                 160

Trp Lys Glu Lys Met Leu Gln Asp Thr Glu Asp Lys Arg Lys Glu Lys
                165                 170                 175

Arg Lys Gln Lys Gln Lys Asn Leu Asp Arg Pro His Glu Pro Glu Lys
            180                 185                 190

Val Pro Arg Ala Pro His Asp Arg Arg Glu Trp Gln Lys Leu Ala
    195                 200                 205

Gln Gly Pro Glu Leu Ala Glu Asp Asp Ala Asn Leu Leu His Lys His
    210                 215                 220

Ile Glu Val Ala Asn Gly Pro Ala Ser His Phe Glu Thr Arg Pro Gln
225                 230                 235                 240

Thr Tyr Val Asp His Met Asp Gly Ser Tyr Ser Leu Ser Ala Leu Pro
                245                 250                 255

Phe Ser Gln Met Ser Glu Leu Leu Thr Arg Ala Glu Glu Arg Val Leu
            260                 265                 270

Val Arg Pro His Glu Pro Pro Pro Pro Met His Gly Ala Gly
    275                 280                 285

Asp Ala Lys Pro Ile Pro Thr Cys Ile Ser Ser Ala Thr Gly Leu Ile
    290                 295                 300

Glu Asn Arg Pro Gln Ser Pro Ala Thr Gly Arg Thr Pro Val Phe Val
305                 310                 315                 320

Ser Pro Thr Pro Pro Pro Pro Pro Leu Pro Ser Ala Leu Ser
                325                 330                 335

Thr Ser Ser Leu Arg Ala Ser Met Thr Ser Thr Pro Pro Pro Val
            340                 345                 350

Pro Pro Pro Pro Pro Pro Ala Thr Ala Leu Gln Ala Pro Ala Val
            355                 360                 365

Pro Pro Pro Pro Ala Pro Leu Gln Ile Ala Pro Gly Val Leu His Pro
    370                 375                 380

Ala Pro Pro Pro Ile Ala Pro Pro Leu Val Gln Pro Ser Pro Pro Val
385                 390                 395                 400

Ala Arg Ala Ala Pro Val Cys Glu Thr Val Pro Val His Pro Leu Pro
                405                 410                 415

Gln Gly Glu Val Gln Gly Leu Pro Pro Pro Pro Pro Pro Leu
            420                 425                 430

Pro Pro Pro Gly Ile Arg Pro Ser Ser Pro Val Thr Val Thr Ala Leu
            435                 440                 445

Ala His Pro Pro Ser Gly Leu His Pro Thr Pro Ser Thr Ala Pro Gly
    450                 455                 460

Pro His Val Pro Leu Met Pro Pro Ser Pro Ser Gln Val Ile Pro
465                 470                 475                 480

Ala Ser Glu Pro Lys Arg His Pro Ser Thr Leu Pro Val Ile Ser Asp
                485                 490                 495
```

```
Ala Arg Ser Val Leu Glu Ala Ile Arg Lys Gly Ile Gln Leu Arg
            500                 505                 510

Lys Val Glu Glu Gln Arg Glu Gln Glu Ala Lys His Glu Arg Ile Glu
        515                 520                 525

Asn Asp Val Ala Thr Ile Leu Ser Arg Arg Ile Ala Val Glu Tyr Ser
        530                 535                 540

Asp Ser Glu Asp Asp Ser Glu Phe Asp Glu Val Asp Trp Leu Glu
545                 550                 555

<210> SEQ ID NO 27
<211> LENGTH: 351
<212> TYPE: DNA
<213> ORGANISM: Artificial sequence
<220> FEATURE:
<223> OTHER INFORMATION: Description of the artificial sequence:
      Fragment of the human Scar1 protein
<220> FEATURE:
<221> NAME/KEY: CDS
<222> LOCATION: (1)..(351)

<400> SEQUENCE: 27
```

| gtc aca gtt aca gct ctt gct cat cct ccc tct ggg cta cat cca act | 48 |
| Val Thr Val Thr Ala Leu Ala His Pro Pro Ser Gly Leu His Pro Thr | |
|  1               5                  10                  15      | |

| cca tct act gcc cca ggt ccc cat gtt cca tta atg cct cca tct cct | 96 |
| Pro Ser Thr Ala Pro Gly Pro His Val Pro Leu Met Pro Pro Ser Pro | |
|             20                  25                  30          | |

| cca tca caa gtt ata cct gct tct gag cca aag cgc cat cca tca acc | 144 |
| Pro Ser Gln Val Ile Pro Ala Ser Glu Pro Lys Arg His Pro Ser Thr | |
|         35                  40                  45              | |

| cta cct gta atc agt gat gcc agg agt gtg cta ctg gaa gca ata cga | 192 |
| Leu Pro Val Ile Ser Asp Ala Arg Ser Val Leu Leu Glu Ala Ile Arg | |
|     50                  55                  60                  | |

| aaa ggt att cag cta cgc aaa gta gaa gag cag cgt gaa cag gaa gct | 240 |
| Lys Gly Ile Gln Leu Arg Lys Val Glu Glu Gln Arg Glu Gln Glu Ala | |
| 65                  70                  75                  80  | |

| aag cat gaa cgc att gaa aac gat gtt gcc acc atc ctg tct cgc cgt | 288 |
| Lys His Glu Arg Ile Glu Asn Asp Val Ala Thr Ile Leu Ser Arg Arg | |
|                 85                  90                  95      | |

| att gct gtt gaa tat agt gat tcg gaa gat gat tca gaa ttt gat gaa | 336 |
| Ile Ala Val Glu Tyr Ser Asp Ser Glu Asp Asp Ser Glu Phe Asp Glu | |
|             100                 105                 110         | |

| gta gat tgg ttg gag | 351 |
| Val Asp Trp Leu Glu |     |
|         115         |     |

```
<210> SEQ ID NO 28
<211> LENGTH: 117
<212> TYPE: PRT
<213> ORGANISM: Artificial sequence
<220> FEATURE:
<223> OTHER INFORMATION: Description of the artificial sequence:
      Fragment of the human Scar1 protein

<400> SEQUENCE: 28

Val Thr Val Thr Ala Leu Ala His Pro Pro Ser Gly Leu His Pro Thr
 1               5                  10                  15

Pro Ser Thr Ala Pro Gly Pro His Val Pro Leu Met Pro Pro Ser Pro
            20                  25                  30

Pro Ser Gln Val Ile Pro Ala Ser Glu Pro Lys Arg His Pro Ser Thr
        35                  40                  45

Leu Pro Val Ile Ser Asp Ala Arg Ser Val Leu Leu Glu Ala Ile Arg
```

```
                50               55                  60
Lys Gly Ile Gln Leu Arg Lys Val Glu Glu Gln Arg Glu Gln Glu Ala
 65                  70                  75                  80

Lys His Glu Arg Ile Glu Asn Asp Val Ala Thr Ile Leu Ser Arg Arg
                 85                  90                  95

Ile Ala Val Glu Tyr Ser Asp Ser Asp Asp Ser Glu Phe Asp Glu
            100                 105                 110

Val Asp Trp Leu Glu
        115

<210> SEQ ID NO 29
<211> LENGTH: 312
<212> TYPE: DNA
<213> ORGANISM: Artificial sequence
<220> FEATURE:
<223> OTHER INFORMATION: Description of the artificial sequence:
      Fragment of the human Scar1 protein
<220> FEATURE:
<221> NAME/KEY: CDS
<222> LOCATION: (1)..(312)

<400> SEQUENCE: 29 gtc aca gtt aca gct ctt gct cat cct ccc tct ggg cta cat cca act      48
Val Thr Val Thr Ala Leu Ala His Pro Pro Ser Gly Leu His Pro Thr
  1               5                  10                  15 cca tct act gcc cca ggt ccc cat gtt cca tta atg cct cca tct cct      96
Pro Ser Thr Ala Pro Gly Pro His Val Pro Leu Met Pro Pro Ser Pro
                 20                  25                  30 cca tca caa gtt ata cct gct tct gag cca aag cgc cat cca tca acc     144
Pro Ser Gln Val Ile Pro Ala Ser Glu Pro Lys Arg His Pro Ser Thr
             35                  40                  45 cta cct gta atc agt gat gcc agg agt gtg cta ctg gaa gca ata cga     192
Leu Pro Val Ile Ser Asp Ala Arg Ser Val Leu Leu Glu Ala Ile Arg
         50                  55                  60 aaa ggt att cag cta cgc aaa gta gaa gag cag cgt gaa cag gaa gct     240
Lys Gly Ile Gln Leu Arg Lys Val Glu Glu Gln Arg Glu Gln Glu Ala
 65                  70                  75                  80 aag cat gaa cgc att gaa aac gat gtt gcc acc atc ctg tct cgc cgt     288
Lys His Glu Arg Ile Glu Asn Asp Val Ala Thr Ile Leu Ser Arg Arg
                 85                  90                  95 att gct gtt gaa tat agt gat tcg                                    312
Ile Ala Val Glu Tyr Ser Asp Ser
            100

<210> SEQ ID NO 30
<211> LENGTH: 104
<212> TYPE: PRT
<213> ORGANISM: Artificial sequence
<220> FEATURE:
<223> OTHER INFORMATION: Description of the artificial sequence:
      Fragment of the human Scar1 protein

<400> SEQUENCE: 30

Val Thr Val Thr Ala Leu Ala His Pro Pro Ser Gly Leu His Pro Thr
  1               5                  10                  15

Pro Ser Thr Ala Pro Gly Pro His Val Pro Leu Met Pro Pro Ser Pro
                 20                  25                  30

Pro Ser Gln Val Ile Pro Ala Ser Glu Pro Lys Arg His Pro Ser Thr
             35                  40                  45

Leu Pro Val Ile Ser Asp Ala Arg Ser Val Leu Leu Glu Ala Ile Arg
         50                  55                  60
```

```
Lys Gly Ile Gln Leu Arg Lys Val Glu Glu Gln Arg Glu Gln Glu Ala
 65                  70                  75                  80

Lys His Glu Arg Ile Glu Asn Asp Val Ala Thr Ile Leu Ser Arg Arg
                 85                  90                  95

Ile Ala Val Glu Tyr Ser Asp Ser
                100
```

<210> SEQ ID NO 31
<211> LENGTH: 189
<212> TYPE: DNA
<213> ORGANISM: Artificial sequence
<220> FEATURE:
<223> OTHER INFORMATION: Description of the artificial sequence:
      Fragment of the human Scar1 protein
<220> FEATURE:
<221> NAME/KEY: CDS
<222> LOCATION: (1)..(189)

<400> SEQUENCE: 31

```
gcc agg agt gtg cta ctg gaa gca ata cga aaa ggt att cag cta cgc      48
Ala Arg Ser Val Leu Leu Glu Ala Ile Arg Lys Gly Ile Gln Leu Arg
  1               5                  10                  15 aaa gta gaa gag cag cgt gaa cag gaa gct aag cat gaa cgc att gaa      96
Lys Val Glu Glu Gln Arg Glu Gln Glu Ala Lys His Glu Arg Ile Glu
                 20                  25                  30 aac gat gtt gcc acc atc ctg tct cgc cgt att gct gtt gaa tat agt     144
Asn Asp Val Ala Thr Ile Leu Ser Arg Arg Ile Ala Val Glu Tyr Ser
             35                  40                  45 gat tcg gaa gat gat tca gaa ttt gat gaa gta gat tgg ttg gag         189
Asp Ser Glu Asp Asp Ser Glu Phe Asp Glu Val Asp Trp Leu Glu
         50                  55                  60
```

<210> SEQ ID NO 32
<211> LENGTH: 63
<212> TYPE: PRT
<213> ORGANISM: Artificial sequence
<220> FEATURE:
<223> OTHER INFORMATION: Description of the artificial sequence:
      Fragment of the human Scar1 protein

<400> SEQUENCE: 32

```
Ala Arg Ser Val Leu Leu Glu Ala Ile Arg Lys Gly Ile Gln Leu Arg
  1               5                  10                  15

Lys Val Glu Glu Gln Arg Glu Gln Glu Ala Lys His Glu Arg Ile Glu
                 20                  25                  30

Asn Asp Val Ala Thr Ile Leu Ser Arg Arg Ile Ala Val Glu Tyr Ser
             35                  40                  45

Asp Ser Glu Asp Asp Ser Glu Phe Asp Glu Val Asp Trp Leu Glu
         50                  55                  60
```

<210> SEQ ID NO 33
<211> LENGTH: 150
<212> TYPE: DNA
<213> ORGANISM: Artificial sequence
<220> FEATURE:
<223> OTHER INFORMATION: Description of the artificial sequence:
      Fragment of the human Scar1 protein
<220> FEATURE:
<221> NAME/KEY: CDS
<222> LOCATION: (1)..(150)

<400> SEQUENCE: 33

```
gcc agg agt gtg cta ctg gaa gca ata cga aaa ggt att cag cta cgc      48
Ala Arg Ser Val Leu Leu Glu Ala Ile Arg Lys Gly Ile Gln Leu Arg
  1               5                  10                  15
```

```
aaa gta gaa gag cag cgt gaa cag gaa gct aag cat gaa cgc att gaa      96
Lys Val Glu Glu Gln Arg Glu Gln Glu Ala Lys His Glu Arg Ile Glu
             20                  25                  30 aac gat gtt gcc acc atc ctg tct cgc cgt att gct gtt gaa tat agt     144
Asn Asp Val Ala Thr Ile Leu Ser Arg Arg Ile Ala Val Glu Tyr Ser
         35                  40                  45 gat tcg                                                             150
Asp Ser
     50

<210> SEQ ID NO 34
<211> LENGTH: 50
<212> TYPE: PRT
<213> ORGANISM: Artificial sequence
<220> FEATURE:
<223> OTHER INFORMATION: Description of the artificial sequence:
      Fragment of the human Scar1 protein

<400> SEQUENCE: 34

Ala Arg Ser Val Leu Leu Glu Ala Ile Arg Lys Gly Ile Gln Leu Arg
 1               5                  10                  15

Lys Val Glu Glu Gln Arg Glu Gln Glu Ala Lys His Glu Arg Ile Glu
             20                  25                  30

Asn Asp Val Ala Thr Ile Leu Ser Arg Arg Ile Ala Val Glu Tyr Ser
         35                  40                  45

Asp Ser
     50

<210> SEQ ID NO 35
<211> LENGTH: 2069
<212> TYPE: DNA
<213> ORGANISM: Mus musculus
<220> FEATURE:
<221> NAME/KEY: CDS
<222> LOCATION: (25)..(1584)

<400> SEQUENCE: 35
agcaggacta aggcagaagg cagc atg aat agt ggc cct ggc cct gta gga      51
                          Met Asn Ser Gly Pro Gly Pro Val Gly
                           1               5 ggc agg cct ggg gga cga ggg gga cca gcc gtt cag cag aac att cct     99
Gly Arg Pro Gly Gly Arg Gly Gly Pro Ala Val Gln Gln Asn Ile Pro
 10                  15                  20                  25 tcc aac ctc ctc cag gac cat gaa aac cag aga ctc ttt gag ctt ctt    147
Ser Asn Leu Leu Gln Asp His Glu Asn Gln Arg Leu Phe Glu Leu Leu
                 30                  35                  40 ggc cga aaa tgc tgg aca ctg gct acc aca gtt gtt cag ctc tac ctg    195
Gly Arg Lys Cys Trp Thr Leu Ala Thr Thr Val Val Gln Leu Tyr Leu
             45                  50                  55 gca ctg ccc cct gga gct gag cac tgg acc atg gaa cac tgc ggg gct    243
Ala Leu Pro Pro Gly Ala Glu His Trp Thr Met Glu His Cys Gly Ala
         60                  65                  70 gtg tgc ttc gtg aag gat aac cct cag aag tcc tac ttc atc cgc ctt    291
Val Cys Phe Val Lys Asp Asn Pro Gln Lys Ser Tyr Phe Ile Arg Leu
 75                  80                  85 tat gcg cta cag gct ggt cgg cta ctc tgg gaa cag gag ctg tac tct    339
Tyr Ala Leu Gln Ala Gly Arg Leu Leu Trp Glu Gln Glu Leu Tyr Ser
 90                  95                 100                 105 cag ctg gtt tat ctc act ccc acc ccg ttc ttc cac act ttt gct gga    387
Gln Leu Val Tyr Leu Thr Pro Thr Pro Phe Phe His Thr Phe Ala Gly
                110                 115                 120
```

```
gat gac tgt caa gta gga ctg aac ttt gcg gat gag agt gaa gcc cag      435
Asp Asp Cys Gln Val Gly Leu Asn Phe Ala Asp Glu Ser Glu Ala Gln
            125                 130                 135 gcc ttc cgg gcc ttg gtg cag gag aag ata caa aaa agg aat cag agg      483
Ala Phe Arg Ala Leu Val Gln Glu Lys Ile Gln Lys Arg Asn Gln Arg
        140                 145                 150 caa agc gga gaa aga cgc cag cta cca cca cca gca cca atc aat          531
Gln Ser Gly Glu Arg Arg Gln Leu Pro Pro Pro Ala Pro Ile Asn
    155                 160                 165 gag gag aga aga gga ggg ctc cca cct gtg ccc cca cac ccg ggt gga      579
Glu Glu Arg Arg Gly Gly Leu Pro Pro Val Pro Pro His Pro Gly Gly
170                 175                 180                 185 gat cat ggg ggc cca tca ggt ggt cca cta tct cta gga ctt gtg acg      627
Asp His Gly Gly Pro Ser Gly Gly Pro Leu Ser Leu Gly Leu Val Thr
            190                 195                 200 gtc gac att cag aac cct gac atc aca agt tca cga tac cgt ggg ctc      675
Val Asp Ile Gln Asn Pro Asp Ile Thr Ser Ser Arg Tyr Arg Gly Leu
        205                 210                 215 cct gca cct ggc cct ggc cca act gat aag aaa cgc tca ggg aaa aag      723
Pro Ala Pro Gly Pro Gly Pro Thr Asp Lys Lys Arg Ser Gly Lys Lys
    220                 225                 230 aag atc agc aaa gct gat atc gga gca ccg agt gga ttc aaa cat gtc      771
Lys Ile Ser Lys Ala Asp Ile Gly Ala Pro Ser Gly Phe Lys His Val
235                 240                 245 agc cac gtg ggc tgg gat ccc cag aat gga ttt gat gtg aac aac cta      819
Ser His Val Gly Trp Asp Pro Gln Asn Gly Phe Asp Val Asn Asn Leu
250                 255                 260                 265 gac ccg gat ctg cgg agc ttg ttc tcc agg gca gga atc agc gag gcc      867
Asp Pro Asp Leu Arg Ser Leu Phe Ser Arg Ala Gly Ile Ser Glu Ala
            270                 275                 280 cag ctc act gac gca gag acc tcc aag ctc atc tac gat ttt att gag      915
Gln Leu Thr Asp Ala Glu Thr Ser Lys Leu Ile Tyr Asp Phe Ile Glu
        285                 290                 295 gac cag gga ggt cta gag gct gtc cgg cag gag atg agg cgc caa gag      963
Asp Gln Gly Gly Leu Glu Ala Val Arg Gln Glu Met Arg Arg Gln Glu
    300                 305                 310 cca ctc cca cca cct ccg ccg cca tgc aga gga gga gga gga gga         1011
Pro Leu Pro Pro Pro Pro Pro Pro Cys Arg Gly Gly Gly Gly Gly
315                 320                 325 gga gga gga gga gga gga gga gga gga gga ggc cag cct ctg aga         1059
Gly Gly Gly Gly Gly Gly Gly Gly Gly Gly Gly Gln Pro Leu Arg
330                 335                 340                 345 cct cct gtt ttg ggg agt aat aag ggt cgc tca cct cca ctg ccc cct      1107
Pro Pro Val Leu Gly Ser Asn Lys Gly Arg Ser Pro Pro Leu Pro Pro
            350                 355                 360 gta cct atg ggg ggt gcc cca cct cca cca aca cca cga ggg ccc cca     1155
Val Pro Met Gly Gly Ala Pro Pro Pro Pro Thr Pro Arg Gly Pro Pro
        365                 370                 375 cca cca ggc cga ggg ggt cct cct cca cca ccc cct cca gcc act gga     1203
Pro Pro Gly Arg Gly Gly Pro Pro Pro Pro Pro Pro Ala Thr Gly
    380                 385                 390 cga tct gga cca cca cct cct cca ctc cct gga gct ggg gga cca cca     1251
Arg Ser Gly Pro Pro Pro Pro Pro Leu Pro Gly Ala Gly Gly Pro Pro
395                 400                 405 gca ccg cca cca cca cca cca cca cca cct cca ccc tgc cct ggg         1299
Ala Pro Pro Pro Pro Pro Pro Pro Pro Pro Pro Pro Cys Pro Gly
410                 415                 420                 425 agt gga ccc gcc cct ccc ccg ctc cct cct act cca gtg tct ggg ggg     1347
Ser Gly Pro Ala Pro Pro Pro Leu Pro Pro Thr Pro Val Ser Gly Gly
            430                 435                 440
```

```
agc cca gca cct ggt ggg ggc cgg ggt gca ctt ttg gac caa atc cgg       1395
Ser Pro Ala Pro Gly Gly Gly Arg Gly Ala Leu Leu Asp Gln Ile Arg
            445                 450                 455 cag gga att cag ctg aac aag acc cct gga gct cta gag aac tca gta       1443
Gln Gly Ile Gln Leu Asn Lys Thr Pro Gly Ala Leu Glu Asn Ser Val
        460                 465                 470 cag caa cca ccc gcg cag cag tca gaa ggc cta gta ggt gcc ctg atg       1491
Gln Gln Pro Pro Ala Gln Gln Ser Glu Gly Leu Val Gly Ala Leu Met
475                 480                 485 cat gtc atg cag aag agg agt aga gtc atc cat tcc tca gat gaa ggg       1539
His Val Met Gln Lys Arg Ser Arg Val Ile His Ser Ser Asp Glu Gly
490                 495                 500                 505 gag gat cag acc ggc gag gat gaa gag gat gat gaa tgg gat gac           1584
Glu Asp Gln Thr Gly Glu Asp Glu Glu Asp Asp Glu Trp Asp Asp
            510                 515                 520 taaagtcatc ttccttccag caagccagtt cctctccaca ctcactctgc catctagatt      1644
ctgctcccgc tggcagcttc ccaattcacc tgttggggaa cctcataccc aatctaaagt      1704
acacatgacg tcacctttca cctctcataa ctcagggatg aaacaggata aaattgagtc      1764
tatgtgtctg agtgtgtgtt cattcacatc ctaaatgagt agtttgggtt tctttccctc      1824
acagtccctt ttggctttga tcttgctttg tgtgttttta ttgagccttt cacaagtatg      1884
atctattatt cctttaagat ttcagccata gccgggtgtg gtggcgcacg cctttaattc      1944
cagcagaagg gaggcagagg caggtggatt tctgagttcg agaccagcct ggtctacaga      2004
gtgagttcca ggacagccag ggctatacag agaaaccctg tctcaaaaaa ccaaaaaaaa      2064
aaaaa                                                                  2069

<210> SEQ ID NO 36
<211> LENGTH: 520
<212> TYPE: PRT
<213> ORGANISM: Mus musculus

<400> SEQUENCE: 36

Met Asn Ser Gly Pro Gly Pro Val Gly Gly Arg Pro Gly Gly Arg Gly
1               5                   10                  15

Gly Pro Ala Val Gln Gln Asn Ile Pro Ser Asn Leu Leu Gln Asp His
            20                  25                  30

Glu Asn Gln Arg Leu Phe Glu Leu Leu Gly Arg Lys Cys Trp Thr Leu
        35                  40                  45

Ala Thr Thr Val Val Gln Leu Tyr Leu Ala Leu Pro Pro Gly Ala Glu
    50                  55                  60

His Trp Thr Met Glu His Cys Gly Ala Val Cys Phe Lys Asp Asn
65              70                  75                  80

Pro Gln Lys Ser Tyr Phe Ile Arg Leu Tyr Ala Leu Gln Ala Gly Arg
                85                  90                  95

Leu Leu Trp Glu Gln Glu Leu Tyr Ser Gln Leu Val Tyr Leu Thr Pro
            100                 105                 110

Thr Pro Phe Phe His Thr Phe Ala Gly Asp Asp Cys Gln Val Gly Leu
        115                 120                 125

Asn Phe Ala Asp Glu Ser Glu Ala Gln Ala Phe Arg Ala Leu Val Gln
    130                 135                 140

Glu Lys Ile Gln Lys Arg Asn Gln Arg Gln Ser Gly Glu Arg Arg Gln
145                 150                 155                 160

Leu Pro Pro Pro Pro Ala Pro Ile Asn Glu Glu Arg Arg Gly Gly Leu
                165                 170                 175
```

```
Pro Pro Val Pro Pro His Pro Gly Gly Asp His Gly Gly Pro Ser Gly
        180                 185                 190

Gly Pro Leu Ser Leu Gly Leu Val Thr Val Asp Ile Gln Asn Pro Asp
        195                 200                 205

Ile Thr Ser Ser Arg Tyr Arg Gly Leu Pro Ala Pro Gly Pro Gly Pro
        210                 215                 220

Thr Asp Lys Lys Arg Ser Gly Lys Lys Ile Ser Lys Ala Asp Ile
225                 230                 235                 240

Gly Ala Pro Ser Gly Phe Lys His Val Ser His Val Gly Trp Asp Pro
                245                 250                 255

Gln Asn Gly Phe Asp Val Asn Asn Leu Asp Pro Asp Leu Arg Ser Leu
                260                 265                 270

Phe Ser Arg Ala Gly Ile Ser Glu Ala Gln Leu Thr Asp Ala Glu Thr
            275                 280                 285

Ser Lys Leu Ile Tyr Asp Phe Ile Glu Asp Gln Gly Gly Leu Glu Ala
        290                 295                 300

Val Arg Gln Glu Met Arg Arg Gln Glu Pro Leu Pro Pro Pro Pro Pro
305                 310                 315                 320

Pro Cys Arg Gly Gly Gly Gly Gly Gly Gly Gly Gly Gly Gly Gly
                325                 330                 335

Gly Gly Gly Gly Gly Gln Pro Leu Arg Pro Pro Val Leu Gly Ser Asn
                340                 345                 350

Lys Gly Arg Ser Pro Pro Leu Pro Pro Val Pro Met Gly Gly Ala Pro
                355                 360                 365

Pro Pro Pro Thr Pro Arg Gly Pro Pro Pro Gly Arg Gly Gly Pro
        370                 375                 380

Pro Pro Pro Pro Pro Ala Thr Gly Arg Ser Gly Pro Pro Pro Pro
385                 390                 395                 400

Pro Leu Pro Gly Ala Gly Gly Pro Pro Ala Pro Pro Pro Pro Pro
                405                 410                 415

Pro Pro Pro Pro Pro Cys Pro Gly Ser Gly Pro Ala Pro Pro Pro
                420                 425                 430

Leu Pro Pro Thr Pro Val Ser Gly Gly Ser Pro Ala Pro Gly Gly Gly
        435                 440                 445

Arg Gly Ala Leu Leu Asp Gln Ile Arg Gln Gly Ile Gln Leu Asn Lys
        450                 455                 460

Thr Pro Gly Ala Leu Glu Asn Ser Val Gln Gln Pro Pro Ala Gln Gln
465                 470                 475                 480

Ser Glu Gly Leu Val Gly Ala Leu Met His Val Met Gln Lys Arg Ser
                485                 490                 495

Arg Val Ile His Ser Ser Asp Glu Gly Asp Gln Thr Gly Glu Asp
                500                 505                 510

Glu Glu Asp Asp Glu Trp Asp Asp
            515                 520

<210> SEQ ID NO 37
<211> LENGTH: 303
<212> TYPE: DNA
<213> ORGANISM: Artificial sequence
<220> FEATURE:
<223> OTHER INFORMATION: Description of the artificial sequence:
      Fragment of the murine WASP protein
<220> FEATURE:
<221> NAME/KEY: CDS
<222> LOCATION: (1)..(303)
```

```
<400> SEQUENCE: 37 cct cca ccc tgc cct ggg agt gga ccc gcc cct ccc ccg ctc cct cct    48
Pro Pro Pro Cys Pro Gly Ser Gly Pro Ala Pro Pro Leu Pro Pro
 1               5                  10                  15 act cca gtg tct ggg ggg agc cca gca cct ggt ggg ggc cgg ggt gca    96
Thr Pro Val Ser Gly Gly Ser Pro Ala Pro Gly Gly Gly Arg Gly Ala
                20                  25                  30 ctt ttg gac caa atc cgg cag gga att cag ctg aac aag acc cct gga   144
Leu Leu Asp Gln Ile Arg Gln Gly Ile Gln Leu Asn Lys Thr Pro Gly
         35                  40                  45 gct cta gag aac tca gta cag caa cca ccc gcg cag cag tca gaa ggc   192
Ala Leu Glu Asn Ser Val Gln Gln Pro Pro Ala Gln Gln Ser Glu Gly
     50                  55                  60 cta gta ggt gcc ctg atg cat gtc atg cag aag agg agt aga gtc atc   240
Leu Val Gly Ala Leu Met His Val Met Gln Lys Arg Ser Arg Val Ile
 65                  70                  75                  80 cat tcc tca gat gaa ggg gag gat cag acc ggc gag gat gaa gag gat   288
His Ser Ser Asp Glu Gly Glu Asp Gln Thr Gly Glu Asp Glu Glu Asp
                 85                  90                  95 gat gaa tgg gat gac                                               303
Asp Glu Trp Asp Asp
            100

<210> SEQ ID NO 38
<211> LENGTH: 101
<212> TYPE: PRT
<213> ORGANISM: Artificial sequence
<220> FEATURE:
<223> OTHER INFORMATION: Description of the artificial sequence:
      Fragment of the murine WASP protein

<400> SEQUENCE: 38

Pro Pro Pro Cys Pro Gly Ser Gly Pro Ala Pro Pro Leu Pro Pro
 1               5                  10                  15

Thr Pro Val Ser Gly Gly Ser Pro Ala Pro Gly Gly Gly Arg Gly Ala
                20                  25                  30

Leu Leu Asp Gln Ile Arg Gln Gly Ile Gln Leu Asn Lys Thr Pro Gly
         35                  40                  45

Ala Leu Glu Asn Ser Val Gln Gln Pro Pro Ala Gln Gln Ser Glu Gly
     50                  55                  60

Leu Val Gly Ala Leu Met His Val Met Gln Lys Arg Ser Arg Val Ile
 65                  70                  75                  80

His Ser Ser Asp Glu Gly Glu Asp Gln Thr Gly Glu Asp Glu Glu Asp
                 85                  90                  95

Asp Glu Trp Asp Asp
            100

<210> SEQ ID NO 39
<211> LENGTH: 258
<212> TYPE: DNA
<213> ORGANISM: Artificial sequence
<220> FEATURE:
<223> OTHER INFORMATION: Description of the artificial sequence:
      Fragment of the murine WASP protein
<220> FEATURE:
<221> NAME/KEY: CDS
<222> LOCATION: (1)..(258)

<400> SEQUENCE: 39 cct cca ccc tgc cct ggg agt gga ccc gcc cct ccc ccg ctc cct cct    48
Pro Pro Pro Cys Pro Gly Ser Gly Pro Ala Pro Pro Leu Pro Pro
 1               5                  10                  15
```

```
act cca gtg tct ggg ggg agc cca gca cct ggt ggg ggc cgg ggt gca      96
Thr Pro Val Ser Gly Gly Ser Pro Ala Pro Gly Gly Gly Arg Gly Ala
            20                  25                  30 ctt ttg gac caa atc cgg cag gga att cag ctg aac aag acc cct gga     144
Leu Leu Asp Gln Ile Arg Gln Gly Ile Gln Leu Asn Lys Thr Pro Gly
         35                  40                  45 gct cta gag aac tca gta cag caa cca ccc gcg cag cag tca gaa ggc     192
Ala Leu Glu Asn Ser Val Gln Gln Pro Pro Ala Gln Gln Ser Glu Gly
 50                  55                  60 cta gta ggt gcc ctg atg cat gtc atg cag aag agg agt aga gtc atc     240
Leu Val Gly Ala Leu Met His Val Met Gln Lys Arg Ser Arg Val Ile
 65                  70                  75                  80 cat tcc tca gat gaa ggg                                             258
His Ser Ser Asp Glu Gly
                85

<210> SEQ ID NO 40
<211> LENGTH: 86
<212> TYPE: PRT
<213> ORGANISM: Artificial sequence
<220> FEATURE:
<223> OTHER INFORMATION: Description of the artificial sequence:
      Fragment of the murine WASP protein

<400> SEQUENCE: 40

Pro Pro Pro Cys Pro Gly Ser Gly Pro Ala Pro Pro Leu Pro Pro
  1               5                  10                  15

Thr Pro Val Ser Gly Gly Ser Pro Ala Pro Gly Gly Gly Arg Gly Ala
            20                  25                  30

Leu Leu Asp Gln Ile Arg Gln Gly Ile Gln Leu Asn Lys Thr Pro Gly
         35                  40                  45

Ala Leu Glu Asn Ser Val Gln Gln Pro Pro Ala Gln Gln Ser Glu Gly
     50                  55                  60

Leu Val Gly Ala Leu Met His Val Met Gln Lys Arg Ser Arg Val Ile
 65                  70                  75                  80

His Ser Ser Asp Glu Gly
                85

<210> SEQ ID NO 41
<211> LENGTH: 219
<212> TYPE: DNA
<213> ORGANISM: Artificial sequence
<220> FEATURE:
<223> OTHER INFORMATION: Description of the artificial sequence:
      Fragment of the murine WASP protein
<220> FEATURE:
<221> NAME/KEY: CDS
<222> LOCATION: (1)..(219)

<400> SEQUENCE: 41 ggc cgg ggt gca ctt ttg gac caa atc cgg cag gga att cag ctg aac      48
Gly Arg Gly Ala Leu Leu Asp Gln Ile Arg Gln Gly Ile Gln Leu Asn
  1               5                  10                  15 aag acc cct gga gct cta gag aac tca gta cag caa cca ccc gcg cag     96
Lys Thr Pro Gly Ala Leu Glu Asn Ser Val Gln Gln Pro Pro Ala Gln
             20                  25                  30 cag tca gaa ggc cta gta ggt gcc ctg atg cat gtc atg cag aag agg     144
Gln Ser Glu Gly Leu Val Gly Ala Leu Met His Val Met Gln Lys Arg
         35                  40                  45 agt aga gtc atc cat tcc tca gat gaa ggg gag gat cag acc ggc gag     192
Ser Arg Val Ile His Ser Ser Asp Glu Gly Glu Asp Gln Thr Gly Glu
     50                  55                  60
```

```
gat gaa gag gat gat gaa tgg gat gac                                    219
Asp Glu Glu Asp Asp Glu Trp Asp Asp
 65                  70
```

<210> SEQ ID NO 42
<211> LENGTH: 73
<212> TYPE: PRT
<213> ORGANISM: Artificial sequence
<220> FEATURE:
<223> OTHER INFORMATION: Description of the artificial sequence:
      Fragment of the murine WASP protein

<400> SEQUENCE: 42

```
Gly Arg Gly Ala Leu Leu Asp Gln Ile Arg Gln Gly Ile Gln Leu Asn
  1               5                  10                  15

Lys Thr Pro Gly Ala Leu Glu Asn Ser Val Gln Gln Pro Pro Ala Gln
             20                  25                  30

Gln Ser Glu Gly Leu Val Gly Ala Leu Met His Val Met Gln Lys Arg
         35                  40                  45

Ser Arg Val Ile His Ser Ser Asp Glu Gly Glu Asp Gln Thr Gly Glu
     50                  55                  60

Asp Glu Glu Asp Asp Glu Trp Asp Asp
 65                  70
```

<210> SEQ ID NO 43
<211> LENGTH: 174
<212> TYPE: DNA
<213> ORGANISM: Artificial sequence
<220> FEATURE:
<223> OTHER INFORMATION: Description of the artificial sequence:
      Fragment of the murine WASP protein
<220> FEATURE:
<221> NAME/KEY: CDS
<222> LOCATION: (1)..(174)

<400> SEQUENCE: 43

```
ggc cgg ggt gca ctt ttg gac caa atc cgg cag gga att cag ctg aac        48
Gly Arg Gly Ala Leu Leu Asp Gln Ile Arg Gln Gly Ile Gln Leu Asn
  1               5                  10                  15 aag acc cct gga gct cta gag aac tca gta cag caa cca ccc gcg cag        96
Lys Thr Pro Gly Ala Leu Glu Asn Ser Val Gln Gln Pro Pro Ala Gln
             20                  25                  30 cag tca gaa ggc cta gta ggt gcc ctg atg cat gtc atg cag aag agg       144
Gln Ser Glu Gly Leu Val Gly Ala Leu Met His Val Met Gln Lys Arg
         35                  40                  45 agt aga gtc atc cat tcc tca gat gaa ggg                               174
Ser Arg Val Ile His Ser Ser Asp Glu Gly
     50                  55
```

<210> SEQ ID NO 44
<211> LENGTH: 58
<212> TYPE: PRT
<213> ORGANISM: Artificial sequence
<220> FEATURE:
<223> OTHER INFORMATION: Description of the artificial sequence:
      Fragment of the murine WASP protein

<400> SEQUENCE: 44

```
Gly Arg Gly Ala Leu Leu Asp Gln Ile Arg Gln Gly Ile Gln Leu Asn
  1               5                  10                  15

Lys Thr Pro Gly Ala Leu Glu Asn Ser Val Gln Gln Pro Pro Ala Gln
             20                  25                  30

Gln Ser Glu Gly Leu Val Gly Ala Leu Met His Val Met Gln Lys Arg
```

```
                    35                  40                  45
Ser Arg Val Ile His Ser Ser Asp Glu Gly
    50                  55

<210> SEQ ID NO 45
<211> LENGTH: 1588
<212> TYPE: DNA
<213> ORGANISM: Rattus rattus
<220> FEATURE:
<221> NAME/KEY: CDS
<222> LOCATION: (72)..(1574)

<400> SEQUENCE: 45
cggagtggga ccgagtgctc gcccaccacc agaagagacg gccctggaca ctccacccca        60
ccggcgacac c atg agc tcg ggc cag cag ccc ccg cgg agg gtc acc aac       110
            Met Ser Ser Gly Gln Gln Pro Pro Arg Arg Val Thr Asn
              1               5                  10 gtg ggc tcc ctg ctg ctc acc ccg caa gaa aac gag tct ctt ttc tcc       158
Val Gly Ser Leu Leu Leu Thr Pro Gln Glu Asn Glu Ser Leu Phe Ser
         15                  20                  25 ttc ctc ggc aag aaa tgt gtg act atg tct tca gca gtg gtg cag tta       206
Phe Leu Gly Lys Lys Cys Val Thr Met Ser Ser Ala Val Val Gln Leu
 30                  35                  40                  45 tat gca gct gat cgg aac tgt atg tgg tca aag aag tgc agt ggt gtt       254
Tyr Ala Ala Asp Arg Asn Cys Met Trp Ser Lys Lys Cys Ser Gly Val
                 50                  55                  60 gct tgt ctt gtt aag gac aat cct cag aga tct tat ttt tta aga ata       302
Ala Cys Leu Val Lys Asp Asn Pro Gln Arg Ser Tyr Phe Leu Arg Ile
             65                  70                  75 ttt gac att aag gat ggg aaa tta ctg tgg gaa caa gag cta tac aat       350
Phe Asp Ile Lys Asp Gly Lys Leu Leu Trp Glu Gln Glu Leu Tyr Asn
         80                  85                  90 aac ttt gta tat aat agt cct aga gga tat ttt cat acc ttt gct gga       398
Asn Phe Val Tyr Asn Ser Pro Arg Gly Tyr Phe His Thr Phe Ala Gly
     95                 100                 105 gat act tgt caa gta gct ctt aat ttt gcc aat gaa gaa gaa gca aaa       446
Asp Thr Cys Gln Val Ala Leu Asn Phe Ala Asn Glu Glu Glu Ala Lys
110                 115                 120                 125 aag ttc cga aaa gca gtt aca gac ctg ttg ggt cga cga caa agg aaa       494
Lys Phe Arg Lys Ala Val Thr Asp Leu Leu Gly Arg Arg Gln Arg Lys
                130                 135                 140 tct gaa aaa aga cga gat gct cca aat ggt ccc aat cta ccc atg gct       542
Ser Glu Lys Arg Arg Asp Ala Pro Asn Gly Pro Asn Leu Pro Met Ala
            145                 150                 155 aca gtt gac ata aaa aat cca gaa atc aca aca aac agg ttt tat agt       590
Thr Val Asp Ile Lys Asn Pro Glu Ile Thr Thr Asn Arg Phe Tyr Ser
        160                 165                 170 tca caa gtc aac aac atc tcc cac acc aaa gaa aag aag aaa gga aaa       638
Ser Gln Val Asn Asn Ile Ser His Thr Lys Glu Lys Lys Lys Gly Lys
    175                 180                 185 gct aaa aag aag aga tta acc aag gca gat att gga aca cca agt aat       686
Ala Lys Lys Lys Arg Leu Thr Lys Ala Asp Ile Gly Thr Pro Ser Asn
190                 195                 200                 205 ttc cag cac att gga cat gtt ggt tgg gat cca aat aca ggt ttt gat       734
Phe Gln His Ile Gly His Val Gly Trp Asp Pro Asn Thr Gly Phe Asp
                210                 215                 220 cta aat aat ttg gat cca gaa ttg aag aat ctt ttt gat atg tgt ggg       782
Leu Asn Asn Leu Asp Pro Glu Leu Lys Asn Leu Phe Asp Met Cys Gly
            225                 230                 235 atc tct gag gcc cag ctt aaa gac aga gaa aca tca aaa gtt att tat       830
```

```
Ile Ser Glu Ala Gln Leu Lys Asp Arg Glu Thr Ser Lys Val Ile Tyr
        240                 245                 250 gac ttt att gaa aaa aca gga ggt gta gaa gct gtt aaa aat gaa ctc       878
Asp Phe Ile Glu Lys Thr Gly Gly Val Glu Ala Val Lys Asn Glu Leu
        255                 260                 265 cga agg caa gca cca cca cct cct cca ccc tca aga gga gga cct ccc       926
Arg Arg Gln Ala Pro Pro Pro Pro Pro Pro Ser Arg Gly Gly Pro Pro
270                 275                 280                 285 cct cct cct ccc cct cct cac agc tca ggc cct cct ccc cct cct gcc       974
Pro Pro Pro Pro Pro Pro His Ser Ser Gly Pro Pro Pro Pro Pro Ala
                290                 295                 300 cgt gga agg ggg gct cct ccc ccg cca cca tca aga gct cct act gct      1022
Arg Gly Arg Gly Ala Pro Pro Pro Pro Pro Ser Arg Ala Pro Thr Ala
                    305                 310                 315 gca cct cca cct cca cct cct tct agg cct ggt gtt gtc gtt cct cca      1070
Ala Pro Pro Pro Pro Pro Pro Ser Arg Pro Gly Val Val Val Pro Pro
            320                 325                 330 cct cct cca aac agg atg tac cct cct cca cca gcc ctg cct tcc          1118
Pro Pro Pro Asn Arg Met Tyr Pro Pro Pro Pro Ala Leu Pro Ser
        335                 340                 345 tca gca cct tca ggc cca cca cca cct ccg cct ctg tct atg gca ggg      1166
Ser Ala Pro Ser Gly Pro Pro Pro Pro Pro Pro Leu Ser Met Ala Gly
350                 355                 360                 365 tcc aca gca cca cca cct cct cca cca cct ccc cct cca cca ggg cca      1214
Ser Thr Ala Pro Pro Pro Pro Pro Pro Pro Pro Pro Pro Pro Gly Pro
                370                 375                 380 cca cct ccc cct ggc ctg cct tct gat ggt gac cat caa gtt cca gct      1262
Pro Pro Pro Pro Gly Leu Pro Ser Asp Gly Asp His Gln Val Pro Ala
                    385                 390                 395 tct tca gga aac aaa gca gct ctt ttg gat caa att aga gag ggt gct      1310
Ser Ser Gly Asn Lys Ala Ala Leu Leu Asp Gln Ile Arg Glu Gly Ala
            400                 405                 410 cag cta aaa aaa gtg gag cag aat agt cgg ccc gtg tcc tgc tca gga      1358
Gln Leu Lys Lys Val Glu Gln Asn Ser Arg Pro Val Ser Cys Ser Gly
        415                 420                 425 agg gat gca ctt cta gac cag ata cga cag ggc att cag ttg aaa tcc      1406
Arg Asp Ala Leu Leu Asp Gln Ile Arg Gln Gly Ile Gln Leu Lys Ser
430                 435                 440                 445 gtg tct gat ggc caa gag tcc aca cca cca acc ccc gcg ccc act tca      1454
Val Ser Asp Gly Gln Glu Ser Thr Pro Pro Thr Pro Ala Pro Thr Ser
                450                 455                 460 gga att gtg ggt gcg ctg atg gaa gtg atg cag aaa agg agc aaa gcc      1502
Gly Ile Val Gly Ala Leu Met Glu Val Met Gln Lys Arg Ser Lys Ala
                    465                 470                 475 att cat tcc tca gat gaa gat gaa gat gat gat gat gaa gaa gat ttt      1550
Ile His Ser Ser Asp Glu Asp Glu Asp Asp Asp Asp Glu Glu Asp Phe
            480                 485                 490 cag gat gat gat gag tgg gaa gac tgatctatat tatt                      1588
Gln Asp Asp Asp Glu Trp Glu Asp
        495                 500

<210> SEQ ID NO 46
<211> LENGTH: 501
<212> TYPE: PRT
<213> ORGANISM: Rattus rattus

<400> SEQUENCE: 46

Met Ser Ser Gly Gln Gln Pro Pro Arg Arg Val Thr Asn Val Gly Ser
1               5                   10                  15

Leu Leu Leu Thr Pro Gln Glu Asn Glu Ser Leu Phe Ser Phe Leu Gly
```

```
                 20                  25                  30
Lys Lys Cys Val Thr Met Ser Ser Ala Val Val Gln Leu Tyr Ala Ala
             35                  40                  45
Asp Arg Asn Cys Met Trp Ser Lys Lys Cys Ser Gly Val Ala Cys Leu
         50                  55                  60
Val Lys Asp Asn Pro Gln Arg Ser Tyr Phe Leu Arg Ile Phe Asp Ile
 65                  70                  75                  80
Lys Asp Gly Lys Leu Leu Trp Glu Gln Glu Leu Tyr Asn Asn Phe Val
                 85                  90                  95
Tyr Asn Ser Pro Arg Gly Tyr Phe His Thr Phe Ala Gly Asp Thr Cys
            100                 105                 110
Gln Val Ala Leu Asn Phe Ala Asn Glu Glu Ala Lys Lys Phe Arg
            115                 120                 125
Lys Ala Val Thr Asp Leu Leu Gly Arg Arg Gln Arg Lys Ser Glu Lys
        130                 135                 140
Arg Arg Asp Ala Pro Asn Gly Pro Asn Leu Pro Met Ala Thr Val Asp
145                 150                 155                 160
Ile Lys Asn Pro Glu Ile Thr Thr Asn Arg Phe Tyr Ser Ser Gln Val
                165                 170                 175
Asn Asn Ile Ser His Thr Lys Glu Lys Lys Gly Lys Ala Lys Lys
            180                 185                 190
Lys Arg Leu Thr Lys Ala Asp Ile Gly Thr Pro Ser Asn Phe Gln His
        195                 200                 205
Ile Gly His Val Gly Trp Asp Pro Asn Thr Gly Phe Asp Leu Asn Asn
    210                 215                 220
Leu Asp Pro Glu Leu Lys Asn Leu Phe Asp Met Cys Gly Ile Ser Glu
225                 230                 235                 240
Ala Gln Leu Lys Asp Arg Glu Thr Ser Lys Val Ile Tyr Asp Phe Ile
                245                 250                 255
Glu Lys Thr Gly Gly Val Glu Ala Val Lys Asn Glu Leu Arg Arg Gln
            260                 265                 270
Ala Pro Pro Pro Pro Pro Ser Arg Gly Gly Pro Pro Pro Pro
        275                 280                 285
Pro Pro Pro His Ser Ser Gly Pro Pro Pro Pro Ala Arg Gly Arg
    290                 295                 300
Gly Ala Pro Pro Pro Pro Ser Arg Ala Pro Thr Ala Ala Pro Pro
305                 310                 315                 320
Pro Pro Pro Pro Ser Arg Pro Gly Val Val Pro Pro Pro Pro
                325                 330                 335
Asn Arg Met Tyr Pro Pro Pro Pro Ala Leu Pro Ser Ser Ala Pro
            340                 345                 350
Ser Gly Pro Pro Pro Pro Pro Leu Ser Met Ala Gly Ser Thr Ala
        355                 360                 365
Pro Pro Pro Pro Pro Pro Pro Pro Pro Pro Gly Pro Pro Pro
    370                 375                 380
Pro Gly Leu Pro Ser Asp Gly Asp His Gln Val Pro Ala Ser Ser Gly
385                 390                 395                 400
Asn Lys Ala Ala Leu Leu Asp Gln Ile Arg Glu Gly Ala Gln Leu Lys
            405                 410                 415
Lys Val Glu Gln Asn Ser Arg Pro Val Ser Cys Ser Gly Arg Asp Ala
        420                 425                 430
Leu Leu Asp Gln Ile Arg Gln Gly Ile Gln Leu Lys Ser Val Ser Asp
    435                 440                 445
```

```
Gly Gln Glu Ser Thr Pro Pro Thr Pro Ala Pro Thr Ser Gly Ile Val
    450                 455                 460

Gly Ala Leu Met Glu Val Met Gln Lys Arg Ser Lys Ala Ile His Ser
465                 470                 475                 480

Ser Asp Glu Asp Glu Asp Asp Asp Asp Glu Asp Phe Gln Asp Asp
                485                 490                 495

Asp Glu Trp Glu Asp
        500

<210> SEQ ID NO 47
<211> LENGTH: 303
<212> TYPE: DNA
<213> ORGANISM: Artificial sequence
<220> FEATURE:
<223> OTHER INFORMATION: Description of the artificial sequence:
      Fragment of the rat N-WASP protein
<220> FEATURE:
<221> NAME/KEY: CDS
<222> LOCATION: (1)..(303)

<400> SEQUENCE: 47 aac aaa gca gct ctt ttg gat caa att aga gag ggt gct cag cta aaa      48
Asn Lys Ala Ala Leu Leu Asp Gln Ile Arg Glu Gly Ala Gln Leu Lys
  1               5                  10                  15 aaa gtg gag cag aat agt cgg ccc gtg tcc tgc tca gga agg gat gca      96
Lys Val Glu Gln Asn Ser Arg Pro Val Ser Cys Ser Gly Arg Asp Ala
             20                  25                  30 ctt cta gac cag ata cga cag ggc att cag ttg aaa tcc gtg tct gat     144
Leu Leu Asp Gln Ile Arg Gln Gly Ile Gln Leu Lys Ser Val Ser Asp
         35                  40                  45 ggc caa gag tcc aca cca cca acc ccc gcg ccc act tca gga att gtg     192
Gly Gln Glu Ser Thr Pro Pro Thr Pro Ala Pro Thr Ser Gly Ile Val
     50                  55                  60 ggt gcg ctg atg gaa gtg atg cag aaa agg agc aaa gcc att cat tcc     240
Gly Ala Leu Met Glu Val Met Gln Lys Arg Ser Lys Ala Ile His Ser
 65                  70                  75                  80 tca gat gaa gat gaa gat gat gat gat gaa gaa gat ttt cag gat gat     288
Ser Asp Glu Asp Glu Asp Asp Asp Asp Glu Glu Asp Phe Gln Asp Asp
                 85                  90                  95 gat gag tgg gaa gac                                                  303
Asp Glu Trp Glu Asp
            100

<210> SEQ ID NO 48
<211> LENGTH: 101
<212> TYPE: PRT
<213> ORGANISM: Artificial sequence
<220> FEATURE:
<223> OTHER INFORMATION: Description of the artificial sequence:
      Fragment of the rat N-WASP protein

<400> SEQUENCE: 48

Asn Lys Ala Ala Leu Leu Asp Gln Ile Arg Glu Gly Ala Gln Leu Lys
  1               5                  10                  15

Lys Val Glu Gln Asn Ser Arg Pro Val Ser Cys Ser Gly Arg Asp Ala
             20                  25                  30

Leu Leu Asp Gln Ile Arg Gln Gly Ile Gln Leu Lys Ser Val Ser Asp
         35                  40                  45

Gly Gln Glu Ser Thr Pro Pro Thr Pro Ala Pro Thr Ser Gly Ile Val
     50                  55                  60

Gly Ala Leu Met Glu Val Met Gln Lys Arg Ser Lys Ala Ile His Ser
```

```
                        65                  70                  75                  80
                Ser Asp Glu Asp Glu Asp Asp Asp Glu Asp Phe Gln Asp Asp
                                85                  90                  95

Asp Glu Trp Glu Asp
                            100

<210> SEQ ID NO 49
<211> LENGTH: 252
<212> TYPE: DNA
<213> ORGANISM: Artificial sequence
<220> FEATURE:
<223> OTHER INFORMATION: Description of the artificial sequence:
      Fragment of the rat N-WASP protein
<220> FEATURE:
<221> NAME/KEY: CDS
<222> LOCATION: (1)..(252)

<400> SEQUENCE: 49 aac aaa gca gct ctt ttg gat caa att aga gag ggt gct cag cta aaa      48
Asn Lys Ala Ala Leu Leu Asp Gln Ile Arg Glu Gly Ala Gln Leu Lys
 1               5                  10                  15 aaa gtg gag cag aat agt cgg ccc gtg tcc tgc tca gga agg gat gca      96
Lys Val Glu Gln Asn Ser Arg Pro Val Ser Cys Ser Gly Arg Asp Ala
            20                  25                  30 ctt cta gac cag ata cga cag ggc att cag ttg aaa tcc gtg tct gat     144
Leu Leu Asp Gln Ile Arg Gln Gly Ile Gln Leu Lys Ser Val Ser Asp
        35                  40                  45 ggc caa gag tcc aca cca cca acc ccc gcg ccc act tca gga att gtg     192
Gly Gln Glu Ser Thr Pro Pro Thr Pro Ala Pro Thr Ser Gly Ile Val
    50                  55                  60 ggt gcg ctg atg gaa gtg atg cag aaa agg agc aaa gcc att cat tcc     240
Gly Ala Leu Met Glu Val Met Gln Lys Arg Ser Lys Ala Ile His Ser
65                  70                  75                  80 tca gat gaa gat                                                     252
Ser Asp Glu Asp <210> SEQ ID NO 50
<211> LENGTH: 84
<212> TYPE: PRT
<213> ORGANISM: Artificial sequence
<220> FEATURE:
<223> OTHER INFORMATION: Description of the artificial sequence:
      Fragment of the rat N-WASP protein

<400> SEQUENCE: 50

Asn Lys Ala Ala Leu Leu Asp Gln Ile Arg Glu Gly Ala Gln Leu Lys
 1               5                  10                  15

Lys Val Glu Gln Asn Ser Arg Pro Val Ser Cys Ser Gly Arg Asp Ala
            20                  25                  30

Leu Leu Asp Gln Ile Arg Gln Gly Ile Gln Leu Lys Ser Val Ser Asp
        35                  40                  45

Gly Gln Glu Ser Thr Pro Pro Thr Pro Ala Pro Thr Ser Gly Ile Val
    50                  55                  60

Gly Ala Leu Met Glu Val Met Gln Lys Arg Ser Lys Ala Ile His Ser
65                  70                  75                  80
Ser Asp Glu Asp

<210> SEQ ID NO 51
<211> LENGTH: 219
<212> TYPE: DNA
<213> ORGANISM: Artificial sequence
<220> FEATURE:
<223> OTHER INFORMATION: Description of the artificial sequence:
```

```
        Fragment of the rat N-WASP protein
<220> FEATURE:
<221> NAME/KEY: CDS
<222> LOCATION: (1)..(219)

<400> SEQUENCE: 51 gga agg gat gca ctt cta gac cag ata cga cag ggc att cag ttg aaa        48
Gly Arg Asp Ala Leu Leu Asp Gln Ile Arg Gln Gly Ile Gln Leu Lys
  1               5                  10                  15 tcc gtg tct gat ggc caa gag tcc aca cca cca acc ccc gcg ccc act        96
Ser Val Ser Asp Gly Gln Glu Ser Thr Pro Pro Thr Pro Ala Pro Thr
             20                  25                  30 tca gga att gtg ggt gcg ctg atg gaa gtg atg cag aaa agg agc aaa       144
Ser Gly Ile Val Gly Ala Leu Met Glu Val Met Gln Lys Arg Ser Lys
         35                  40                  45 gcc att cat tcc tca gat gaa gat gaa gat gat gat gaa gaa gat           192
Ala Ile His Ser Ser Asp Glu Asp Glu Asp Asp Asp Glu Glu Asp
     50                  55                  60 ttt cag gat gat gat gag tgg gaa gac                                   219
Phe Gln Asp Asp Asp Glu Trp Glu Asp
 65                  70

<210> SEQ ID NO 52
<211> LENGTH: 73
<212> TYPE: PRT
<213> ORGANISM: Artificial sequence
<220> FEATURE:
<223> OTHER INFORMATION: Description of the artificial sequence:
      Fragment of the rat N-WASP protein

<400> SEQUENCE: 52

Gly Arg Asp Ala Leu Leu Asp Gln Ile Arg Gln Gly Ile Gln Leu Lys
  1               5                  10                  15

Ser Val Ser Asp Gly Gln Glu Ser Thr Pro Pro Thr Pro Ala Pro Thr
             20                  25                  30

Ser Gly Ile Val Gly Ala Leu Met Glu Val Met Gln Lys Arg Ser Lys
         35                  40                  45

Ala Ile His Ser Ser Asp Glu Asp Glu Asp Asp Asp Glu Glu Asp
     50                  55                  60

Phe Gln Asp Asp Asp Glu Trp Glu Asp
 65                  70

<210> SEQ ID NO 53
<211> LENGTH: 168
<212> TYPE: DNA
<213> ORGANISM: Artificial sequence
<220> FEATURE:
<223> OTHER INFORMATION: Description of the artificial sequence:
      Fragment of the rat N-WASP protein
<220> FEATURE:
<221> NAME/KEY: CDS
<222> LOCATION: (1)..(168)

<400> SEQUENCE: 53 gga agg gat gca ctt cta gac cag ata cga cag ggc att cag ttg aaa        48
Gly Arg Asp Ala Leu Leu Asp Gln Ile Arg Gln Gly Ile Gln Leu Lys
  1               5                  10                  15 tcc gtg tct gat ggc caa gag tcc aca cca cca acc ccc gcg ccc act        96
Ser Val Ser Asp Gly Gln Glu Ser Thr Pro Pro Thr Pro Ala Pro Thr
             20                  25                  30 tca gga att gtg ggt gcg ctg atg gaa gtg atg cag aaa agg agc aaa       144
Ser Gly Ile Val Gly Ala Leu Met Glu Val Met Gln Lys Arg Ser Lys
         35                  40                  45
```

```
gcc att cat tcc tca gat gaa gat                                    168
Ala Ile His Ser Ser Asp Glu Asp
    50                  55
```

<210> SEQ ID NO 54
<211> LENGTH: 56
<212> TYPE: PRT
<213> ORGANISM: Artificial sequence
<220> FEATURE:
<223> OTHER INFORMATION: Description of the artificial sequence:
      Fragment of the rat N-WASP protein

<400> SEQUENCE: 54

```
Gly Arg Asp Ala Leu Leu Asp Gln Ile Arg Gln Gly Ile Gln Leu Lys
 1               5                  10                  15

Ser Val Ser Asp Gly Gln Glu Ser Thr Pro Pro Thr Pro Ala Pro Thr
            20                  25                  30

Ser Gly Ile Val Gly Ala Leu Met Glu Val Met Gln Lys Arg Ser Lys
        35                  40                  45

Ala Ile His Ser Ser Asp Glu Asp
    50                  55
```

<210> SEQ ID NO 55
<211> LENGTH: 1836
<212> TYPE: DNA
<213> ORGANISM: Bos taurus
<220> FEATURE:
<221> NAME/KEY: CDS
<222> LOCATION: (288)..(1802)

<400> SEQUENCE: 55

```
gccgccgaag aaggttgggg gaggagttgg gagtttagcg cagtcgccgg agtgcgagga    60
caacgaccat ccggccagag cctaccccgg cgggaacggg gagcttccct ttctcacagc   120
ggcccgccgt cggctcctcc ttccgtggtc tcctccctgc gccggaggag ctgcgagatg   180
ctacgcctct gattcccctc ctcccgcccc tgtcacccag aaggggaacg agcgctcgcc   240
cactcgccgg agagacggcc ctggctccct accccgccgg cgaaacc atg agc tcc    296
                                                    Met Ser Ser
                                                      1 ggc cag cag cag ccg ccg ccg cgg agg gtc acc aac gtg ggg tcc        344
Gly Gln Gln Gln Pro Pro Pro Arg Arg Val Thr Asn Val Gly Ser
  5                  10                  15 ctg ctc ctc acc ccg cag gag aac gag tcc ctc ttc acc ttc ctc ggc    392
Leu Leu Leu Thr Pro Gln Glu Asn Glu Ser Leu Phe Thr Phe Leu Gly
 20                  25                  30                  35 aag aaa tgt gtg acc atg tct tcg gca gtg gta cag tta tat gca gca    440
Lys Lys Cys Val Thr Met Ser Ser Ala Val Val Gln Leu Tyr Ala Ala
                40                  45                  50 gat cgg aac tgt atg tgg tca aag aag tgc agt ggt gtt gct tgt ctt    488
Asp Arg Asn Cys Met Trp Ser Lys Lys Cys Ser Gly Val Ala Cys Leu
            55                  60                  65 gtt aag gac aat cca cag aga tct tat ttt tta aga ata ttt gat atc    536
Val Lys Asp Asn Pro Gln Arg Ser Tyr Phe Leu Arg Ile Phe Asp Ile
        70                  75                  80 aag gat ggg aaa cta ttg tgg gaa caa gag cta tac aat aac ttt gta    584
Lys Asp Gly Lys Leu Leu Trp Glu Gln Glu Leu Tyr Asn Asn Phe Val
    85                  90                  95 tat aat agt cct aga gga tat ttt cat acc ttt gct gga gat acc tgt    632
Tyr Asn Ser Pro Arg Gly Tyr Phe His Thr Phe Ala Gly Asp Thr Cys
100                 105                 110                 115 caa gtt gct ctt aat ttt gcc aat gaa gaa gaa gca aaa aaa ttc cga    680
```

-continued

| | | | | | | | | | | | | |
|---|---|---|---|---|---|---|---|---|---|---|---|---|
| Gln | Val | Ala | Leu | Asn | Phe | Ala | Asn | Glu | Glu | Ala | Lys | Lys | Phe | Arg |
| | | | 120 | | | | 125 | | | | 130 | | | |

```
aaa gca gtt aca gac ttg ttg gga cga cga caa agg aaa tct gag aaa     728
Lys Ala Val Thr Asp Leu Leu Gly Arg Arg Gln Arg Lys Ser Glu Lys
            135                 140                 145 aga cga gac ccc cca aat ggt cct aat cta ccc atg gca aca gtt gac     776
Arg Arg Asp Pro Pro Asn Gly Pro Asn Leu Pro Met Ala Thr Val Asp
            150                 155                 160 ata aaa aat cca gaa att aca aca aat aga ttt tat ggt ccg caa atc     824
Ile Lys Asn Pro Glu Ile Thr Thr Asn Arg Phe Tyr Gly Pro Gln Ile
    165                 170                 175 aac aac atc tcc cat acc aaa gaa aag aaa aaa gga aaa gct aaa aag     872
Asn Asn Ile Ser His Thr Lys Glu Lys Lys Lys Gly Lys Ala Lys Lys
180                 185                 190                 195 aag agg tta act aag gca gat att gga aca cca agc aat ttc caa cac     920
Lys Arg Leu Thr Lys Ala Asp Ile Gly Thr Pro Ser Asn Phe Gln His
                200                 205                 210 att gga cat gtg ggt tgg gat ccg aat act ggc ttt gat ctg aat aat     968
Ile Gly His Val Gly Trp Asp Pro Asn Thr Gly Phe Asp Leu Asn Asn
            215                 220                 225 ttg gat cca gaa ttg aag aat ctt ttt gat atg tgt gga atc tca gag    1016
Leu Asp Pro Glu Leu Lys Asn Leu Phe Asp Met Cys Gly Ile Ser Glu
            230                 235                 240 gca caa ctt aaa gac aga gaa aca tca aaa gtt ata tat gac ttc att    1064
Ala Gln Leu Lys Asp Arg Glu Thr Ser Lys Val Ile Tyr Asp Phe Ile
    245                 250                 255 gaa aaa aca gga ggt gtt gaa gct gtt aaa aat gaa ctg cga agg caa    1112
Glu Lys Thr Gly Gly Val Glu Ala Val Lys Asn Glu Leu Arg Arg Gln
260                 265                 270                 275 gca cca cca cct cca cca cca tca agg gga ggg ccg ccc cct cct ccc    1160
Ala Pro Pro Pro Pro Pro Pro Ser Arg Gly Gly Pro Pro Pro Pro Pro
                280                 285                 290 ccg cct cca cat agc tcg ggc cct cct ccc cct cct gcc agg gga aga    1208
Pro Pro Pro His Ser Ser Gly Pro Pro Pro Pro Pro Ala Arg Gly Arg
            295                 300                 305 ggg gct cct cct cca cca cct tca aga gct ccc aca gct gca ccg cca    1256
Gly Ala Pro Pro Pro Pro Pro Ser Arg Ala Pro Thr Ala Ala Pro Pro
            310                 315                 320 cca ccg cct cca tcc agg cca ggt gta gga gcc cct cca cca ccg cca    1304
Pro Pro Pro Pro Ser Arg Pro Gly Val Gly Ala Pro Pro Pro Pro Pro
    325                 330                 335 aac agg atg tac cct cct cca ctt cca gct ctt ccc tcc tca gca cct    1352
Asn Arg Met Tyr Pro Pro Pro Leu Pro Ala Leu Pro Ser Ser Ala Pro
340                 345                 350                 355 tca ggg cct cca cca cca cct cca cct ctg tca gtg agc ggg tca gtg    1400
Ser Gly Pro Pro Pro Pro Pro Pro Leu Ser Val Ser Gly Ser Val
                360                 365                 370 gca cca cca cct ccg ccg cca cct cca cct cca ggg cca cca cct         1448
Ala Pro Pro Pro Pro Pro Pro Pro Pro Pro Gly Pro Pro Pro
            375                 380                 385 ccc cct ggc ctc cct tct gat ggt gac cac caa gtt cca act cct gca    1496
Pro Pro Gly Leu Pro Ser Asp Gly Asp His Gln Val Pro Thr Pro Ala
            390                 395                 400 gga agc aaa gca gct ctt tta gat caa att aga gag ggt gct cag cta    1544
Gly Ser Lys Ala Ala Leu Leu Asp Gln Ile Arg Glu Gly Ala Gln Leu
    405                 410                 415 aaa aaa gtg gaa cag aac agt cgg ccg gtg tcc tgc tct gga agg gat    1592
Lys Lys Val Glu Gln Asn Ser Arg Pro Val Ser Cys Ser Gly Arg Asp
420                 425                 430                 435
```

```
gca ctt tta gac cag ata cga cag ggt att caa ctg aaa tct gta act      1640
Ala Leu Leu Asp Gln Ile Arg Gln Gly Ile Gln Leu Lys Ser Val Thr
                440                 445                 450 gat gcc cca gag tct aca cca cca gca cct gca ccc act tca gga att      1688
Asp Ala Pro Glu Ser Thr Pro Pro Ala Pro Ala Pro Thr Ser Gly Ile
            455                 460                 465 gta ggt gca tta atg gaa gtg atg cag aag agg agc aaa gcc att cat      1736
Val Gly Ala Leu Met Glu Val Met Gln Lys Arg Ser Lys Ala Ile His
        470                 475                 480 tct tca gac gaa gat gag gat gaa gat gat gat gaa gat ttt gag gat      1784
Ser Ser Asp Glu Asp Glu Asp Glu Asp Asp Asp Glu Asp Phe Glu Asp
    485                 490                 495 gat gat gaa tgg gaa gac tgatctatat attatatata tatattttta aggt        1836
Asp Asp Glu Trp Glu Asp
500                 505

<210> SEQ ID NO 56
<211> LENGTH: 505
<212> TYPE: PRT
<213> ORGANISM: Bos taurus

<400> SEQUENCE: 56

Met Ser Ser Gly Gln Gln Pro Pro Pro Arg Arg Val Thr Asn
  1               5                  10                  15

Val Gly Ser Leu Leu Leu Thr Pro Gln Glu Asn Glu Ser Leu Phe Thr
             20                  25                  30

Phe Leu Gly Lys Lys Cys Val Thr Met Ser Ser Ala Val Val Gln Leu
         35                  40                  45

Tyr Ala Ala Asp Arg Asn Cys Met Trp Ser Lys Lys Cys Ser Gly Val
     50                  55                  60

Ala Cys Leu Val Lys Asp Asn Pro Gln Arg Ser Tyr Phe Leu Arg Ile
 65                  70                  75                  80

Phe Asp Ile Lys Asp Gly Lys Leu Leu Trp Glu Gln Glu Leu Tyr Asn
                 85                  90                  95

Asn Phe Val Tyr Asn Ser Pro Arg Gly Tyr Phe His Thr Phe Ala Gly
            100                 105                 110

Asp Thr Cys Gln Val Ala Leu Asn Phe Ala Asn Glu Glu Glu Ala Lys
        115                 120                 125

Lys Phe Arg Lys Ala Val Thr Asp Leu Leu Gly Arg Arg Gln Arg Lys
    130                 135                 140

Ser Glu Lys Arg Arg Asp Pro Pro Asn Gly Pro Asn Leu Pro Met Ala
145                 150                 155                 160

Thr Val Asp Ile Lys Asn Pro Glu Ile Thr Thr Asn Arg Phe Tyr Gly
                165                 170                 175

Pro Gln Ile Asn Asn Ile Ser His Thr Lys Glu Lys Lys Gly Lys
            180                 185                 190

Ala Lys Lys Lys Arg Leu Thr Lys Ala Asp Ile Gly Thr Pro Ser Asn
        195                 200                 205

Phe Gln His Ile Gly His Val Gly Trp Asp Pro Asn Thr Gly Phe Asp
    210                 215                 220

Leu Asn Asn Leu Asp Pro Glu Leu Lys Asn Leu Phe Asp Met Cys Gly
225                 230                 235                 240

Ile Ser Glu Ala Gln Leu Lys Asp Arg Glu Thr Ser Lys Val Ile Tyr
                245                 250                 255

Asp Phe Ile Glu Lys Thr Gly Gly Val Glu Ala Val Lys Asn Glu Leu
            260                 265                 270
```

```
Arg Arg Gln Ala Pro Pro Pro Pro Pro Ser Arg Gly Gly Pro Pro
        275                 280                 285
Pro Pro Pro Pro Pro Pro His Ser Ser Gly Pro Pro Pro Pro Ala
        290                 295                 300
Arg Gly Arg Gly Ala Pro Pro Pro Pro Ser Arg Ala Pro Thr Ala
305                 310                 315                 320
Ala Pro Pro Pro Pro Pro Ser Arg Pro Gly Val Gly Ala Pro Pro
                325                 330                 335
Pro Pro Pro Asn Arg Met Tyr Pro Pro Pro Leu Pro Ala Leu Pro Ser
                340                 345                 350
Ser Ala Pro Ser Gly Pro Pro Pro Pro Pro Leu Ser Val Ser
        355                 360                 365
Gly Ser Val Ala Pro Pro Pro Pro Pro Pro Pro Pro Pro Gly
        370                 375                 380
Pro Pro Pro Pro Pro Gly Leu Pro Ser Asp Gly Asp His Gln Val Pro
385                 390                 395                 400
Thr Pro Ala Gly Ser Lys Ala Ala Leu Leu Asp Gln Ile Arg Glu Gly
                405                 410                 415
Ala Gln Leu Lys Lys Val Glu Gln Asn Ser Arg Pro Val Ser Cys Ser
                420                 425                 430
Gly Arg Asp Ala Leu Leu Asp Gln Ile Arg Gln Gly Ile Gln Leu Lys
                435                 440                 445
Ser Val Thr Asp Ala Pro Glu Ser Thr Pro Pro Ala Pro Ala Pro Thr
        450                 455                 460
Ser Gly Ile Val Gly Ala Leu Met Glu Val Met Gln Lys Arg Ser Lys
465                 470                 475                 480
Ala Ile His Ser Ser Asp Glu Asp Glu Asp Glu Asp Asp Glu Asp
                485                 490                 495
Phe Glu Asp Asp Asp Glu Trp Glu Asp
            500                 505

<210> SEQ ID NO 57
<211> LENGTH: 303
<212> TYPE: DNA
<213> ORGANISM: Artificial sequence
<220> FEATURE:
<223> OTHER INFORMATION: Description of the artificial sequence:
      Fragment of the bovine N-WASP protein
<220> FEATURE:
<221> NAME/KEY: CDS
<222> LOCATION: (1)..(303)

<400> SEQUENCE: 57
agc aaa gca gct ctt tta gat caa att aga gag ggt gct cag cta aaa     48
Ser Lys Ala Ala Leu Leu Asp Gln Ile Arg Glu Gly Ala Gln Leu Lys
  1               5                  10                  15 aaa gtg gaa cag aac agt cgg ccg gtg tcc tgc tct gga agg gat gca     96
Lys Val Glu Gln Asn Ser Arg Pro Val Ser Cys Ser Gly Arg Asp Ala
             20                  25                  30 ctt tta gac cag ata cga cag ggt att caa ctg aaa tct gta act gat    144
Leu Leu Asp Gln Ile Arg Gln Gly Ile Gln Leu Lys Ser Val Thr Asp
         35                  40                  45 gcc cca gag tct aca cca cca gca cct gca ccc act tca gga att gta    192
Ala Pro Glu Ser Thr Pro Pro Ala Pro Ala Pro Thr Ser Gly Ile Val
     50                  55                  60 ggt gca tta atg gaa gtg atg cag aag agg agc aaa gcc att cat tct    240
Gly Ala Leu Met Glu Val Met Gln Lys Arg Ser Lys Ala Ile His Ser
 65                  70                  75                  80 tca gac gaa gat gag gat gaa gat gat gat gaa gat ttt gag gat gat    288
```

```
Ser Asp Glu Asp Glu Asp Glu Asp Asp Glu Asp Phe Glu Asp Asp
                85                  90                  95 gat gaa tgg gaa gac                                              303
Asp Glu Trp Glu Asp
            100

<210> SEQ ID NO 58
<211> LENGTH: 101
<212> TYPE: PRT
<213> ORGANISM: Artificial sequence
<220> FEATURE:
<223> OTHER INFORMATION: Description of the artificial sequence:
      Fragment of the bovine N-WASP protein

<400> SEQUENCE: 58

Ser Lys Ala Ala Leu Leu Asp Gln Ile Arg Glu Gly Ala Gln Leu Lys
  1               5                  10                  15

Lys Val Glu Gln Asn Ser Arg Pro Val Ser Cys Ser Gly Arg Asp Ala
                 20                  25                  30

Leu Leu Asp Gln Ile Arg Gln Gly Ile Gln Leu Lys Ser Val Thr Asp
             35                  40                  45

Ala Pro Glu Ser Thr Pro Pro Ala Pro Ala Pro Thr Ser Gly Ile Val
         50                  55                  60

Gly Ala Leu Met Glu Val Met Gln Lys Arg Ser Lys Ala Ile His Ser
 65                  70                  75                  80

Ser Asp Glu Asp Glu Asp Glu Asp Asp Glu Asp Phe Glu Asp Asp
                85                  90                  95

Asp Glu Trp Glu Asp
            100

<210> SEQ ID NO 59
<211> LENGTH: 252
<212> TYPE: DNA
<213> ORGANISM: Artificial sequence
<220> FEATURE:
<223> OTHER INFORMATION: Description of the artificial sequence:
      Fragment of the bovine N-WASP protein
<220> FEATURE:
<221> NAME/KEY: CDS
<222> LOCATION: (1)..(252)

<400> SEQUENCE: 59 agc aaa gca gct ctt tta gat caa att aga gag ggt gct cag cta aaa    48
Ser Lys Ala Ala Leu Leu Asp Gln Ile Arg Glu Gly Ala Gln Leu Lys
  1               5                  10                  15 aaa gtg gaa cag aac agt cgg ccg gtg tcc tgc tct gga agg gat gca    96
Lys Val Glu Gln Asn Ser Arg Pro Val Ser Cys Ser Gly Arg Asp Ala
                 20                  25                  30 ctt tta gac cag ata cga cag ggt att caa ctg aaa tct gta act gat   144
Leu Leu Asp Gln Ile Arg Gln Gly Ile Gln Leu Lys Ser Val Thr Asp
             35                  40                  45 gcc cca gag tct aca cca cca gca cct gca ccc act tca gga att gta   192
Ala Pro Glu Ser Thr Pro Pro Ala Pro Ala Pro Thr Ser Gly Ile Val
         50                  55                  60 ggt gca tta atg gaa gtg atg cag aag agg agc aaa gcc att cat tct   240
Gly Ala Leu Met Glu Val Met Gln Lys Arg Ser Lys Ala Ile His Ser
 65                  70                  75                  80 tca gac gaa gat                                                    252
Ser Asp Glu Asp

<210> SEQ ID NO 60
<211> LENGTH: 84
```

<212> TYPE: PRT
<213> ORGANISM: Artificial sequence
<220> FEATURE:
<223> OTHER INFORMATION: Description of the artificial sequence:
    Fragment of the bovine N-WASP protein

<400> SEQUENCE: 60

Ser Lys Ala Ala Leu Leu Asp Gln Ile Arg Glu Gly Ala Gln Leu Lys
  1               5                  10                  15

Lys Val Glu Gln Asn Ser Arg Pro Val Ser Cys Ser Gly Arg Asp Ala
             20                  25                  30

Leu Leu Asp Gln Ile Arg Gln Gly Ile Gln Leu Lys Ser Val Thr Asp
         35                  40                  45

Ala Pro Glu Ser Thr Pro Pro Ala Pro Ala Pro Thr Ser Gly Ile Val
     50                  55                  60

Gly Ala Leu Met Glu Val Met Gln Lys Arg Ser Lys Ala Ile His Ser
 65                  70                  75                  80
Ser Asp Glu Asp

<210> SEQ ID NO 61
<211> LENGTH: 219
<212> TYPE: DNA
<213> ORGANISM: Artificial sequence
<220> FEATURE:
<223> OTHER INFORMATION: Description of the artificial sequence:
    Fragment of the bovine N-WASP protein
<220> FEATURE:
<221> NAME/KEY: CDS
<222> LOCATION: (1)..(219)

<400> SEQUENCE: 61 gga agg gat gca ctt tta gac cag ata cga cag ggt att caa ctg aaa        48
Gly Arg Asp Ala Leu Leu Asp Gln Ile Arg Gln Gly Ile Gln Leu Lys
  1               5                  10                  15 tct gta act gat gcc cca gag tct aca cca cca gca cct gca ccc act        96
Ser Val Thr Asp Ala Pro Glu Ser Thr Pro Pro Ala Pro Ala Pro Thr
             20                  25                  30 tca gga att gta ggt gca tta atg gaa gtg atg cag aag agg agc aaa       144
Ser Gly Ile Val Gly Ala Leu Met Glu Val Met Gln Lys Arg Ser Lys
         35                  40                  45 gcc att cat tct tca gac gaa gat gag gat gaa gat gat gaa gat           192
Ala Ile His Ser Ser Asp Glu Asp Glu Asp Glu Asp Asp Glu Asp
     50                  55                  60 ttt gag gat gat gat gaa tgg gaa gac                                   219
Phe Glu Asp Asp Asp Glu Trp Glu Asp
 65                  70

<210> SEQ ID NO 62
<211> LENGTH: 73
<212> TYPE: PRT
<213> ORGANISM: Artificial sequence
<220> FEATURE:
<223> OTHER INFORMATION: Description of the artificial sequence:
    Fragment of the bovine N-WASP protein

<400> SEQUENCE: 62

Gly Arg Asp Ala Leu Leu Asp Gln Ile Arg Gln Gly Ile Gln Leu Lys
  1               5                  10                  15

Ser Val Thr Asp Ala Pro Glu Ser Thr Pro Pro Ala Pro Ala Pro Thr
             20                  25                  30

Ser Gly Ile Val Gly Ala Leu Met Glu Val Met Gln Lys Arg Ser Lys
         35                  40                  45

Ala Ile His Ser Ser Asp Glu Asp Glu Asp Glu Asp Asp Glu Asp

```
                  50                  55                  60
Phe Glu Asp Asp Asp Glu Trp Glu Asp
 65                  70

<210> SEQ ID NO 63
<211> LENGTH: 168
<212> TYPE: DNA
<213> ORGANISM: Artificial sequence
<220> FEATURE:
<223> OTHER INFORMATION: Description of the artificial sequence:
      Fragment of the bovine N-WASP protein
<220> FEATURE:
<221> NAME/KEY: CDS
<222> LOCATION: (1)..(168)

<400> SEQUENCE: 63 gga agg gat gca ctt tta gac cag ata cga cag ggt att caa ctg aaa        48
Gly Arg Asp Ala Leu Leu Asp Gln Ile Arg Gln Gly Ile Gln Leu Lys
  1               5                  10                  15 tct gta act gat gcc cca gag tct aca cca cca gca cct gca ccc act        96
Ser Val Thr Asp Ala Pro Glu Ser Thr Pro Pro Ala Pro Ala Pro Thr
                 20                  25                  30 tca gga att gta ggt gca tta atg gaa gtg atg cag aag agg agc aaa       144
Ser Gly Ile Val Gly Ala Leu Met Glu Val Met Gln Lys Arg Ser Lys
             35                  40                  45 gcc att cat tct tca gac gaa gat                                       168
Ala Ile His Ser Ser Asp Glu Asp
         50                  55

<210> SEQ ID NO 64
<211> LENGTH: 56
<212> TYPE: PRT
<213> ORGANISM: Artificial sequence
<220> FEATURE:
<223> OTHER INFORMATION: Description of the artificial sequence:
      Fragment of the bovine N-WASP protein

<400> SEQUENCE: 64

Gly Arg Asp Ala Leu Leu Asp Gln Ile Arg Gln Gly Ile Gln Leu Lys
  1               5                  10                  15

Ser Val Thr Asp Ala Pro Glu Ser Thr Pro Pro Ala Pro Ala Pro Thr
                 20                  25                  30

Ser Gly Ile Val Gly Ala Leu Met Glu Val Met Gln Lys Arg Ser Lys
             35                  40                  45

Ala Ile His Ser Ser Asp Glu Asp
         50                  55

<210> SEQ ID NO 65
<211> LENGTH: 3023
<212> TYPE: DNA
<213> ORGANISM: Saccharomyces cerevisiae
<220> FEATURE:
<221> NAME/KEY: CDS
<222> LOCATION: (772)..(2670)

<400> SEQUENCE: 65
agttagaaga taactcacta gacttaacac cagaaaatcc tactctgtaa taaaataatc        60
ccggggtaat ggattggatt tttctatcag gatcgtttac gtatatataa tacactgtcg       120
gagtttagcg cgcttacagc cgctacttgt ggagtccttt tttttttttt tttttggg         180 tttcagacat ccagtaaaga atagaaacaa gcaacaaact tcagaactga aacaatgctt       240
ttttaagtta tcgcctaaat atattcaaaa aatatagata tgctagattt tcaattatac       300
```

```
caaagttcat attttcaaaa tgaatgttaa caaaaagaca agttgatggc ccttttttcat    360 aaagtatgcg tttagtttca agtaacgccg gctgacgtgg acgatttatc aaagaagtgg    420
ttttggaata ctcttctttt gcaattagaa aaaaggcaaa actaaatgca atgcaagcag    480
ttgcccatgg tacttgaaat tgtgtctctg gtttaaaaga tctatgatat aagtcttaac    540
tgatcttata gttgttttttt tttgaatttt ccaaatagtt tatatgatca ttgaatacgt    600
gcgagacgtc cgaaaagggg ccagtcaata cctatgaaaa aaaatcatga atatgtaata    660
ataaatattg aatgtagaat atacatagta gaaaaggaag tgctgtagcg attgccatct    720
ccgctacaaa ttacagttcg ttactttaag tgttgatagg cgtgatttaa t atg gga     777
                                                          Met Gly
                                                            1 ctc cta aac tct tca gat aag gaa att atc aaa agg gct cta cca aaa      825
Leu Leu Asn Ser Ser Asp Lys Glu Ile Ile Lys Arg Ala Leu Pro Lys
          5                  10                  15 gcg tcg aat aag att att gat gtt acg gtg gct cga cta tac att gca      873
Ala Ser Asn Lys Ile Ile Asp Val Thr Val Ala Arg Leu Tyr Ile Ala
     20                  25                  30 tac cct gat aaa aat gaa tgg cag tac act gga ctt tca gga gct ctt      921
Tyr Pro Asp Lys Asn Glu Trp Gln Tyr Thr Gly Leu Ser Gly Ala Leu
 35                  40                  45                  50 gct cta gta gac gat ctt gtg ggg aat act ttt ttt ttg aaa tta gtt      969
Ala Leu Val Asp Asp Leu Val Gly Asn Thr Phe Phe Leu Lys Leu Val
              55                  60                  65 gac atc aat ggc cat aga gga gtt atc tgg gac caa gaa ttg tat gtg      1017
Asp Ile Asn Gly His Arg Gly Val Ile Trp Asp Gln Glu Leu Tyr Val
          70                  75                  80 aat ttt gaa tac tat caa gac cgt act ttt ttt cat aca ttt gag atg      1065
Asn Phe Glu Tyr Tyr Gln Asp Arg Thr Phe Phe His Thr Phe Glu Met
     85                  90                  95 gaa gaa tgc ttt gca ggt tta ttg ttt gta gat att aat gaa gca tcg      1113
Glu Glu Cys Phe Ala Gly Leu Leu Phe Val Asp Ile Asn Glu Ala Ser
100                 105                 110 cac ttt tta aag aga gtt caa aag cgt gaa aga tat gct aac agg aaa      1161
His Phe Leu Lys Arg Val Gln Lys Arg Glu Arg Tyr Ala Asn Arg Lys
115                 120                 125                 130 act ttg ttg aac aaa aat gct gta gca tta acc aag aaa gta aga gaa      1209
Thr Leu Leu Asn Lys Asn Ala Val Ala Leu Thr Lys Lys Val Arg Glu
              135                 140                 145 gaa caa aaa tct caa gtg gtg cac ggc cca aga ggg gag tca ttg att      1257
Glu Gln Lys Ser Gln Val Val His Gly Pro Arg Gly Glu Ser Leu Ile
          150                 155                 160 gac aat caa agg aaa aga tat aat tat gaa gat gtg gac aca att cca      1305
Asp Asn Gln Arg Lys Arg Tyr Asn Tyr Glu Asp Val Asp Thr Ile Pro
     165                 170                 175 act aca aag cat aag gct cct ccc cct cct ccg cca acg gcc gaa aca      1353
Thr Thr Lys His Lys Ala Pro Pro Pro Pro Pro Pro Thr Ala Glu Thr
180                 185                 190 ttt gat tca gac caa aca agt tca ttt tcc gat atc aat tcg aca aca      1401
Phe Asp Ser Asp Gln Thr Ser Ser Phe Ser Asp Ile Asn Ser Thr Thr
195                 200                 205                 210 gca tcc gca ccg act acc cca gcc cct gct ctt cct cct gca tct cct      1449
Ala Ser Ala Pro Thr Thr Pro Ala Pro Ala Leu Pro Pro Ala Ser Pro
              215                 220                 225 gaa gta aga aaa gaa gaa acg cat cca aag cat agt tta ccg cct tta      1497
Glu Val Arg Lys Glu Glu Thr His Pro Lys His Ser Leu Pro Pro Leu
          230                 235                 240 cca aat cag ttt gcg cca tta cca gac cct cca caa cat aac tct cca      1545
```

```
                Pro Asn Gln Phe Ala Pro Leu Pro Asp Pro Pro Gln His Asn Ser Pro
                        245                 250                 255 cct caa aat aac gcg cct tcg caa ccc caa agc aat cca ttt cca ttc           1593
Pro Gln Asn Asn Ala Pro Ser Gln Pro Gln Ser Asn Pro Phe Pro Phe
        260                 265                 270 cca att cct gaa att ccc tcg aca cag tct gca aca aac cca ttt cca           1641
Pro Ile Pro Glu Ile Pro Ser Thr Gln Ser Ala Thr Asn Pro Phe Pro
275                 280                 285                 290 ttt ccg gta cct cag cag cag ttt aat caa gct cct tca atg gga ata           1689
Phe Pro Val Pro Gln Gln Gln Phe Asn Gln Ala Pro Ser Met Gly Ile
                295                 300                 305 cca cag cag aat agg ccc ctt cca cag ttg cct aac aga aat aat cgg           1737
Pro Gln Gln Asn Arg Pro Leu Pro Gln Leu Pro Asn Arg Asn Asn Arg
        310                 315                 320 cct gtg cca cct cct ccg cca atg cgt acc act act gaa ggt tca ggt           1785
Pro Val Pro Pro Pro Pro Pro Met Arg Thr Thr Thr Glu Gly Ser Gly
        325                 330                 335 gtt cgc cta cct gct cct cca cct ccg cca agg cgt ggg cca gca cca           1833
Val Arg Leu Pro Ala Pro Pro Pro Pro Pro Arg Arg Gly Pro Ala Pro
        340                 345                 350 ccg cct cca cca cat agg cac gta acc agt aat acc ctg aat tct gcc           1881
Pro Pro Pro Pro His Arg His Val Thr Ser Asn Thr Leu Asn Ser Ala
355                 360                 365                 370 ggt gga aat agc ctc ctt cca cag gcc act gga aga aga ggg cca gca           1929
Gly Gly Asn Ser Leu Leu Pro Gln Ala Thr Gly Arg Arg Gly Pro Ala
                375                 380                 385 cca cca cct cct cca aga gca tct cgc ccc aca cca aac gtt acg atg           1977
Pro Pro Pro Pro Pro Arg Ala Ser Arg Pro Thr Pro Asn Val Thr Met
        390                 395                 400 caa caa aat cca caa cag tac aat aat tct aac cgc ccc ttt gga tat           2025
Gln Gln Asn Pro Gln Gln Tyr Asn Asn Ser Asn Arg Pro Phe Gly Tyr
        405                 410                 415 cag aca aat agc aac atg tca tct cca ccc cct cct cca gtg aca act           2073
Gln Thr Asn Ser Asn Met Ser Ser Pro Pro Pro Pro Pro Val Thr Thr
        420                 425                 430 ttc aat acc ctg aca cca caa atg act gca gca act gga caa cct gca           2121
Phe Asn Thr Leu Thr Pro Gln Met Thr Ala Ala Thr Gly Gln Pro Ala
435                 440                 445                 450 gtt ccc ctt cct cag aat act caa gca cct tcg caa gcc aca aat gtg           2169
Val Pro Leu Pro Gln Asn Thr Gln Ala Pro Ser Gln Ala Thr Asn Val
                455                 460                 465 cca gtg gca cca cca cct cct ccg gca tct tta ggc cag tcg cag ata           2217
Pro Val Ala Pro Pro Pro Pro Pro Ala Ser Leu Gly Gln Ser Gln Ile
        470                 475                 480 cct cag tca gca ccc tca gca cct att ccg cca acg tta cca tcg acg           2265
Pro Gln Ser Ala Pro Ser Ala Pro Ile Pro Pro Thr Leu Pro Ser Thr
        485                 490                 495 acg agt gct gca cca cct ccg cca cca gca ttc cta act caa caa cct           2313
Thr Ser Ala Ala Pro Pro Pro Pro Pro Ala Phe Leu Thr Gln Gln Pro
        500                 505                 510 caa tct gga gga gct cca gct cca ccc cca cct cct caa atg cca gct           2361
Gln Ser Gly Gly Ala Pro Ala Pro Pro Pro Pro Gln Met Pro Ala
515                 520                 525                 530 aca tca aca tcc gga ggc ggt tca ttc gct gaa act act gga gat gca           2409
Thr Ser Thr Ser Gly Gly Gly Ser Phe Ala Glu Thr Thr Gly Asp Ala
                535                 540                 545 ggt cgt gat gca ctt tta gct tca att aga ggg gca ggt ggc ata ggc           2457
Gly Arg Asp Ala Leu Leu Ala Ser Ile Arg Gly Ala Gly Gly Ile Gly
        550                 555                 560
```

-continued

```
gct ttg aga aaa gtt gac aaa tcg cag cta gat aag ccc tca gtt tta      2505
Ala Leu Arg Lys Val Asp Lys Ser Gln Leu Asp Lys Pro Ser Val Leu
            565                 570                 575 ctg cag gaa gca cgt gga gaa tct gct tca cca cca gca gcg gct gga      2553
Leu Gln Glu Ala Arg Gly Glu Ser Ala Ser Pro Pro Ala Ala Ala Gly
        580                 585                 590 aat gga ggc aca cct ggt gga cct ccg gct tct tta gca gat gcg ttg      2601
Asn Gly Gly Thr Pro Gly Gly Pro Pro Ala Ser Leu Ala Asp Ala Leu
595                 600                 605                 610 gca gca gct tta aac aaa aga aaa act aaa gtg gga gct cat gac gat      2649
Ala Ala Ala Leu Asn Lys Arg Lys Thr Lys Val Gly Ala His Asp Asp
                615                 620                 625 atg gac aat ggt gat gat tgg taatggaatg caaacaaaga tgaaactact         2700
Met Asp Asn Gly Asp Asp Trp
            630 gttatagaaa atatgtaatt ttatgtactc actattaatg atcaaagtaa ttgctctttt    2760 tatgtatagt ttctttaatc ggaggaaatt ttgatatagg ttcaaaggcg gtcagtgatt    2820 gaatgatcaa ggtaatagtc gggctacaat gatggccatc cctatggccg tttcaaatgt    2880 ttgagaaaat gatgtatagt aaatcctaga ttttagcagt tcgaatcaaa aacccatgta    2940 aaaagggtaa atatttccta attataatat ttttgtttaa ttacacatgt agaacaataa    3000 aagtatagaa ttttagatag tat                                           3023
```

<210> SEQ ID NO 66
<211> LENGTH: 633
<212> TYPE: PRT
<213> ORGANISM: Saccharomyces cerevisiae

<400> SEQUENCE: 66

```
Met Gly Leu Leu Asn Ser Ser Asp Lys Glu Ile Ile Lys Arg Ala Leu
  1               5                  10                  15

Pro Lys Ala Ser Asn Lys Ile Ile Asp Val Thr Val Ala Arg Leu Tyr
             20                  25                  30

Ile Ala Tyr Pro Asp Lys Asn Glu Trp Gln Tyr Thr Gly Leu Ser Gly
         35                  40                  45

Ala Leu Ala Leu Val Asp Asp Leu Val Gly Asn Thr Phe Phe Leu Lys
     50                  55                  60

Leu Val Asp Ile Asn Gly His Arg Gly Val Ile Trp Asp Gln Glu Leu
 65                  70                  75                  80

Tyr Val Asn Phe Glu Tyr Tyr Gln Asp Arg Thr Phe Phe His Thr Phe
                 85                  90                  95

Glu Met Glu Glu Cys Phe Ala Gly Leu Leu Phe Val Asp Ile Asn Glu
            100                 105                 110

Ala Ser His Phe Leu Lys Arg Val Gln Lys Arg Glu Arg Tyr Ala Asn
        115                 120                 125

Arg Lys Thr Leu Leu Asn Lys Asn Ala Val Ala Leu Thr Lys Lys Val
    130                 135                 140

Arg Glu Glu Gln Lys Ser Gln Val Val His Gly Pro Arg Gly Glu Ser
145                 150                 155                 160

Leu Ile Asp Asn Gln Arg Lys Arg Tyr Asn Tyr Glu Asp Val Asp Thr
                165                 170                 175

Ile Pro Thr Thr Lys His Lys Ala Pro Pro Pro Pro Thr Ala
            180                 185                 190

Glu Thr Phe Asp Ser Asp Gln Thr Ser Ser Phe Ser Asp Ile Asn Ser
        195                 200                 205
```

-continued

```
Thr Thr Ala Ser Ala Pro Thr Pro Ala Pro Ala Leu Pro Pro Ala
    210                 215                 220

Ser Pro Glu Val Arg Lys Glu Glu Thr His Pro Lys His Ser Leu Pro
225                 230                 235                 240

Pro Leu Pro Asn Gln Phe Ala Pro Leu Pro Asp Pro Pro Gln His Asn
                245                 250                 255

Ser Pro Pro Gln Asn Asn Ala Pro Ser Gln Pro Gln Ser Asn Pro Phe
                260                 265                 270

Pro Phe Pro Ile Pro Glu Ile Pro Ser Thr Gln Ser Ala Thr Asn Pro
                275                 280                 285

Phe Pro Phe Pro Val Pro Gln Gln Phe Asn Gln Ala Pro Ser Met
    290                 295                 300

Gly Ile Pro Gln Gln Asn Arg Pro Leu Pro Gln Leu Pro Asn Arg Asn
305                 310                 315                 320

Asn Arg Pro Val Pro Pro Pro Pro Met Arg Thr Thr Thr Glu Gly
                325                 330                 335

Ser Gly Val Arg Leu Pro Ala Pro Pro Pro Pro Arg Arg Gly Pro
                340                 345                 350

Ala Pro Pro Pro Pro His Arg His Val Thr Ser Asn Thr Leu Asn
                355                 360                 365

Ser Ala Gly Gly Asn Ser Leu Leu Pro Gln Ala Thr Gly Arg Arg Gly
    370                 375                 380

Pro Ala Pro Pro Pro Pro Arg Ala Ser Arg Pro Thr Pro Asn Val
385                 390                 395                 400

Thr Met Gln Gln Asn Pro Gln Gln Tyr Asn Asn Ser Asn Arg Pro Phe
                405                 410                 415

Gly Tyr Gln Thr Asn Ser Asn Met Ser Ser Pro Pro Pro Pro Val
                420                 425                 430

Thr Thr Phe Asn Thr Leu Thr Pro Gln Met Thr Ala Ala Thr Gly Gln
                435                 440                 445

Pro Ala Val Pro Leu Pro Gln Asn Thr Gln Ala Pro Ser Gln Ala Thr
    450                 455                 460

Asn Val Pro Val Ala Pro Pro Pro Pro Ala Ser Leu Gly Gln Ser
465                 470                 475                 480

Gln Ile Pro Gln Ser Ala Pro Ser Ala Pro Ile Pro Pro Thr Leu Pro
                485                 490                 495

Ser Thr Thr Ser Ala Ala Pro Pro Pro Pro Ala Phe Leu Thr Gln
                500                 505                 510

Gln Pro Gln Ser Gly Gly Ala Pro Ala Pro Pro Pro Pro Gln Met
    515                 520                 525

Pro Ala Thr Ser Thr Ser Gly Gly Gly Ser Phe Ala Glu Thr Thr Gly
    530                 535                 540

Asp Ala Gly Arg Asp Ala Leu Leu Ala Ser Ile Arg Gly Ala Gly Gly
545                 550                 555                 560

Ile Gly Ala Leu Arg Lys Val Asp Lys Ser Gln Leu Asp Lys Pro Ser
                565                 570                 575

Val Leu Leu Gln Glu Ala Arg Gly Glu Ser Ala Ser Pro Pro Ala Ala
                580                 585                 590

Ala Gly Asn Gly Gly Thr Pro Gly Pro Pro Ala Ser Leu Ala Asp
    595                 600                 605

Ala Leu Ala Ala Ala Leu Asn Lys Arg Lys Thr Lys Val Gly Ala His
    610                 615                 620

Asp Asp Met Asp Asn Gly Asp Asp Trp
```

<210> SEQ ID NO 67
<211> LENGTH: 636
<212> TYPE: DNA
<213> ORGANISM: Artificial sequence
<220> FEATURE:
<223> OTHER INFORMATION: Description of the artificial sequence:
    Fragment of the Saccharomyces cerevisiae Las17 protein
<220> FEATURE:
<221> NAME/KEY: CDS
<222> LOCATION: (1)..(636)

<400> SEQUENCE: 67

| | | | | | | | | | | | | | | | | |
|---|---|---|---|---|---|---|---|---|---|---|---|---|---|---|---|---|
| agc | aac | atg | tca | tct | cca | ccc | cct | cct | cca | gtg | aca | act | ttc | aat | acc | 48 |
| Ser | Asn | Met | Ser | Ser | Pro | Pro | Pro | Pro | Pro | Val | Thr | Thr | Phe | Asn | Thr | |
| 1 | | | | 5 | | | | | 10 | | | | | 15 | | |
| ctg | aca | cca | caa | atg | act | gca | gca | act | gga | caa | cct | gca | gtt | ccc | ctt | 96 |
| Leu | Thr | Pro | Gln | Met | Thr | Ala | Ala | Thr | Gly | Gln | Pro | Ala | Val | Pro | Leu | |
| | | | 20 | | | | | 25 | | | | | 30 | | | |
| cct | cag | aat | act | caa | gca | cct | tcg | caa | gcc | aca | aat | gtg | cca | gtg | gca | 144 |
| Pro | Gln | Asn | Thr | Gln | Ala | Pro | Ser | Gln | Ala | Thr | Asn | Val | Pro | Val | Ala | |
| | | 35 | | | | | 40 | | | | | 45 | | | | |
| cca | cca | cct | cct | ccg | gca | tct | tta | ggc | cag | tcg | cag | ata | cct | cag | tca | 192 |
| Pro | Pro | Pro | Pro | Pro | Ala | Ser | Leu | Gly | Gln | Ser | Gln | Ile | Pro | Gln | Ser | |
| 50 | | | | | 55 | | | | | 60 | | | | | | |
| gca | ccc | tca | gca | cct | att | ccg | cca | acg | tta | cca | tcg | acg | acg | agt | gct | 240 |
| Ala | Pro | Ser | Ala | Pro | Ile | Pro | Pro | Thr | Leu | Pro | Ser | Thr | Thr | Ser | Ala | |
| 65 | | | | 70 | | | | | 75 | | | | | 80 | | |
| gca | cca | cct | ccg | cca | cca | gca | ttc | cta | act | caa | caa | cct | caa | tct | gga | 288 |
| Ala | Pro | Pro | Pro | Pro | Pro | Ala | Phe | Leu | Thr | Gln | Gln | Pro | Gln | Ser | Gly | |
| | | | 85 | | | | | 90 | | | | | 95 | | | |
| gga | gct | cca | gct | cca | ccc | cca | cct | cct | caa | atg | cca | gct | aca | tca | aca | 336 |
| Gly | Ala | Pro | Ala | Pro | Pro | Pro | Pro | Pro | Gln | Met | Pro | Ala | Thr | Ser | Thr | |
| | | | 100 | | | | | 105 | | | | | 110 | | | |
| tcc | gga | ggc | ggt | tca | ttc | gct | gaa | act | act | gga | gat | gca | ggt | cgt | gat | 384 |
| Ser | Gly | Gly | Gly | Ser | Phe | Ala | Glu | Thr | Thr | Gly | Asp | Ala | Gly | Arg | Asp | |
| | | 115 | | | | | 120 | | | | | 125 | | | | |
| gca | ctt | tta | gct | tca | att | aga | ggg | gca | ggt | ggc | ata | ggc | gct | ttg | aga | 432 |
| Ala | Leu | Leu | Ala | Ser | Ile | Arg | Gly | Ala | Gly | Gly | Ile | Gly | Ala | Leu | Arg | |
| | 130 | | | | | 135 | | | | | 140 | | | | | |
| aaa | gtt | gac | aaa | tcg | cag | cta | gat | aag | ccc | tca | gtt | tta | ctg | cag | gaa | 480 |
| Lys | Val | Asp | Lys | Ser | Gln | Leu | Asp | Lys | Pro | Ser | Val | Leu | Leu | Gln | Glu | |
| 145 | | | | | 150 | | | | | 155 | | | | | 160 | |
| gca | cgt | gga | gaa | tct | gct | tca | cca | cca | gca | gcg | gct | gga | aat | gga | ggc | 528 |
| Ala | Arg | Gly | Glu | Ser | Ala | Ser | Pro | Pro | Ala | Ala | Ala | Gly | Asn | Gly | Gly | |
| | | | 165 | | | | | 170 | | | | | 175 | | | |
| aca | cct | ggt | gga | cct | ccg | gct | tct | tta | gca | gat | gcg | ttg | gca | gca | gct | 576 |
| Thr | Pro | Gly | Gly | Pro | Pro | Ala | Ser | Leu | Ala | Asp | Ala | Leu | Ala | Ala | Ala | |
| | | | 180 | | | | | 185 | | | | | 190 | | | |
| tta | aac | aaa | aga | aaa | act | aaa | gtg | gga | gct | cat | gac | gat | atg | gac | aat | 624 |
| Leu | Asn | Lys | Arg | Lys | Thr | Lys | Val | Gly | Ala | His | Asp | Asp | Met | Asp | Asn | |
| | | 195 | | | | | 200 | | | | | 205 | | | | |
| ggt | gat | gat | tgg | | | | | | | | | | | | | 636 |
| Gly | Asp | Asp | Trp | | | | | | | | | | | | | |
| | 210 | | | | | | | | | | | | | | | |

<210> SEQ ID NO 68
<211> LENGTH: 212
<212> TYPE: PRT
<213> ORGANISM: Artificial sequence
<220> FEATURE:
<223> OTHER INFORMATION: Description of the artificial sequence:

Fragment of the Saccharomyces cerevisiae Las17 protein

<400> SEQUENCE: 68

| Ser | Asn | Met | Ser | Ser | Pro | Pro | Pro | Pro | Val | Thr | Thr | Phe | Asn | Thr |
|---|---|---|---|---|---|---|---|---|---|---|---|---|---|---|
| 1 | | | | 5 | | | | | 10 | | | | | 15 |

| Leu | Thr | Pro | Gln | Met | Thr | Ala | Ala | Thr | Gly | Gln | Pro | Ala | Val | Pro | Leu |
|---|---|---|---|---|---|---|---|---|---|---|---|---|---|---|---|
| | | | | 20 | | | | | 25 | | | | | 30 | |

| Pro | Gln | Asn | Thr | Gln | Ala | Pro | Ser | Gln | Ala | Thr | Asn | Val | Pro | Val | Ala |
|---|---|---|---|---|---|---|---|---|---|---|---|---|---|---|---|
| | | | 35 | | | | | 40 | | | | | 45 | | |

| Pro | Pro | Pro | Pro | Pro | Ala | Ser | Leu | Gly | Gln | Ser | Gln | Ile | Pro | Gln | Ser |
|---|---|---|---|---|---|---|---|---|---|---|---|---|---|---|---|
| | 50 | | | | | 55 | | | | | 60 | | | | |

| Ala | Pro | Ser | Ala | Pro | Ile | Pro | Pro | Thr | Leu | Pro | Ser | Thr | Thr | Ser | Ala |
|---|---|---|---|---|---|---|---|---|---|---|---|---|---|---|---|
| 65 | | | | | 70 | | | | | 75 | | | | | 80 |

| Ala | Pro | Pro | Pro | Pro | Ala | Phe | Leu | Thr | Gln | Gln | Pro | Gln | Ser | Gly |
|---|---|---|---|---|---|---|---|---|---|---|---|---|---|---|
| | | | | 85 | | | | | 90 | | | | | 95 |

| Gly | Ala | Pro | Ala | Pro | Pro | Pro | Pro | Gln | Met | Pro | Ala | Thr | Ser | Thr |
|---|---|---|---|---|---|---|---|---|---|---|---|---|---|---|
| | | | 100 | | | | | 105 | | | | | 110 | |

| Ser | Gly | Gly | Gly | Ser | Phe | Ala | Glu | Thr | Thr | Gly | Asp | Ala | Gly | Arg | Asp |
|---|---|---|---|---|---|---|---|---|---|---|---|---|---|---|---|
| | | 115 | | | | | 120 | | | | | 125 | | | |

| Ala | Leu | Leu | Ala | Ser | Ile | Arg | Gly | Ala | Gly | Gly | Ile | Gly | Ala | Leu | Arg |
|---|---|---|---|---|---|---|---|---|---|---|---|---|---|---|---|
| | 130 | | | | | 135 | | | | | 140 | | | | |

| Lys | Val | Asp | Lys | Ser | Gln | Leu | Asp | Lys | Pro | Ser | Val | Leu | Leu | Gln | Glu |
|---|---|---|---|---|---|---|---|---|---|---|---|---|---|---|---|
| 145 | | | | | 150 | | | | | 155 | | | | | 160 |

| Ala | Arg | Gly | Glu | Ser | Ala | Ser | Pro | Pro | Ala | Ala | Ala | Gly | Asn | Gly | Gly |
|---|---|---|---|---|---|---|---|---|---|---|---|---|---|---|---|
| | | | | 165 | | | | | 170 | | | | | 175 | |

| Thr | Pro | Gly | Gly | Pro | Pro | Ala | Ser | Leu | Ala | Asp | Ala | Leu | Ala | Ala | Ala |
|---|---|---|---|---|---|---|---|---|---|---|---|---|---|---|---|
| | | | 180 | | | | | 185 | | | | | 190 | | |

| Leu | Asn | Lys | Arg | Lys | Thr | Lys | Val | Gly | Ala | His | Asp | Asp | Met | Asp | Asn |
|---|---|---|---|---|---|---|---|---|---|---|---|---|---|---|---|
| | | 195 | | | | | 200 | | | | | 205 | | | |

| Gly | Asp | Asp | Trp |
|---|---|---|---|
| | 210 | | |

<210> SEQ ID NO 69
<211> LENGTH: 609
<212> TYPE: DNA
<213> ORGANISM: Artificial sequence
<220> FEATURE:
<223> OTHER INFORMATION: Description of the artificial sequence:
      Fragment of the Saccharomyces cerevisiae Las17 protein
<220> FEATURE:
<221> NAME/KEY: CDS
<222> LOCATION: (1)..(609)

<400> SEQUENCE: 69

```
agc aac atg tca tct cca ccc cct cct cca gtg aca act ttc aat acc      48
Ser Asn Met Ser Ser Pro Pro Pro Pro Val Thr Thr Phe Asn Thr
 1               5                  10                  15 ctg aca cca caa atg act gca gca act gga caa cct gca gtt ccc ctt      96
Leu Thr Pro Gln Met Thr Ala Ala Thr Gly Gln Pro Ala Val Pro Leu
                 20                  25                  30 cct cag aat act caa gca cct tcg caa gcc aca aat gtg cca gtg gca     144
Pro Gln Asn Thr Gln Ala Pro Ser Gln Ala Thr Asn Val Pro Val Ala
             35                  40                  45 cca cca cct cct ccg gca tct tta ggc cag tcg cag ata cct cag tca     192
Pro Pro Pro Pro Pro Ala Ser Leu Gly Gln Ser Gln Ile Pro Gln Ser
         50                  55                  60 gca ccc tca gca cct att ccg cca acg tta cca tcg acg acg agt gct     240
Ala Pro Ser Ala Pro Ile Pro Pro Thr Leu Pro Ser Thr Thr Ser Ala
 65                  70                  75                  80
```

```
gca cca cct ccg cca cca gca ttc cta act caa caa cct caa tct gga     288
Ala Pro Pro Pro Pro Ala Phe Leu Thr Gln Gln Pro Gln Ser Gly
            85                  90                  95 gga gct cca gct cca ccc cca cct cct caa atg cca gct aca tca aca     336
Gly Ala Pro Ala Pro Pro Pro Pro Gln Met Pro Ala Thr Ser Thr
        100                 105                 110 tcc gga ggc ggt tca ttc gct gaa act act gga gat gca ggt cgt gat     384
Ser Gly Gly Gly Ser Phe Ala Glu Thr Thr Gly Asp Ala Gly Arg Asp
        115                 120                 125 gca ctt tta gct tca att aga ggg gca ggt ggc ata ggc gct ttg aga     432
Ala Leu Leu Ala Ser Ile Arg Gly Ala Gly Gly Ile Gly Ala Leu Arg
130                 135                 140 aaa gtt gac aaa tcg cag cta gat aag ccc tca gtt tta ctg cag gaa     480
Lys Val Asp Lys Ser Gln Leu Asp Lys Pro Ser Val Leu Leu Gln Glu
145                 150                 155                 160 gca cgt gga gaa tct gct tca cca cca gca gcg gct gga aat gga ggc     528
Ala Arg Gly Glu Ser Ala Ser Pro Pro Ala Ala Ala Gly Asn Gly Gly
                165                 170                 175 aca cct ggt gga cct ccg gct tct tta gca gat gcg ttg gca gca gct     576
Thr Pro Gly Gly Pro Pro Ala Ser Leu Ala Asp Ala Leu Ala Ala Ala
        180                 185                 190 tta aac aaa aga aaa act aaa gtg gga gct cat                         609
Leu Asn Lys Arg Lys Thr Lys Val Gly Ala His
        195                 200

<210> SEQ ID NO 70
<211> LENGTH: 203
<212> TYPE: PRT
<213> ORGANISM: Artificial sequence
<220> FEATURE:
<223> OTHER INFORMATION: Description of the artificial sequence:
      Fragment of the Saccharomyces cerevisiae Las17 protein

<400> SEQUENCE: 70

Ser Asn Met Ser Ser Pro Pro Pro Pro Val Thr Thr Phe Asn Thr
 1               5                  10                  15

Leu Thr Pro Gln Met Thr Ala Ala Thr Gly Gln Pro Ala Val Pro Leu
                20                  25                  30

Pro Gln Asn Thr Gln Ala Pro Ser Gln Ala Thr Asn Val Pro Val Ala
            35                  40                  45

Pro Pro Pro Pro Ala Ser Leu Gly Gln Ser Gln Ile Pro Gln Ser
        50                  55                  60

Ala Pro Ser Ala Pro Ile Pro Pro Thr Leu Pro Ser Thr Thr Ser Ala
65                  70                  75                  80

Ala Pro Pro Pro Pro Ala Phe Leu Thr Gln Gln Pro Gln Ser Gly
            85                  90                  95

Gly Ala Pro Ala Pro Pro Pro Pro Gln Met Pro Ala Thr Ser Thr
        100                 105                 110

Ser Gly Gly Gly Ser Phe Ala Glu Thr Thr Gly Asp Ala Gly Arg Asp
        115                 120                 125

Ala Leu Leu Ala Ser Ile Arg Gly Ala Gly Gly Ile Gly Ala Leu Arg
130                 135                 140

Lys Val Asp Lys Ser Gln Leu Asp Lys Pro Ser Val Leu Leu Gln Glu
145                 150                 155                 160

Ala Arg Gly Glu Ser Ala Ser Pro Pro Ala Ala Ala Gly Asn Gly Gly
                165                 170                 175

Thr Pro Gly Gly Pro Pro Ala Ser Leu Ala Asp Ala Leu Ala Ala Ala
        180                 185                 190
```

Leu Asn Lys Arg Lys Thr Lys Val Gly Ala His
        195                 200

<210> SEQ ID NO 71
<211> LENGTH: 561
<212> TYPE: DNA
<213> ORGANISM: Artificial sequence
<220> FEATURE:
<223> OTHER INFORMATION: Description of the artificial sequence:
      Fragment of the Saccharomyces cerevisiae Las17 protein
<220> FEATURE:
<221> NAME/KEY: CDS
<222> LOCATION: (1)..(561)

<400> SEQUENCE: 71

```
gga caa cct gca gtt ccc ctt cct cag aat act caa gca cct tcg caa      48
Gly Gln Pro Ala Val Pro Leu Pro Gln Asn Thr Gln Ala Pro Ser Gln
 1               5                  10                  15 gcc aca aat gtg cca gtg gca cca cca cct cct ccg gca tct tta ggc      96
Ala Thr Asn Val Pro Val Ala Pro Pro Pro Pro Pro Ala Ser Leu Gly
             20                  25                  30 cag tcg cag ata cct cag tca gca ccc tca gca cct att ccg cca acg     144
Gln Ser Gln Ile Pro Gln Ser Ala Pro Ser Ala Pro Ile Pro Pro Thr
         35                  40                  45 tta cca tcg acg acg agt gct gca cca cct ccg cca cca gca ttc cta     192
Leu Pro Ser Thr Thr Ser Ala Ala Pro Pro Pro Pro Pro Ala Phe Leu
     50                  55                  60 act caa caa cct caa tct gga gga gct cca gct cca ccc cca cct cct     240
Thr Gln Gln Pro Gln Ser Gly Gly Ala Pro Ala Pro Pro Pro Pro Pro
 65                  70                  75                  80 caa atg cca gct aca tca aca tcc gga ggc ggt tca ttc gct gaa act     288
Gln Met Pro Ala Thr Ser Thr Ser Gly Gly Gly Ser Phe Ala Glu Thr
                 85                  90                  95 act gga gat gca ggt cgt gat gca ctt tta gct tca att aga ggg gca     336
Thr Gly Asp Ala Gly Arg Asp Ala Leu Leu Ala Ser Ile Arg Gly Ala
            100                 105                 110 ggt gga ata ggc gct ttg aga aaa gtt gac aaa tcg cag cta gat aag     384
Gly Gly Ile Gly Ala Leu Arg Lys Val Asp Lys Ser Gln Leu Asp Lys
        115                 120                 125 ccc tca gtt tta ctg cag gaa gca cgt gga gaa tct gct tca cca cca     432
Pro Ser Val Leu Leu Gln Glu Ala Arg Gly Glu Ser Ala Ser Pro Pro
    130                 135                 140 gca gcg gct gga aat gga ggc aca cct ggt gga cct ccg gct tct tta     480
Ala Ala Ala Gly Asn Gly Gly Thr Pro Gly Gly Pro Pro Ala Ser Leu
145                 150                 155                 160 gca gat gcg ttg gca gca gct tta aac aaa aga aaa act aaa gtg gga     528
Ala Asp Ala Leu Ala Ala Ala Leu Asn Lys Arg Lys Thr Lys Val Gly
                165                 170                 175 gct cat gac gat atg gac aat ggt gat gat tgg                         561
Ala His Asp Asp Met Asp Asn Gly Asp Asp Trp
            180                 185
```

<210> SEQ ID NO 72
<211> LENGTH: 187
<212> TYPE: PRT
<213> ORGANISM: Artificial sequence
<220> FEATURE:
<223> OTHER INFORMATION: Description of the artificial sequence:
      Fragment of the Saccharomyces cerevisiae Las17 protein

<400> SEQUENCE: 72

Gly Gln Pro Ala Val Pro Leu Pro Gln Asn Thr Gln Ala Pro Ser Gln
 1               5                  10                  15

```
Ala Thr Asn Val Pro Val Ala Pro Pro Pro Pro Ala Ser Leu Gly
            20                  25                  30
Gln Ser Gln Ile Pro Gln Ser Ala Pro Ser Ala Pro Ile Pro Pro Thr
        35                  40                  45
Leu Pro Ser Thr Thr Ser Ala Ala Pro Pro Pro Pro Ala Phe Leu
    50                  55                  60
Thr Gln Gln Pro Gln Ser Gly Gly Ala Pro Ala Pro Pro Pro Pro
65                  70                  75                  80
Gln Met Pro Ala Thr Ser Thr Ser Gly Gly Gly Ser Phe Ala Glu Thr
                85                  90                  95
Thr Gly Asp Ala Gly Arg Asp Ala Leu Leu Ala Ser Ile Arg Gly Ala
            100                 105                 110
Gly Gly Ile Gly Ala Leu Arg Lys Val Asp Lys Ser Gln Leu Asp Lys
        115                 120                 125
Pro Ser Val Leu Leu Gln Glu Ala Arg Gly Glu Ser Ala Ser Pro Pro
    130                 135                 140
Ala Ala Ala Gly Asn Gly Gly Thr Pro Gly Gly Pro Pro Ala Ser Leu
145                 150                 155                 160
Ala Asp Ala Leu Ala Ala Leu Asn Lys Arg Lys Thr Lys Val Gly
                165                 170                 175
Ala His Asp Asp Met Asp Asn Gly Asp Asp Trp
            180                 185
```

<210> SEQ ID NO 73
<211> LENGTH: 534
<212> TYPE: DNA
<213> ORGANISM: Artificial sequence
<220> FEATURE:
<223> OTHER INFORMATION: Description of the artificial sequence:
    Fragment of the Saccharomyces cerevisiae Las17 protein
<220> FEATURE:
<221> NAME/KEY: CDS
<222> LOCATION: (1)..(534)

<400> SEQUENCE: 73

```
gga caa cct gca gtt ccc ctt cct cag aat act caa gca cct tcg caa      48
Gly Gln Pro Ala Val Pro Leu Pro Gln Asn Thr Gln Ala Pro Ser Gln
  1               5                  10                  15 gcc aca aat gtg cca gtg gca cca cca cct cct ccg gca tct tta ggc      96
Ala Thr Asn Val Pro Val Ala Pro Pro Pro Pro Ala Ser Leu Gly
            20                  25                  30 cag tcg cag ata cct cag tca gca ccc tca gca cct att ccg cca acg     144
Gln Ser Gln Ile Pro Gln Ser Ala Pro Ser Ala Pro Ile Pro Pro Thr
        35                  40                  45 tta cca tcg acg acg agt gct gca cca cct ccg cca cca gca ttc cta     192
Leu Pro Ser Thr Thr Ser Ala Ala Pro Pro Pro Pro Ala Phe Leu
    50                  55                  60 act caa caa cct caa tct gga gga gct cca gct cca ccc cca cct cct     240
Thr Gln Gln Pro Gln Ser Gly Gly Ala Pro Ala Pro Pro Pro Pro
65                  70                  75                  80 caa atg cca gct aca tca aca tcc gga ggc ggt tca ttc gct gaa act     288
Gln Met Pro Ala Thr Ser Thr Ser Gly Gly Gly Ser Phe Ala Glu Thr
                85                  90                  95 act gga gat gca ggt cgt gat gca ctt tta gct tca att aga ggg gca     336
Thr Gly Asp Ala Gly Arg Asp Ala Leu Leu Ala Ser Ile Arg Gly Ala
            100                 105                 110 ggt ggc ata ggc gct ttg aga aaa gtt gac aaa tcg cag cta gat aag     384
Gly Gly Ile Gly Ala Leu Arg Lys Val Asp Lys Ser Gln Leu Asp Lys
        115                 120                 125
```

```
ccc tca gtt tta ctg cag gaa gca cgt gga gaa tct gct tca cca cca    432
Pro Ser Val Leu Leu Gln Glu Ala Arg Gly Glu Ser Ala Ser Pro Pro
    130                 135                 140 gca gcg gct gga aat gga ggc aca cct ggt gga cct ccg gct tct tta    480
Ala Ala Ala Gly Asn Gly Gly Thr Pro Gly Gly Pro Pro Ala Ser Leu
145                 150                 155                 160 gca gat gcg ttg gca gca gct tta aac aaa aga aaa act aaa gtg gga    528
Ala Asp Ala Leu Ala Ala Ala Leu Asn Lys Arg Lys Thr Lys Val Gly
                165                 170                 175 gct cat                                                            534
Ala His

<210> SEQ ID NO 74
<211> LENGTH: 178
<212> TYPE: PRT
<213> ORGANISM: Artificial sequence
<220> FEATURE:
<223> OTHER INFORMATION: Description of the artificial sequence:
      Fragment of the Saccharomyces cerevisiae Las17 protein

<400> SEQUENCE: 74

Gly Gln Pro Ala Val Pro Leu Pro Gln Asn Thr Gln Ala Pro Ser Gln
 1               5                  10                  15

Ala Thr Asn Val Pro Val Ala Pro Pro Pro Pro Ala Ser Leu Gly
            20                  25                  30

Gln Ser Gln Ile Pro Gln Ser Ala Pro Ser Ala Pro Ile Pro Pro Thr
        35                  40                  45

Leu Pro Ser Thr Thr Ser Ala Ala Pro Pro Pro Pro Ala Phe Leu
    50                  55                  60

Thr Gln Gln Pro Gln Ser Gly Gly Ala Pro Ala Pro Pro Pro Pro
65                  70                  75                  80

Gln Met Pro Ala Thr Ser Thr Ser Gly Gly Gly Ser Phe Ala Glu Thr
                85                  90                  95

Thr Gly Asp Ala Gly Arg Asp Ala Leu Leu Ala Ser Ile Arg Gly Ala
            100                 105                 110

Gly Gly Ile Gly Ala Leu Arg Lys Val Asp Lys Ser Gln Leu Asp Lys
        115                 120                 125

Pro Ser Val Leu Leu Gln Glu Ala Arg Gly Glu Ser Ala Ser Pro Pro
    130                 135                 140

Ala Ala Ala Gly Asn Gly Gly Thr Pro Gly Gly Pro Pro Ala Ser Leu
145                 150                 155                 160

Ala Asp Ala Leu Ala Ala Ala Leu Asn Lys Arg Lys Thr Lys Val Gly
                165                 170                 175
Ala His

<210> SEQ ID NO 75
<211> LENGTH: 2454
<212> TYPE: DNA
<213> ORGANISM: Schizosaccharomyces pombe
<220> FEATURE:
<221> NAME/KEY: CDS
<222> LOCATION: (404)..(2125)

<400> SEQUENCE: 75
ttctaataat taatgattat gattaagtca ttttttttaat aatcttataa taaactaaca     60
ttatgagaca agcaaacttc gtatggttga ataaattta tttacctctt tacaatgagg     120
acgataagta tgtagaatgt aaaaaatatt aaacccgaat taatgtctca agttttatta    180
atctataaac agttaatata attagcaaaa tttaccagct gctaataagt gcgttgcaaa    240
```

-continued

```
tttttatagt acatagcgta gtatagtata gtatactaca ctaattatca ctcattggct         300
tgttaactac agtgaaaatg ctaacaaacg ggaggaacca aaacaccact tataccactg        360
tgagacagca attttttgaat tgcattacaa tccgaaaatt caa atg cct cca tct        415
                                              Met Pro Pro Ser
                                               1
```

| | | | | | | | | | | | | | | | | |
|---|---|---|---|---|---|---|---|---|---|---|---|---|---|---|---|---|
| tcc | tct | ata | act | caa | gag | gat | aag | gca | act | atc | cgt | aaa | tac | ata | cct | 463 |
| Ser | Ser | Ile | Thr | Gln | Glu | Asp | Lys | Ala | Thr | Ile | Arg | Lys | Tyr | Ile | Pro | |
| 5 | | | | 10 | | | | | 15 | | | | | 20 | | |
| aaa | agc | aca | aat | aaa | atc | att | gca | gca | gcc | gtc | gtc | aag | cta | tat | gta | 511 |
| Lys | Ser | Thr | Asn | Lys | Ile | Ile | Ala | Ala | Ala | Val | Val | Lys | Leu | Tyr | Val | |
| | | | 25 | | | | | 30 | | | | | 35 | | | |
| gct | tat | cct | gat | ccg | aac | aaa | tgg | aat | tat | aca | ggt | ctt | tgt | ggt | gct | 559 |
| Ala | Tyr | Pro | Asp | Pro | Asn | Lys | Trp | Asn | Tyr | Thr | Gly | Leu | Cys | Gly | Ala | |
| | | | 40 | | | | 45 | | | | | 50 | | | | |
| ctt | gta | ttg | tcc | tat | gat | aca | aca | gca | aaa | tgc | tgt | tgg | ttt | aaa | ctg | 607 |
| Leu | Val | Leu | Ser | Tyr | Asp | Thr | Thr | Ala | Lys | Cys | Cys | Trp | Phe | Lys | Leu | |
| | | 55 | | | | | 60 | | | | | 65 | | | | |
| gtt | gac | gtt | gtg | aat | aat | agt | ggt | ata | ata | tgg | gac | caa | gag | ctt | tat | 655 |
| Val | Asp | Val | Val | Asn | Asn | Ser | Gly | Ile | Ile | Trp | Asp | Gln | Glu | Leu | Tyr | |
| | 70 | | | | | 75 | | | | | 80 | | | | | |
| caa | aat | atg | gac | tat | cgc | caa | gat | cgt | aca | ttt | ttt | cat | tct | ttc | gag | 703 |
| Gln | Asn | Met | Asp | Tyr | Arg | Gln | Asp | Arg | Thr | Phe | Phe | His | Ser | Phe | Glu | |
| 85 | | | | | 90 | | | | | 95 | | | | | 100 | |
| ctt | gat | aaa | tgc | cta | gca | ggt | ttt | agt | ttt | gca | aac | gag | aca | gac | gct | 751 |
| Leu | Asp | Lys | Cys | Leu | Ala | Gly | Phe | Ser | Phe | Ala | Asn | Glu | Thr | Asp | Ala | |
| | | | 105 | | | | | 110 | | | | | 115 | | | |
| caa | aaa | ttt | tac | aaa | aag | gtt | tta | gat | aaa | ggt | tgc | cat | cct | gaa | tca | 799 |
| Gln | Lys | Phe | Tyr | Lys | Lys | Val | Leu | Asp | Lys | Gly | Cys | His | Pro | Glu | Ser | |
| | | | 120 | | | | | 125 | | | | | 130 | | | |
| att | gag | aat | ccg | gtt | ttg | tca | ttt | att | acc | aga | aaa | ggt | tct | tct | aga | 847 |
| Ile | Glu | Asn | Pro | Val | Leu | Ser | Phe | Ile | Thr | Arg | Lys | Gly | Ser | Ser | Arg | |
| | | 135 | | | | | 140 | | | | | 145 | | | | |
| cat | gcg | cct | aac | aac | agc | aat | atc | caa | cct | ccc | tca | gct | gct | cct | cct | 895 |
| His | Ala | Pro | Asn | Asn | Ser | Asn | Ile | Gln | Pro | Pro | Ser | Ala | Ala | Pro | Pro | |
| | 150 | | | | | 155 | | | | | 160 | | | | | |
| gta | cct | gga | aag | gaa | aat | tat | aat | gct | gtt | gga | tct | aaa | agt | ccc | aat | 943 |
| Val | Pro | Gly | Lys | Glu | Asn | Tyr | Asn | Ala | Val | Gly | Ser | Lys | Ser | Pro | Asn | |
| 165 | | | | | 170 | | | | | 175 | | | | | 180 | |
| gag | ccc | gag | ctt | tta | aat | tcg | ctt | gat | ccg | agc | tta | att | gat | tct | cta | 991 |
| Glu | Pro | Glu | Leu | Leu | Asn | Ser | Leu | Asp | Pro | Ser | Leu | Ile | Asp | Ser | Leu | |
| | | | 185 | | | | | 190 | | | | | 195 | | | |
| atg | aag | atg | ggc | att | tcc | cag | gat | caa | att | gct | gaa | aac | gca | gat | ttc | 1039 |
| Met | Lys | Met | Gly | Ile | Ser | Gln | Asp | Gln | Ile | Ala | Glu | Asn | Ala | Asp | Phe | |
| | | | 200 | | | | | 205 | | | | | 210 | | | |
| gtc | aaa | gcg | tac | ctt | aat | gaa | tca | gct | ggt | aca | cct | acc | agt | act | tct | 1087 |
| Val | Lys | Ala | Tyr | Leu | Asn | Glu | Ser | Ala | Gly | Thr | Pro | Thr | Ser | Thr | Ser | |
| | | 215 | | | | | 220 | | | | | 225 | | | | |
| gca | cct | ccc | atc | cct | cca | agc | att | cct | tcc | tct | cgt | ccc | cca | gag | cgt | 1135 |
| Ala | Pro | Pro | Ile | Pro | Pro | Ser | Ile | Pro | Ser | Ser | Arg | Pro | Pro | Glu | Arg | |
| | 230 | | | | | 235 | | | | | 240 | | | | | |
| gtt | cct | tct | gtg | tct | gca | cct | gct | cct | ccc | cca | att | cca | cct | cca | tct | 1183 |
| Val | Pro | Ser | Val | Ser | Ala | Pro | Ala | Pro | Pro | Pro | Ile | Pro | Pro | Pro | Ser | |
| 245 | | | | | 250 | | | | | 255 | | | | | 260 | |
| aat | gga | act | gtc | tct | tct | cct | cct | aac | tcc | cct | ccc | cgt | cct | atc | gct | 1231 |
| Asn | Gly | Thr | Val | Ser | Ser | Pro | Pro | Asn | Ser | Pro | Pro | Arg | Pro | Ile | Ala | |
| | | | 265 | | | | | 270 | | | | | 275 | | | |
| cct | gtt | tcg | atg | aat | cct | gct | att | aat | tcc | acc | tcg | aaa | cct | cca | ctc | 1279 |
| Pro | Val | Ser | Met | Asn | Pro | Ala | Ile | Asn | Ser | Thr | Ser | Lys | Pro | Pro | Leu | |

-continued

```
                     280                 285                 290
cct cca cca tct tca aga gtc agt gcg gca gct cta gct gct aac aaa    1327
Pro Pro Pro Ser Ser Arg Val Ser Ala Ala Ala Leu Ala Ala Asn Lys
        295                 300                 305 aaa cga cct cct ccg cct ccg cct cca tcc cgt cgt aat cgt ggt aaa    1375
Lys Arg Pro Pro Pro Pro Pro Pro Ser Arg Arg Asn Arg Gly Lys
310                 315                 320 cca ccg att ggt aat ggt tct tct aac tcg tct ctt cct cca cct cca    1423
Pro Pro Ile Gly Asn Gly Ser Ser Asn Ser Ser Leu Pro Pro Pro
325                 330                 335                 340 cca cct cct aga tct aat gct gct ggc tca att cct ttg ccg cct caa    1471
Pro Pro Pro Arg Ser Asn Ala Ala Gly Ser Ile Pro Leu Pro Pro Gln
                345                 350                 355 ggt aga tct gct cct cct cca cct cct cca agg tct gct cct tcc act    1519
Gly Arg Ser Ala Pro Pro Pro Pro Pro Arg Ser Ala Pro Ser Thr
            360                 365                 370 ggg aga caa cca ccc cct tta tct tca tct cgt gca gtt tca aac cca    1567
Gly Arg Gln Pro Pro Pro Leu Ser Ser Ser Arg Ala Val Ser Asn Pro
        375                 380                 385 cca gcc cct cct cca gct att cct ggt cgt tct gcg cct gca ctt ccc    1615
Pro Ala Pro Pro Pro Ala Ile Pro Gly Arg Ser Ala Pro Ala Leu Pro
390                 395                 400 cct ctt ggt aat gca tca cga aca agc aca cct cct gtc cct aca cct    1663
Pro Leu Gly Asn Ala Ser Arg Thr Ser Thr Pro Pro Val Pro Thr Pro
405                 410                 415                 420 cct tct ctt cct cct agt gca cct cca tct ttg ccc ccc agt gca cca    1711
Pro Ser Leu Pro Pro Ser Ala Pro Pro Ser Leu Pro Pro Ser Ala Pro
                425                 430                 435 cct tct cta cct atg ggc gca cca gct gct ccc ccc cta cca cct agt    1759
Pro Ser Leu Pro Met Gly Ala Pro Ala Ala Pro Pro Leu Pro Pro Ser
            440                 445                 450 gca cca att gct cct cct cta ccc gct ggt atg cca gct gct cca cca    1807
Ala Pro Ile Ala Pro Pro Leu Pro Ala Gly Met Pro Ala Ala Pro Pro
        455                 460                 465 ttg cct ccc gct gca cca gct cct cct cca gct cca gct cct gcg ccc    1855
Leu Pro Pro Ala Ala Pro Ala Pro Pro Pro Ala Pro Ala Pro Ala Pro
470                 475                 480 gcc gcg cct gtt gct tcg ata gct gaa ttg cct caa caa gac ggc cgt    1903
Ala Ala Pro Val Ala Ser Ile Ala Glu Leu Pro Gln Gln Asp Gly Arg
485                 490                 495                 500 gct aat tta atg gcc agt atc aga gcc agc ggt ggt atg gat tta ctg    1951
Ala Asn Leu Met Ala Ser Ile Arg Ala Ser Gly Gly Met Asp Leu Leu
                505                 510                 515 aaa agc agg aaa gta tct gct tct cct agt gtc gca tct aca aaa act    1999
Lys Ser Arg Lys Val Ser Ala Ser Pro Ser Val Ala Ser Thr Lys Thr
            520                 525                 530 tcg aat cct ccg gta gaa gca ccc cct tct aac aat ctt atg gat gca    2047
Ser Asn Pro Pro Val Glu Ala Pro Pro Ser Asn Asn Leu Met Asp Ala
        535                 540                 545 ttg gca agc gct ttg aac caa cgt aaa acc aaa gtc gct cag agt gac    2095
Leu Ala Ser Ala Leu Asn Gln Arg Lys Thr Lys Val Ala Gln Ser Asp
550                 555                 560 gaa gag gat gaa gac gac gat gag tgg gac tagttattaa tatctttgaa      2145
Glu Glu Asp Glu Asp Asp Asp Glu Trp Asp
565                 570 attacctata cttttttgat tcacacagtc ttttaaagtt ttgttaaacg acttcactat    2205
ttttatttgg atttgtgttt attgtattag agcaaacacc attattcta aattgaataa     2265 cgcgaatttg tgttgatatt actattcata tatcgcaaca cagtgtgtat ctttacttta    2325
```

-continued

```
ttgtaagtat gggagcagtc acacatttcg gtaccacaac tttagaaacg tcaagttcaa    2385
gtccttccac aaccaaaaac gtttggtcaa atagaaacaa atggatcctc tagagtcgac    2445
ctgcagcaa                                                            2454
```

<210> SEQ ID NO 76
<211> LENGTH: 574
<212> TYPE: PRT
<213> ORGANISM: Schizosaccharomyces pombe

<400> SEQUENCE: 76

```
Met Pro Pro Ser Ser Ser Ile Thr Gln Glu Asp Lys Ala Thr Ile Arg
 1               5                  10                  15

Lys Tyr Ile Pro Lys Ser Thr Asn Lys Ile Ile Ala Ala Ala Val Val
                20                  25                  30

Lys Leu Tyr Val Ala Tyr Pro Asp Pro Asn Lys Trp Asn Tyr Thr Gly
            35                  40                  45

Leu Cys Gly Ala Leu Val Leu Ser Tyr Asp Thr Thr Ala Lys Cys Cys
        50                  55                  60

Trp Phe Lys Leu Val Asp Val Val Asn Asn Ser Gly Ile Ile Trp Asp
 65                  70                  75                  80

Gln Glu Leu Tyr Gln Asn Met Asp Tyr Arg Gln Asp Arg Thr Phe Phe
                85                  90                  95

His Ser Phe Glu Leu Asp Lys Cys Leu Ala Gly Phe Ser Phe Ala Asn
               100                 105                 110

Glu Thr Asp Ala Gln Lys Phe Tyr Lys Lys Val Leu Asp Lys Gly Cys
           115                 120                 125

His Pro Glu Ser Ile Glu Asn Pro Val Leu Ser Phe Ile Thr Arg Lys
       130                 135                 140

Gly Ser Ser Arg His Ala Pro Asn Asn Ser Asn Ile Gln Pro Pro Ser
145                 150                 155                 160

Ala Ala Pro Pro Val Pro Gly Lys Glu Asn Tyr Asn Ala Val Gly Ser
               165                 170                 175

Lys Ser Pro Asn Glu Pro Glu Leu Leu Asn Ser Leu Asp Pro Ser Leu
           180                 185                 190

Ile Asp Ser Leu Met Lys Met Gly Ile Ser Gln Asp Gln Ile Ala Glu
       195                 200                 205

Asn Ala Asp Phe Val Lys Ala Tyr Leu Asn Glu Ser Ala Gly Thr Pro
   210                 215                 220

Thr Ser Thr Ser Ala Pro Pro Ile Pro Pro Ser Ile Pro Ser Ser Arg
225                 230                 235                 240

Pro Pro Glu Arg Val Pro Ser Val Ser Ala Pro Ala Pro Pro Ile
               245                 250                 255

Pro Pro Pro Ser Asn Gly Thr Val Ser Ser Pro Asn Ser Pro Pro
           260                 265                 270

Arg Pro Ile Ala Pro Val Ser Met Asn Pro Ala Ile Asn Ser Thr Ser
       275                 280                 285

Lys Pro Pro Leu Pro Pro Ser Ser Arg Val Ser Ala Ala Ala Leu
   290                 295                 300

Ala Ala Asn Lys Lys Arg Pro Pro Pro Pro Ser Arg Arg
305                 310                 315                 320

Asn Arg Gly Lys Pro Pro Ile Gly Asn Gly Ser Ser Asn Ser Ser Leu
               325                 330                 335

Pro Pro Pro Pro Pro Pro Arg Ser Asn Ala Ala Gly Ser Ile Pro
```

```
                        340             345             350
Leu Pro Pro Gln Gly Arg Ser Ala Pro Pro Pro Pro Arg Ser
            355                 360             365

Ala Pro Ser Thr Gly Arg Gln Pro Pro Leu Ser Ser Arg Ala
        370                 375             380

Val Ser Asn Pro Pro Ala Pro Pro Ala Ile Pro Gly Arg Ser Ala
385                 390             395                 400

Pro Ala Leu Pro Pro Leu Gly Asn Ala Ser Arg Thr Ser Thr Pro Pro
                405                 410             415

Val Pro Thr Pro Pro Ser Leu Pro Pro Ser Ala Pro Pro Ser Leu Pro
            420                 425             430

Pro Ser Ala Pro Pro Ser Leu Pro Met Gly Ala Pro Ala Ala Pro Pro
            435                 440             445

Leu Pro Pro Ser Ala Pro Ile Ala Pro Pro Leu Pro Ala Gly Met Pro
        450                 455             460

Ala Ala Pro Pro Leu Pro Ala Ala Pro Ala Pro Pro Ala Pro
465                 470             475             480

Ala Pro Ala Pro Ala Ala Pro Val Ala Ser Ile Ala Glu Leu Pro Gln
            485                 490             495

Gln Asp Gly Arg Ala Asn Leu Met Ala Ser Ile Arg Ala Ser Gly Gly
            500                 505             510

Met Asp Leu Leu Lys Ser Arg Lys Val Ser Ala Ser Pro Ser Val Ala
            515                 520             525

Ser Thr Lys Thr Ser Asn Pro Pro Val Glu Ala Pro Pro Ser Asn Asn
        530                 535             540

Leu Met Asp Ala Leu Ala Ser Ala Leu Asn Gln Arg Lys Thr Lys Val
545                 550             555             560

Ala Gln Ser Asp Glu Glu Asp Glu Asp Asp Glu Trp Asp
                565             570
```

```
<210> SEQ ID NO 77
<211> LENGTH: 294
<212> TYPE: DNA
<213> ORGANISM: Artificial sequence
<220> FEATURE:
<223> OTHER INFORMATION: Description of the artificial sequence:
      Fragment of the homologuous protein WASP (Wsp1p) of
      Schizosaccharomyces pombe
<220> FEATURE:
<221> NAME/KEY: CDS
<222> LOCATION: (1)..(294)

<400> SEQUENCE: 77 cct cca gct cca gct cct gcg ccc gcc gcg cct gtt gct tcg ata gct    48
Pro Pro Ala Pro Ala Pro Ala Pro Ala Ala Pro Val Ala Ser Ile Ala
1               5                   10                  15 gaa ttg cct caa caa gac ggc cgt gct aat tta atg gcc agt atc aga    96
Glu Leu Pro Gln Gln Asp Gly Arg Ala Asn Leu Met Ala Ser Ile Arg
            20                  25                  30 gcc agc ggt ggt atg gat tta ctg aaa agc agg aaa gta tct gct tct   144
Ala Ser Gly Gly Met Asp Leu Leu Lys Ser Arg Lys Val Ser Ala Ser
        35                  40                  45 cct agt gtc gca tct aca aaa act tcg aat cct ccg gta gaa gca ccc   192
Pro Ser Val Ala Ser Thr Lys Thr Ser Asn Pro Pro Val Glu Ala Pro
    50                  55                  60 cct tct aac aat ctt atg gat gca ttg gca agc gct ttg aac caa cgt   240
Pro Ser Asn Asn Leu Met Asp Ala Leu Ala Ser Ala Leu Asn Gln Arg
65                  70                  75                  80
```

```
aaa acc aaa gtc gct cag agt gac gaa gag gat gaa gac gac gat gag      288
Lys Thr Lys Val Ala Gln Ser Asp Glu Glu Asp Glu Asp Asp Asp Glu
             85                  90                  95 tgg gac                                                               294
Trp Asp <210> SEQ ID NO 78
<211> LENGTH: 98
<212> TYPE: PRT
<213> ORGANISM: Artificial sequence
<220> FEATURE:
<223> OTHER INFORMATION: Description of the artificial sequence:
      Fragment of the homologuous protein WASP (Wsp1p) of
      Schizosaccharomyces pombe

<400> SEQUENCE: 78

Pro Pro Ala Pro Ala Pro Ala Pro Ala Pro Val Ala Ser Ile Ala
  1               5                  10                  15

Glu Leu Pro Gln Gln Asp Gly Arg Ala Asn Leu Met Ala Ser Ile Arg
                 20                  25                  30

Ala Ser Gly Gly Met Asp Leu Leu Lys Ser Arg Lys Val Ser Ala Ser
             35                  40                  45

Pro Ser Val Ala Ser Thr Lys Thr Ser Asn Pro Pro Val Glu Ala Pro
         50                  55                  60

Pro Ser Asn Asn Leu Met Asp Ala Leu Ala Ser Ala Leu Asn Gln Arg
 65                  70                  75                  80

Lys Thr Lys Val Ala Gln Ser Asp Glu Glu Asp Glu Asp Asp Asp Glu
             85                  90                  95
Trp Asp

<210> SEQ ID NO 79
<211> LENGTH: 267
<212> TYPE: DNA
<213> ORGANISM: Artificial sequence
<220> FEATURE:
<223> OTHER INFORMATION: Description of the artificial sequence:
      Fragment of the homologuous protein WASP (Wsp1p) of
      Schizosaccharomyces pombe
<220> FEATURE:
<221> NAME/KEY: CDS
<222> LOCATION: (1)..(267)

<400> SEQUENCE: 79 cct cca gct cca gct cct gcg ccc gcc gcg cct gtt gct tcg ata gct       48
Pro Pro Ala Pro Ala Pro Ala Pro Ala Pro Val Ala Ser Ile Ala
  1               5                  10                  15 gaa ttg cct caa caa gac ggc cgt gct aat tta atg gcc agt atc aga       96
Glu Leu Pro Gln Gln Asp Gly Arg Ala Asn Leu Met Ala Ser Ile Arg
                 20                  25                  30 gcc agc ggt ggt atg gat tta ctg aaa agc agg aaa gta tct gct tct      144
Ala Ser Gly Gly Met Asp Leu Leu Lys Ser Arg Lys Val Ser Ala Ser
             35                  40                  45 cct agt gtc gca tct aca aaa act tcg aat cct ccg gta gaa gca ccc      192
Pro Ser Val Ala Ser Thr Lys Thr Ser Asn Pro Pro Val Glu Ala Pro
         50                  55                  60 cct tct aac aat ctt atg gat gca ttg gca agc gct ttg aac caa cgt      240
Pro Ser Asn Asn Leu Met Asp Ala Leu Ala Ser Ala Leu Asn Gln Arg
 65                  70                  75                  80 aaa acc aaa gtc gct cag agt gac gaa                                  267
Lys Thr Lys Val Ala Gln Ser Asp Glu
             85

<210> SEQ ID NO 80
```

```
<211> LENGTH: 89
<212> TYPE: PRT
<213> ORGANISM: Artificial sequence
<220> FEATURE:
<223> OTHER INFORMATION: Description of the artificial sequence:
      Fragment of the homologuous protein WASP (Wsp1p) of
      Schizosaccharomyces pombe

<400> SEQUENCE: 80

Pro Pro Ala Pro Ala Pro Ala Pro Ala Ala Pro Val Ala Ser Ile Ala
 1               5                  10                  15

Glu Leu Pro Gln Gln Asp Gly Arg Ala Asn Leu Met Ala Ser Ile Arg
                20                  25                  30

Ala Ser Gly Gly Met Asp Leu Leu Lys Ser Arg Lys Val Ser Ala Ser
            35                  40                  45

Pro Ser Val Ala Ser Thr Lys Thr Ser Asn Pro Pro Val Glu Ala Pro
        50                  55                  60

Pro Ser Asn Asn Leu Met Asp Ala Leu Ala Ser Ala Leu Asn Gln Arg
 65                  70                  75                  80

Lys Thr Lys Val Ala Gln Ser Asp Glu
                85

<210> SEQ ID NO 81
<211> LENGTH: 222
<212> TYPE: DNA
<213> ORGANISM: Artificial sequence
<220> FEATURE:
<223> OTHER INFORMATION: Description of the artificial sequence:
      Fragment of the homologuous protein WASP (Wsp1p) of
      Schizosaccharomyces pombe
<220> FEATURE:
<221> NAME/KEY: CDS
<222> LOCATION: (1)..(222)

<400> SEQUENCE: 81 gct aat tta atg gcc agt atc aga gcc agc ggt ggt atg gat tta ctg      48
Ala Asn Leu Met Ala Ser Ile Arg Ala Ser Gly Gly Met Asp Leu Leu
 1               5                  10                  15 aaa agc agg aaa gta tct gct tct cct agt gtc gca tct aca aaa act      96
Lys Ser Arg Lys Val Ser Ala Ser Pro Ser Val Ala Ser Thr Lys Thr
                20                  25                  30 tcg aat cct ccg gta gaa gca ccc cct tct aac aat ctt atg gat gca     144
Ser Asn Pro Pro Val Glu Ala Pro Pro Ser Asn Asn Leu Met Asp Ala
            35                  40                  45 ttg gca agc gct ttg aac caa cgt aaa acc aaa gtc gct cag agt gac     192
Leu Ala Ser Ala Leu Asn Gln Arg Lys Thr Lys Val Ala Gln Ser Asp
        50                  55                  60 gaa gag gat gaa gac gac gat gag tgg gac                             222
Glu Glu Asp Glu Asp Asp Asp Glu Trp Asp
 65                  70

<210> SEQ ID NO 82
<211> LENGTH: 74
<212> TYPE: PRT
<213> ORGANISM: Artificial sequence
<220> FEATURE:
<223> OTHER INFORMATION: Description of the artificial sequence:
      Fragment of the homologuous protein WASP (Wsp1p) of
      Schizosaccharomyces pombe

<400> SEQUENCE: 82

Ala Asn Leu Met Ala Ser Ile Arg Ala Ser Gly Gly Met Asp Leu Leu
 1               5                  10                  15

Lys Ser Arg Lys Val Ser Ala Ser Pro Ser Val Ala Ser Thr Lys Thr
```

```
                    20                  25                  30
Ser Asn Pro Pro Val Glu Ala Pro Pro Ser Asn Asn Leu Met Asp Ala
        35                  40                  45

Leu Ala Ser Ala Leu Asn Gln Arg Lys Thr Lys Val Ala Gln Ser Asp
    50                  55                  60

Glu Glu Asp Glu Asp Asp Glu Trp Asp
65                  70
```

<210> SEQ ID NO 83
<211> LENGTH: 195
<212> TYPE: DNA
<213> ORGANISM: Artificial sequence
<220> FEATURE:
<223> OTHER INFORMATION: Description of the artificial sequence:
      Fragment of the homologuous protein WASP (Wsp1p) of
      Schizosaccharomyces pombe
<220> FEATURE:
<221> NAME/KEY: CDS
<222> LOCATION: (1)..(195)

<400> SEQUENCE: 83

```
gct aat tta atg gcc agt atc aga gcc agc ggt ggt atg gat tta ctg      48
Ala Asn Leu Met Ala Ser Ile Arg Ala Ser Gly Gly Met Asp Leu Leu
  1               5                  10                  15 aaa agc agg aaa gta tct gct tct cct agt gtc gca tct aca aaa act      96
Lys Ser Arg Lys Val Ser Ala Ser Pro Ser Val Ala Ser Thr Lys Thr
                 20                  25                  30 tcg aat cct ccg gta gaa gca ccc cct tct aac aat ctt atg gat gca     144
Ser Asn Pro Pro Val Glu Ala Pro Pro Ser Asn Asn Leu Met Asp Ala
         35                  40                  45 ttg gca agc gct ttg aac caa cgt aaa acc aaa gtc gct cag agt gac     192
Leu Ala Ser Ala Leu Asn Gln Arg Lys Thr Lys Val Ala Gln Ser Asp
     50                  55                  60 gaa                                                                  195
Glu
 65
```

<210> SEQ ID NO 84
<211> LENGTH: 65
<212> TYPE: PRT
<213> ORGANISM: Artificial sequence
<220> FEATURE:
<223> OTHER INFORMATION: Description of the artificial sequence:
      Fragment of the homologuous protein WASP (Wsp1p) of
      Schizosaccharomyces pombe

<400> SEQUENCE: 84

```
Ala Asn Leu Met Ala Ser Ile Arg Ala Ser Gly Gly Met Asp Leu Leu
  1               5                  10                  15

Lys Ser Arg Lys Val Ser Ala Ser Pro Ser Val Ala Ser Thr Lys Thr
                 20                  25                  30

Ser Asn Pro Pro Val Glu Ala Pro Pro Ser Asn Asn Leu Met Asp Ala
         35                  40                  45

Leu Ala Ser Ala Leu Asn Gln Arg Lys Thr Lys Val Ala Gln Ser Asp
     50                  55                  60

Glu
 65
```